US012633381B2

(12) United States Patent
Ryczko et al.

(10) Patent No.: US 12,633,381 B2
(45) Date of Patent: May 19, 2026

(54) METHODS AND SYSTEMS FOR MACHINE-LEARNING BASED MOLECULE GENERATION AND SCORING

(71) Applicant: Good Chemistry Inc., Tarrytown, NY (US)

(72) Inventors: Kevin Ryczko, Gatineau (CA); Amit Kadan, Vancouver (CA); Takeshi Yamazaki, Vancouver (CA)

(73) Assignee: Good Chemistry Inc., Vancouver (CA)

( * ) Notice: Subject to any disclaimer, the term of this patent is extended or adjusted under 35 U.S.C. 154(b) by 0 days.

(21) Appl. No.: 19/093,126

(22) Filed: Mar. 27, 2025

(65) Prior Publication Data

US 2025/0226064 A1     Jul. 10, 2025

Related U.S. Application Data

(63) Continuation of application No. 18/890,681, filed on Sep. 19, 2024, which is a continuation of application No. PCT/IB2024/056174, filed on Jun. 25, 2024.

(Continued)

(51) Int. Cl.
| | |
|---|---|
| *G01N 33/48* | (2006.01) |
| *G01N 33/50* | (2006.01) |
| *G16C 20/40* | (2019.01) |
| *G16C 20/50* | (2019.01) |
| *G16C 20/70* | (2019.01) |

(52) U.S. Cl.
CPC ............ *G16C 20/50* (2019.02); *G16C 20/40* (2019.02); *G16C 20/70* (2019.02)

(58) Field of Classification Search
CPC ................................ G16C 20/70; G16C 20/40
See application file for complete search history.

(56) References Cited

U.S. PATENT DOCUMENTS

| | | |
|---|---|---|
| 11,256,994 B1 | 2/2022 | Bucher et al. |
| 11,354,582 B1 | 6/2022 | Prat |

(Continued)

FOREIGN PATENT DOCUMENTS

| | | |
|---|---|---|
| CN | 113674159 A | 11/2021 |
| CN | 111899320 B | 5/2023 |

OTHER PUBLICATIONS

Anderson, Amy C. The Process of Structure-Based Drug Design. Chemistry & Biology 10(9):787-797 (2003).

(Continued)

*Primary Examiner* — Russell S Negin
(74) *Attorney, Agent, or Firm* — Fish & Richardson P.C.

(57) ABSTRACT

A method for machine learning aided modeling of two interacting structures may include: (a) receiving an input structure comprising an interaction region; (b) generating a plurality of candidate structures using a first differentiable machine learning model; (c) docking one or more candidate structures of the plurality of candidate structures at the interaction region of the input structure using a second differentiable machine learning model to predict a docking geometry; (d) ranking the one or more candidate structures of the plurality of candidate structures docked in (c) using a third differentiable machine learning model to predict a score; and (e) backpropagating the score to (i) the first differentiable machine learning model to update the plurality of candidate structures or (ii) the second differentiable machine learning model to update the docking geometry.

16 Claims, 14 Drawing Sheets

Related U.S. Application Data

(60) Provisional application No. 63/648,851, filed on May 17, 2024, provisional application No. 63/510,422, filed on Jun. 27, 2023.

(56) References Cited

U.S. PATENT DOCUMENTS

| | | | |
|---|---|---|---|
| 2010/0240773 | A1 | 9/2010 | Korzekwa et al. |
| 2011/0046982 | A1 | 2/2011 | Arya et al. |
| 2016/0378912 | A1 | 12/2016 | Ragno et al. |
| 2018/0107526 | A1 | 4/2018 | Dadashikelayeh et al. |
| 2021/0304847 | A1 | 9/2021 | Senior |
| 2022/0156580 | A1 | 5/2022 | Chao et al. |
| 2022/0348903 | A1 | 11/2022 | Ranganathan et al. |
| 2022/0351053 | A1 | 11/2022 | Norvaisas et al. |
| 2022/0383993 | A1 | 12/2022 | Yoo et al. |
| 2022/0406403 | A1 | 12/2022 | Singh et al. |
| 2023/0054552 | A1 | 2/2023 | Yang |
| 2023/0154089 | A1 | 5/2023 | Bradley et al. |
| 2023/0409913 | A1 | 12/2023 | Park et al. |
| 2024/0395364 | A1 | 11/2024 | Gniewek et al. |
| 2025/0014688 | A1 | 1/2025 | Ryczko et al. |
| 2025/0140356 | A1 | 5/2025 | Ryczko et al. |

OTHER PUBLICATIONS

Axelrod, S. et al. GEOM, energy-annotated molecular conformations for property prediction and molecular generation, scientific data, 9:185, 14 pages (2022).
Boitreaud et al., "OptiMol: Optimization of Binding Affinities in Chemical Space for Drug Discovery,". Journal of Chemical Information and Modeling, Sep. 28, 2020, 60(12):5658-5666.
Cornet, Fran9ois Raymond J. et al. Inverse-Design of Organometallic Catalysts With Guided Equivariant Diffusion. Proceedings of 37th Conference on Neural Information Processing Systems (pp. 1-9) (2023).
Cornet, Fran9ois Raymond J. et al. Om-Diff: Inverse-design of Organometallic CatalystsWith Guided Equivariant Denoising Diffusion. Theoretical and Computational Chemistry, ChemRxiv (pp. 1-38) (2024).
Corso, et al. Diffdock: Diffusion steps, twists, and turns for molecular docking. ar Xiv preprint arXiv:2210.01776 (pp. 1-29) (2022).
Dollar, Orion et al. Efficient 3D Molecular Design with an E(3) Invariant Transformer VAE. The Journal of Physical Chemistry A 127(37):7844-7852 (2023).
Filella-Merce et al., "Optimizing Drug Design by Merging Generative AI with Active Learning Frameworks," CoRR, Submitted May 4, 2023, arXiv:2305.06334vl, 32 pages.
Gebauer, Niklas WA. et al. Inverse Design of 3D Molecular Structures With Conditional Generative Neural Networks. Nature Communications 13(1):973 (pp. 1-11) (2022).
Gomez-Bombarelli, et al. Automatic chemical design using a data-driven continuous representation of molecules. arXiv preprint arXiv:1610.02415 (pp. 1-23) (2016).
Guan, Jiaqi et al. 3D Equivariant Diffusion for Target-Aware Molecule Generation and Affinity Prediction. arXiv preprint arXiv:2303. 03543 (pp. 1-22) (2023).
Heinen, Stefan et al. Toward the Design of Chemical Reactions: Machine Learning Barriers of Competing Mechanisms in Reactant Space. The Journal of Chemical Physics 155(6):064105 (pp. 1-10) (2021).
International Search Report and Written Opinion in International Appln. No. PCT/IB2024/056174, mailed on Oct. 28, 2024, 14 pages.
Iovanac, Nicolae C. et al. Actively Searching: Inverse Design of Novel Molecules with Simultaneously Optimized Properties. The Journal of Physical Chemistry A 126(2):333-340 (2022).
Kadan et al., "Guided Multi-Objective Generative AI to Enhance Structure-based Drug Design," CoRR, Submitted on Oct. 17, 2024, arXiv:2405.11785v2, 16 pages.

Kim, Seonghwan et al. Diffusion-Based Generative AI for Exploring Transition States From 2D Molecular Graphs. Nature Communications 15:341 (pp. 1-12) (2024).
Koes, et al. Lessons learned in empirical scoring with smina from the CSAR 2011 benchmarking exercise. J Chem Inf Model 53(8):1893-904 (2013).
Lahey, et al. Simulating protein-ligand binding with neural network potentials. Chem Sci.11 (9):2362-2368 (2020).
Lee, Myeonghun et al. MGCVAE: Multi-Objective Inverse Design via Molecular Graph Conditional Variational Autoencoder. Journal of Chemical Information and Modeling 62(12):2943-2950 (2022).
Lee, Seul et al. Exploring Chemical Space with Score-Based Out-of-Distribution Generation. Proceedings of the 40th International Conference on Machine Learning, PMLR 202:18872-18892 (2023).
Li, Yibo et al. Structure-Based De Novo Drug Design Using 3D Deep Generative Models. Chemical Science 12(41):13664-13675 (2021).
Lin, Haitao et al. DiffBP: Generative Diffusion of 3D Molecules for Target Protein Binding. arXiv preprint arXiv:2211.11214: 1-13 (2022).
Liu, Meng et al. Generating 3D Molecules for Target Protein Binding. arXiv preprint arXiv:2204.O9410:1-13 (2022).
Lugmayr, Andreas et al. RePaint: Inpainting using Denoising Diffusion Probabilistic Models Proceedings of the IEEE/CVF Conference on Computer Vision and Pattern Recognition (pp. 11461-11471) (2022).
Luo, Shitong et al. A 3D Generative Model for Structure-Based Drug Design. 35th Conference on Neural Information Processing Systems (NeurIPS) (pp. 1-11) (2021).
Luo, Shitong et al. Antigen-Specific Antibody Design and Optimization with Diffusion-Based Generative Models for Protein Structures. 36th Conference on Neural Information Processing Systems (NeurIPS) (pp. 1-14) (2022).
Masuda, Tomohide et al. Generating 3D Molecular Structures Conditional on a Receptor Binding Site with Deep Generative Models. arXiv preprint arXiv:2O10.14442 (pp. 1-13) (2020).
McNutt, et al. GNINA 1.0: molecular docking with deep learning. J Cheminform. 13(1):43 (Jun. 9, 2021).
Noh, Juhwan et al. Machine-Enabled Inverse Design of Inorganic Solid Materials: Promises and Challenges. Chemical Science 11 (19):4871-4881 (2020).
PCT/IB2O24/O5617 International Invitation to Pay Additional Fees dated Sep. 5, 2024.
Peng, Xingang et al. Pocket2Mol: Efficient Molecular Sampling Based on 3D Protein Pockets. Proceedings of the 39th International Conference on Machine Learning, PMLR 162:17644-17655 (2022).
Ragoza, et al. Generating 3D Molecules Conditional on Receptor Binding Sites with Deep Generative Models. arXiv preprint arXiv:2110. 15200 (pp. 1-16) (2021).
REAL database, 6.75B compounds. REAL database : 1-3. Retrieved on Sep. 27, 2024. Retrieved from https://enamine.neUcompound-collections/realcompounds/real-database.
Ryczko, Kevin et al. Inverse Design of a Graphene-Based Quantum Transducer via Neuroevolution. The Journal of Physical Chemistry C 124(48):26117-26123 (2020).
Sanchez-Lengeling, Benjamin et al. Optimizing Distributions Over Molecular Space. An Objective-Reinforced Generative Adversarial Network for Inverse-Design Chemistry (ORGANIC). Theoretical and Computational Chemistry, ChemRxiv (pp. 91-18) (2017).
Sauer et al., "Optimizing interactions to protein binding sites by integrating docking-scoring strategies into generative AI methods," Frontiers in Chemistry, Oct. 19, 2022, 10:1012507.
Schneuing et al., "Structure-based Drug Design with Equivariant Diffusion Models," CoRR, Submitted on Jun. 30, 2023, arXiv:2210. 13695v2, 27 pages.
Schneuing, Arne et al. Structure-Based Drug Design With Equivariant Diffusion Models. arXiv preprint arXiv:2210.13695 (pp. 1-21) (2022).
Singh, Aayush R. et al. Predicting Chemical Reaction Barriers with a Machine Learning Model. Catalysis Letters 149:2347-2354 (2019).

(56) References Cited

OTHER PUBLICATIONS

Skalic, Miha et al. From Target to Drug: Generative Modeling for the Multimodal Structure-Based Ligand Design. Molecular Pharmaceutics 16(10):4282-4291 (2019).

Skjelstad, Bastian Bjerkem, uiocompcat tmQM:2024 release. GitHub. Retrieved on Sep. 3, 2024. Retrieved from https://github.com/uiocompcat/tmqm/blob/master/README.md, 2 pages.

Smith, et al. Approaching coupled cluster accuracy with a general-purpose neural network potential through transfer learning. Nat Commun. 10(1):2903 (2019).

Smith, Justin S. et al. ANI-1: An Extensible Neural Network Potential With OFT Accuracy at Force Field Computational Cost. arXiv. [retrieved on Jul. 25, 2024]. Available at URL:https://arxiv.org/abs/1610.O8935 (pp. 1-30) (Oct. 27, 2016).

Sridharan, Bhuvanesh et al. Modern Machine Learning for Tackling Inverse Problems in Chemistry: Molecular Design to Realization. Chemical Communications 58(35):5316-5331 (2022).

Suresh et al., "Development of a Machine Learning Method to Predict Membrane Protein-Ligand Binding Residues Using Basic Sequence Information," Advances in Bioinformatics, Jan. 8, 2015, 2015(1):843030.

Trott, Oleg et al. Autodock Vina: Improving The Speed and Accuracy of Docking With a New Scoring Function, Efficient Optimization, and Multithreading. Journal of Computational Chemistry 31 (2):455-461 (2010).

Wang, et al. A fully differentiable ligand pose optimization framework guided by deep learning and traditional scoring functions. arXiv preprint arXiv:2206.13345 (pp. 1-19) (2022).

Wang, et al. Relation: A Deep Generative Model for Structure-Based De Novo Drug Design. J Med Chem. 65(13):94 78-9492 (2022).

Wang, Jia et al. Inverse Design of Materials by Machine Learning. Materials 15(5):1811 (pp. 1-19) (2022).

Xu, Mingyuan et al. De Novo Molecule Design Through the Molecular Generative Model Conditioned by 3D Information of Protein Binding Sites. Journal of Chemical Information and Modeling 61 (7):3240-3254 (2021).

Xu, Minkai et al., Geometric Latent Diffusion Models for 3D Molecule Generation, Proceedings of the 39th International Conference on Machine Learning, PMLR 202, 18 pages (2023).

Yang et al., "Deep Generation Model Guided by the Docking Score for Active Molecular Design" Journal of Chemical Information and Modeling, May 10, 2023, 63(10):2983-2991 (Abstract Only).

Zaman, Shehtab et al. STRIDE: Structure-Guided Generation for Inverse Design of Molecules. arXiv preprint arXiv:2311.O6297 (pp. 1-12) (2023).

Zhang et al., "A Simple Way to Incorporate Target Structural Information in Molecular Generative Models," Journal of Chemical Information and Modeling, Jun. 15, 2023, 63(12):3719-3730.

Zhang et al., "Application of Computational Biology and Artificial Intelligence in Drug Design," International Journal of Molecular Sciences, Nov. 5, 2022, 23(21):13568.

Zhang, et al. E3bind: An end-to-end equivariant network for protein-ligand docking. arXiv preprint arXiv:2210.06069 (pp. 1-16) (2022).

Zunger, Alex. Inverse Design In Search of Materials With Target Functionalities. Nature Reviews Chemistry 2:0121 (pp. 1-16) (2018.

200

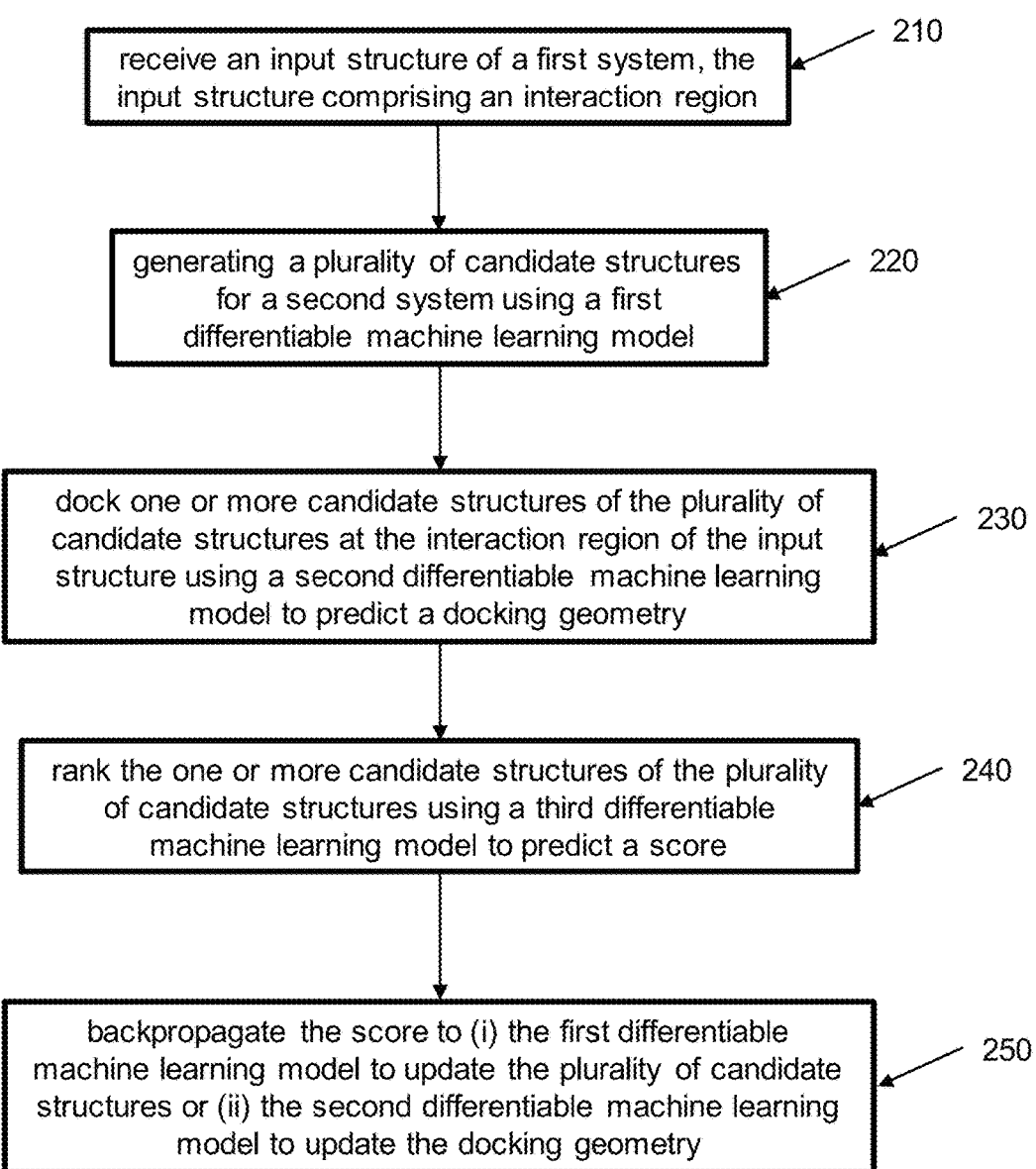

receive an input structure of a first system, the input structure comprising an interaction region — 210 generating a plurality of candidate structures for a second system using a first differentiable machine learning model — 220 dock one or more candidate structures of the plurality of candidate structures at the interaction region of the input structure using a second differentiable machine learning model to predict a docking geometry — 230 rank the one or more candidate structures of the plurality of candidate structures using a third differentiable machine learning model to predict a score — 240 backpropagate the score to (i) the first differentiable machine learning model to update the plurality of candidate structures or (ii) the second differentiable machine learning model to update the docking geometry — 250

FIG. 2

METHODS AND SYSTEMS FOR MACHINE-LEARNING BASED MOLECULE GENERATION AND SCORING

CROSS-REFERENCE

This application is a continuation of U.S. patent application Ser. No. 18/890,681, filed Sep. 19, 2024, which is a continuation of International Application No. PCT/IB2024/056174, filed Jun. 25, 2024, which claims the benefit of U.S. Provisional Application No. 63/510,422, filed Jun. 27, 2023, and U.S. Provisional Application No. 63/648,851, filed May 17, 2024, each of which is incorporated herein by reference in its entirety.

BACKGROUND

Computational chemistry has become an established tool for the molecular and material discovery process in many areas of industry. Computational chemistry can provide accurate prediction of chemical phenomena and examination of molecular properties that may be inaccessible solely from the experiment and/or requires significant labor. In an example application, computer-aided drug discovery (CADD) has the potential to be a faster and less expensive approach compared to an laboratory-based drug discovery process.

Structure-based drug design (SBDD) paradigms can involve designing ligands with high binding affinities for a given a 3-dimensional protein pocket. SBDD can involve finding a solution to an inverse design problem, where the desired properties (e.g., high binding affinity to a target protein, synthesizability etc.) are known, but the design of a molecule with the desired properties is non-trivial. SBDD can comprise two steps. One step can be the sampling of a chemical space, and the other step can be scoring (or evaluating) sampled compounds' ability to satisfy the set of desired properties.

The sampling of chemical space can be performed in various ways. For drug discovery, for example, this can be performed by evaluating each entry of a large database of molecules (such as ZINC, Enamine, or GDB) and collecting the results and ranking them to yield a shortlist of compounds to be screened in a laboratory. Although these databases can contain hundreds of billions of molecules, billions is still a very small fraction of the drug-like chemical space which is estimated to number anywhere between $10^{20}$ to $10^{60}$ molecules.

SUMMARY

Computer-aided design can accelerate drug discovery. Recent advances in scalable computing and generative chemistry have led to deep learning models that access uncharted chemical space for creating novel drug compounds. However, existing models may be limited in designing molecules that satisfy multiple desired physicochemical properties.

In an aspect, the present disclosure provides, a method that combines generative modeling (e.g., a diffusion model) with multi-objective optimization. In some embodiments, the latent variables of a generative model are guided to generate ligands while optimizing for a plurality of target properties. In some embodiments, the plurality of target properties can comprise affinity (e.g., binding affinity to a protein molecule of interest) and synthetic accessibility.

In a CADD method, the larger the chemical space that is explored, the higher the chances are to discover better materials. However, considering that synthesizable chemical space is estimated to be $10^{180}$, the scale of the problem is massive in terms of both time and computational cost. To expand the search chemical space for CADD, machine learning (ML) approaches may be used to perform this exploration while managing computational cost.

In an aspect, the present disclosure provides, a method for machine learning aided modeling of two interacting structures, the method comprising: (a) receiving an input structure comprising an interaction region; (b) generating a plurality of candidate structures using a first differentiable machine learning model; (c) docking one or more candidate structures of the plurality of candidate structures at the interaction region of the input structure using a second differentiable machine learning model to predict a docking geometry; (d) ranking the one or more candidate structures of the plurality of candidate structures docked in (c) using a third differentiable machine learning model or differentiable scoring function to predict a score; and (e) propagating the score to (i) the first differentiable machine learning model to update the plurality of candidate structures or (ii) the second differentiable machine learning model to update the docking geometry.

In some embodiments, the method further comprises outputting a list of the plurality of candidates updated in (e). In some embodiments, the input structure is a host molecule and wherein the plurality of candidate structures comprises a guest molecule. In some embodiments, the input structure is a macromolecule or a biomolecule, wherein the plurality of candidate structures comprises a ligand, and wherein the interaction region is an active site. In some embodiments, the macromolecule or the biomolecule is a protein. In some embodiments, the protein is an enzyme. In some embodiments, the macromolecule or the biomolecule is a protein and wherein the ligand is selected from the group consisting of another protein, a neurotransmitter, a toxin, a neuropeptide, and a steroid. In some embodiments, the macromolecule or the biomolecule is a protein and wherein the ligand is an active pharmaceutical compound. In some embodiments, the macromolecule is a metal-organic framework. In some embodiments, the macromolecule is a polymer. In some embodiments, the input structure is a catalyst.

In some embodiments, the third machine learning model is the second machine learning model, and wherein the score comprises a confidence estimate for the one or more candidate structures docked in (c). In some embodiments, the confidence estimate is a prediction of the root mean squared distance between a candidate structure and a ground-truth structure. In some embodiments, the ground-truth structure is an experimentally determined structure.

In some embodiments, the second machine learning model is the first machine learning model, and wherein the generating comprises generating directly into the interaction region of the input structure. In some embodiments, the interaction region is determined by the second machine learning model. In some embodiments, the interaction region is determined by a fourth machine learning model.

In some embodiments, the score comprises an indication of a binding affinity, a volume of a molecule, a dipole moment, or an interaction energy between the input structure and the plurality of candidate structures. In some embodiments, (d) comprises generating a scoring function, wherein the scoring function is differentiable. In some embodiments, (b) comprises exploring a chemical space using one or more metrics selected from the group consisting of synthesizability, uniqueness, novelty, and diversity of proposals.

In some embodiments, the first differentiable machine learning model is a generative model. In some embodiments, the generative model is a diffusion-based or a transformer-based generative model. In some embodiments, the diffusion-based generative model is a denoising diffusion probabilistic model. In some embodiments, the first differentiable machine learning model is a deep learning model. In some embodiments, the first differentiable machine learning model comprises one or more models selected from the group consisting of DiffSBDD, LiGAN, DeepLigBuilder, geoLDM, and RELATION. In some embodiments, the input structure, the plurality of candidate structures, or both are represented as SMILES structures. In some embodiments, the docking geometry comprises a predicted pose of a candidate structure with respect to the input structure.

In some embodiments, the second differentiable machine learning model is a generative model. In some embodiments, the generative model is a diffusion-based or a transformer-based generative model. In some embodiments, the second differentiable machine learning model comprises one or more models selected from the group consisting of DiffDock, GNINA, E3BIND. In some embodiments, the third differentiable machine learning model or differentiable scoring function comprises one or more models from the group consisting of ANI, Vina, Vinardo, Smina. In some embodiments, (e) comprises using the first differentiable machine learning model to generate additional candidate structures, wherein the additional candidate structures are not in the plurality of candidate structures in (b). In some embodiments, (e) comprises backpropagating gradient information. In some embodiments, (e) comprises forward propagating gradient information.

In some embodiments, the method further comprises estimating an inference reliability from at least one of differentiable machine learning models. In some embodiments, the method further comprises determining that the inference reliability is less than a threshold, and recalculating an output of the at least one differentiable model using an underlying differentiable method on which the at least one of the differentiable machine learning models is trained or another differentiable method. In some embodiments, the method further comprises retraining the differentiable machine learning model based at least in part on an output from the underlying differentiable machine learning model and a gradient of the underlying differentiable machine learning model to improve the inference reliability.

In an aspect, the present disclosure provides, a system for machine learning aided modeling of two interacting structures, the system comprising a non-transitory computer-readable medium with instructions stored thereon which when executed by a processor are configured to: (a) receive an input structure comprising an interaction region; (b) generate a plurality of candidate structures using a first differentiable machine learning model; (c) dock one or more candidate structures of the plurality of candidate structures at the interaction region of the input structure using a second differentiable machine learning model to predict a docking geometry; (d) rank the one or more candidate structures of the plurality of candidate structures docked in (c) using a third differentiable machine learning model or a differentiable scoring function to predict a score; and (e) propagate the score to (i) the first differentiable machine learning model to update the plurality of candidate structures or (ii) the second differentiable machine learning model to update the docking geometry.

In some embodiments, the processor is further configured to output a list of the plurality of candidates updated in (e). In some embodiments, the input structure is a host molecule and wherein the plurality of candidate structures comprises a guest molecule. In some embodiments, the input structure is a macromolecule or a biomolecule, wherein the plurality of candidate structures comprises a ligand, and wherein the interaction region is an active site. In some embodiments, the macromolecule or the biomolecule is a protein. In some embodiments, the protein is an enzyme. In some embodiments, the macromolecule or the biomolecule is a protein and wherein the ligand is selected from the group consisting of another protein, a neurotransmitter, a toxin, a neuropeptide, and a steroid. In some embodiments, the macromolecule or the biomolecule is a protein and wherein the ligand is an active pharmaceutical compound. In some embodiments, the macromolecule is a metal-organic framework. In some embodiments, the macromolecule is a polymer. In some embodiments, the input structure is a catalyst.

In some embodiments, the third machine learning model is the second machine learning model, and wherein the score comprises a confidence estimate for the one or more candidate structures docked in (c). In some embodiments, the confidence estimate is a prediction of the root mean squared distance between a candidate structure and a ground truth structure. In some embodiments, the ground-truth structure is an experimentally determined structure.

In some embodiments, the second machine learning model is the first machine learning model, and wherein the generating comprises generating directly into the interaction region of the input structure. In some embodiments, the interaction region is determined by the second machine learning model. In some embodiments, the interaction region is determined by a fourth machine learning model. In some embodiments, the score comprises an indication of a binding affinity, a volume of a molecule, a dipole moment, or an interaction energy between the input structure and the plurality of candidate structures.

In some embodiments, at (d) the processor is further configured to generate a scoring function, wherein the scoring function is differentiable. In some embodiments, at (b) the processor is further configured to explore a chemical space using one or more metrics selected from the group consisting of synthesizability, uniqueness, novelty, and diversity of proposals.

In some embodiments, the first differentiable machine learning model is a generative model. In some embodiments, the generative model is a diffusion-based or a transformer-based generative model. In some embodiments, the diffusion-based generative model is a denoising diffusion probabilistic model. In some embodiments, the first differentiable machine learning model is a deep learning model. In some embodiments, the first differentiable machine learning model comprises one or more models selected from the group consisting of DiffSBDD, LiGAN, DeepLigBuilder, geoLDM, and RELATION. In some embodiments, the input structure, the plurality of candidate structures, or both are represented as SMILES strings. In some embodiments, the docking geometry comprises a predicted pose of the candidate structure with respect to the input structure.

In some embodiments, the second differentiable machine learning model is a generative model. In some embodiments, the generative model is a diffusion-based or a transformer-based generative model. In some embodiments, the second differentiable machine learning model comprises one or more models selected from the group consisting of DiffDock, GNINA, E3BIND, and TANKBind. In some embodiments, the third differentiable machine learning model or differentiable scoring function comprises one or more models from the group consisting of ANI, Vina, Vinardo, Smina.

In some embodiments, at (b) the processor is further configured to use the first differentiable machine learning model to generate additional candidate structures, wherein the additional candidate structures are not in the plurality of candidate structures in (b). In some embodiments, at (e) the processor is further configured to backpropagate gradient information. In some embodiments, at (e) the processor is further configured to forward propagate gradient information.

In some embodiments, the processor is further configured to estimate an inference reliability from at least one of differentiable machine learning models. In some embodiments, the processor is further configured to determine that the inference reliability is less than a threshold, and recalculate an output of the at least one differentiable model using an underlying differentiable method on which the at least one of the differentiable machine learning models is trained or another differentiable method. In some embodiments, the processor is further configured to retrain the differentiable machine learning model based at least in part on an output from the underlying differentiable machine learning model and a gradient of the underlying differentiable machine learning model to improve the inference reliability.

In an aspect, the present disclosure provides, a system for machine learning aided modeling of two interacting structures, the system comprising: (a) an indication of an input structure comprising an interaction region; (b) a first differentiable machine learning model configured to generate a plurality of candidate structures; (c) a second differentiable machine learning model configured to dock one or more candidate structures of the plurality of candidate structures at the interaction region of the input structure to predict a docking geometry; (d) a third differentiable machine learning model configured to rank the one or more candidate structures of the plurality of candidate structures docked by the second differentiable machine learning model to predict a score; and (e) an indication of an updated docking geometry, wherein the updated docking geometry is generated at least in part on a backpropagation of the score to (i) the first differentiable machine learning model to update the plurality of candidate structures or (ii) the second differentiable machine learning model.

In an aspect, the present disclosure provides, a method of optimizing reference compounds, comprising: (a) obtaining a target structure and a first ligand structure; (b) generating a latent vector based on the first ligand structure; (c) processing the latent vector, with or without SE(3) equivariance or other symmetries, to generate a second ligand structure based on (i) the target structure and (ii) a score comprising a measure of affinity between the target structure and the second ligand structure, wherein the score is differentiable with respect to a definition comprising particle positions or atom types; and (d) generating a report comprising an identifier for the second ligand structure.

In some embodiments, the target structure is generated using a machine learning model. In some embodiments, an interaction region of the target structure is generated using a machine learning model. In some embodiments, the machine learning model further generates the second ligand structure. In some embodiments, the first ligand structure is a hit compound or a lead compound. In some embodiments, the first ligand structure is configured to interact with the target structure. In some embodiments, the first ligand structure is configured to bind to the target structure. In some embodiments, the second ligand structure is a lead compound or a lead-optimized compound. In some embodiments, the second ligand structure is configured to interact with the target structure. In some embodiments, the second ligand structure is configured to bind to the target structure. In some embodiments, the target structure is a protein structure. In some embodiments, the target structure comprises an interaction region. In some embodiments, the interaction region comprises a protein pocket. In some embodiments, the first ligand structure is a small molecule, a nucleic acid, a peptide, or a protein.

In some embodiments, the latent vector is a noisy latent vector. In some embodiments, the generating in (b) comprises noising an initial latent vector of the first ligand structure. In some embodiments, the noising comprises diffusing the initial latent vector of the first ligand structure. In some embodiments, the noising comprises stochastic noising. In some embodiments, the processing in (c) comprises denoising the latent vector. In some embodiments, the denoising comprises reverse diffusing the latent vector or a noisy ligand structure thereof.

In some embodiments, the processing in (c) is performed using a neural network. In some embodiments, the neural network is a diffusion model. In some embodiments, the target structure is fixed during the denoising. In some embodiments, the target structure is movable during the denoising. In some embodiments, the measure of affinity is a measure of binding affinity. In some embodiments, the measure of affinity accounts for a potential energy of the target structure and the ligand structure. In some embodiments, the measure of affinity accounts for a free energy of the target structure and the ligand structure. In some embodiments, the particle positions comprise atom positions, coarse-grained particle positions, residue positions, or any combination thereof. In some embodiments, the particle positions comprise coordinates. In some embodiments, the measure of affinity is based on a force-field, a quantum chemical calculation, or a free energy perturbation calculation.

In some embodiments, the processing in (c) is further based on a measure of synthetic accessibility of the second ligand structure. In some embodiments, the measure of synthetic accessibility is based on or not based on an equivariant neural network. In some embodiments, the processing in (c) is further based on a measure of feasibility that is based on an equivariant neural network. In some embodiments, the processing in (c) is further based on a measure of feasibility that is differentiable with respect to a definition comprising particle positions or atom types. In some embodiments, the measure of feasibility comprises measure of absorption, distribution, metabolism, and excretion-toxicity (ADMET). In some embodiments, the method further comprises synthesizing the second ligand structure. In some embodiments, the method further comprises performing a binding assay to detect a binding event between the target structure and the second ligand structure. In some embodiments, the method further comprises performing the method using the second ligand structure as the first ligand structure. In some embodiments, the target structure is a host molecule and wherein the second ligand structure is a guest molecule. In some embodiments, the target structure is a macromolecule or a biomolecule, and wherein the interaction region is an active site. In some embodiments, the macromolecule or the biomolecule is a protein. In some embodiments, the protein is an enzyme. In some embodiments, the macromolecule or the biomolecule is a protein and wherein the ligand structure is selected from the group consisting of another protein, a neurotransmitter, a toxin, a neuropeptide, and a steroid. In some embodiments, the macromolecule or the biomolecule is a protein and wherein the ligand structure is an active pharmaceutical compound. In some embodiments, the macromolecule is a metal-organic framework. In some embodiments, the macromolecule is a polymer. In some embodiments, the target structure is a catalyst.

In an aspect, the present disclosure provides, a method of generating lead compounds, comprising: (a) obtaining a target structure and a latent vector; (b) processing the latent vector to generate an intermediate latent vector; (c) processing the intermediate latent vector to generate a ligand structure; and (d) generating a report comprising an identifier for the ligand structure; wherein the processing in (b) and (c) are performed with or without SE(3) equivariance or other symmetries and are based on (i) the target structure and (ii) a measure of affinity between the target structure and the ligand structure, wherein the measure of binding affinity is differentiable with respect to a definition comprising particle positions or atom types.

In some embodiments, the latent vector is a random latent vector. In some embodiments, the intermediate latent vector corresponds to a noisy ligand structure. In some embodiments, the processing in (c) is performed a plurality of times to generate a plurality of ligand structures. In some embodiments, a gradient of the measure of affinity is propagatable to the intermediate latent vector. In some embodiments, the processing in (b) and (c) are based on a measure of synthesizability of the ligand structure. In some embodiments, a gradient of the measure of synthesizability is propagatable to the intermediate latent vector.

In some embodiments, the target structure is generated using a machine learning model. In some embodiments, an interaction region of the target structure is generated using a machine learning model. In some embodiments, the latent vector is generated using a machine learning model. In some embodiments, the ligand structure is configured to interact with the target structure. In some embodiments, the ligand structure is configured to bind to the target structure. In some embodiments, the target structure is a protein structure. In some embodiments, the target structure comprises an interaction region. In some embodiments, the interaction region comprises a protein pocket. In some embodiments, the ligand structure is a small molecule, a nucleic acid, a peptide, or a protein.

In some embodiments, the processing in (b) comprises denoising the latent vector. In some embodiments, the denoising comprises reverse diffusing the latent vector. In some embodiments, the processing in (b) is performed using a neural network. In some embodiments, the neural network is a diffusion model. In some embodiments, the target structure is fixed during the denoising. In some embodiments, the target structure is movable during the denoising. In some embodiments, the measure of affinity is a measure of binding affinity. In some embodiments, the measure of affinity accounts for a potential energy of the target structure and the ligand structure. In some embodiments, the measure of affinity accounts for a free energy of the target structure and the ligand structure. In some embodiments, the particle positions comprise atom positions, coarse-grained particle positions, residue positions, or any combination thereof. In some embodiments, the particle positions comprise coordinates. In some embodiments, the measure of affinity is based on a force-field, a quantum chemical calculation, or a free energy perturbation calculation. In some embodiments, the processing in (b) and (c) are further based on a measure of synthetic accessibility of the ligand structure. In some embodiments, the measure of synthetic accessibility is based on or not on an equivariant neural network. In some embodiments, the processing in (b) is further based on a measure of feasibility that is based on an equivariant neural network. In some embodiments, the processing in (b) is further based on a measure of feasibility that is differentiable with respect to a definition comprising particle positions or atom types. In some embodiments, the measure of feasibility comprises measure of absorption, distribution, metabolism, and excretion-toxicity (ADMET).

In some embodiments, the method further comprises synthesizing the ligand structure. In some embodiments, the method further comprises performing a binding assay to detect a binding event between the target structure and the ligand structure.

In some embodiments, the method further comprises performing the method using the ligand structure to generate the latent vector. In some embodiments, the target structure is a host molecule and wherein the ligand structure is a guest molecule. In some embodiments, the target structure is a macromolecule or a biomolecule, and wherein the interaction region is an active site. In some embodiments, the macromolecule or the biomolecule is a protein. In some embodiments, the protein is an enzyme. In some embodiments, the macromolecule or the biomolecule is a protein and wherein the ligand structure is selected from the group consisting of another protein, a neurotransmitter, a toxin, a neuropeptide, and a steroid. In some embodiments, the macromolecule or the biomolecule is a protein and wherein the ligand structure is an active pharmaceutical compound. In some embodiments, the macromolecule is a metal-organic framework. In some embodiments, the macromolecule is a polymer. In some embodiments, the target structure is a catalyst.

In an aspect, the present disclosure provides, a computer program product comprising a computer-readable medium having computer-executable code encoded therein, the computer-executable code adapted to be executed to implement a method disclosure herein. In some embodiments, the computer-executable code is callable through an active programming interface.

In an aspect, the present disclosure provides, a non-transitory computer-readable storage media encoded with a computer program including instructions executable by one or more processors to implement a method disclosure herein. In some embodiments, the instructions are callable through an active programming interface.

In an aspect, the present disclosure provides, a computer-implemented system comprising: a digital processing device comprising: at least one processor, an operating system configured to perform executable instructions, a memory, and a computer program including instructions executable by the digital processing device to perform a method disclosure herein. In some embodiments, the computer-implemented system is callable through an active programming interface.

In an aspect, the present disclosure provides, a processor comprising a communications interface configured to connect to a computing system over a network, the processor configured to: (a) receive an indication of a problem from a user comprising a target structure and a first ligand structure; (b) direct instructions via the communications interface to generate a latent vector based on the first ligand structure, wherein the computing system is configured to process the latent vector, with or without SE(3) equivariance or other symmetries, to generate a second ligand structure based on (i) the target structure and (ii) a score comprising a measure of affinity between the target structure and the second ligand structure, wherein the score is differentiable with respect to a definition comprising particle positions or atom types; and (c) receive an output via the communications interface, the output comprising a report comprising an identifier for the second ligand structure.

In an aspect, the present disclosure provides, a processor comprising a communications interface configured to connect to a control system over a network, the processor configured to: (a) receive instructions via the communications interface, the instructions comprising an indication of a problem comprising a target structure and a first ligand structure from a control system; (a) implement instructions to: (i) generate a latent vector based on the first ligand structure; and (ii) process the latent vector, with or without SE(3) equivariance or other symmetries, to generate a second ligand structure based on (i) the target structure and (ii) a score comprising a measure of affinity between the target structure and the second ligand structure, wherein the score is differentiable with respect to a definition comprising particle positions or atom types; and (b) direct an output to via the communications interface, the output comprising a report comprising an identifier for the second ligand structure.

In an aspect, the present disclosure provides, a processor comprising a communications interface configured to connect to a computing system over a network, the processor configured to: (a) receive an indication of a problem from a user comprising a target structure and a latent vector; (b) direct instructions via the communications interface to process the latent vector to generate an intermediate latent vector and to process the intermediate latent vector to generate a ligand structure, wherein the computing system is configured to perform the processing, with or without SE(3) equivariance or other symmetries, based on (i) the target structure and (ii) a measure of affinity between the target structure and the ligand structure, wherein the measure of binding affinity is differentiable with respect to a definition comprising particle positions or atom types; and (c) receive an output via the communications interface, the output comprising a report comprising an identifier for the ligand structure.

In an aspect, the present disclosure provides, a processor comprising a communications interface configured to connect to a control system over a network, the processor configured to: (a) receive instructions via the communications interface, the instructions comprising an indication of a problem comprising a target structure and a latent vector from a control system; (b) implement instructions to process the latent vector to generate an intermediate latent vector and to process the intermediate latent vector to generate a ligand structure, with or without SE(3) equivariance or other symmetries, based on (i) the target structure and (ii) a measure of affinity between the target structure and the ligand structure, wherein the measure of binding affinity is differentiable with respect to a definition comprising particle positions or atom types; and (c) direct an output to via the communications interface, the output comprising a report comprising an identifier for the ligand structure.

In an aspect, the present disclosure provides, a method for machine learning aided modeling of a structure, the method comprising: (a) generating a plurality of candidate structures using a first differentiable machine learning model; (b) predicting one or more geometries of one or more candidate structures of the plurality of candidate structures using a second differentiable machine learning model; (c) ranking the one or more candidate structures of the plurality of candidate structures using a third differentiable machine learning model or differentiable scoring function to predict a score; and (d) propagating the score to (i) the first differentiable machine learning model to update the plurality of candidate structures or (ii) the second differentiable machine learning model to update the one or more geometries.

In some embodiments, the method further comprises outputting a list of the plurality of candidates updated in (d). In some embodiments, the plurality of candidate structures is provided in an environment, wherein the environment is vacuum, a gas phase media, a solvent media, or a solid surface. In some embodiments, the plurality of candidate structures comprises a macromolecule, a biomolecule, or a ligand. In some embodiments, the macromolecule or the biomolecule is a protein. In some embodiments, the protein is an enzyme. In some embodiments, the ligand is selected from the group consisting of another protein, a neurotransmitter, a toxin, a neuropeptide, and a steroid. In some embodiments, the ligand is an active pharmaceutical compound. In some embodiments, the macromolecule is a metal-organic framework. In some embodiments, the macromolecule is a polymer.

In some embodiments, the third machine learning model is the second machine learning model, and wherein the score comprises a confidence estimate for the one or more geometries of the one or more candidate structures. In some embodiments, the confidence estimate is a prediction of the root mean squared distance between a candidate structure and a ground-truth structure. In some embodiments, the ground-truth structure is an experimentally determined structure. In some embodiments, the second machine learning model is the first machine learning model. In some embodiments, the score comprises an indication of a binding affinity, a volume of a molecule, or a dipole moment. In some embodiments, (c) comprises generating a scoring function, wherein the scoring function is differentiable. In some embodiments, (a) comprises exploring a chemical space using one or more metrics selected from the group consisting of synthesizability, uniqueness, novelty, and diversity of proposals.

In some embodiments, the first differentiable machine learning model is a generative model. In some embodiments, the generative model is a diffusion-based or a transformer-based generative model. In some embodiments, the diffusion-based generative model is a denoising diffusion probabilistic model. In some embodiments, the first differentiable machine learning model is a deep learning model. In some embodiments, the first differentiable machine learning model comprises one or more models selected from the group consisting of DiffSBDD, LiGAN, DeepLigBuilder, geoLDM, and RELATION. In some embodiments, the plurality of candidate structures are represented as SMILES structures. In some embodiments, the second differentiable machine learning model is a generative model. In some embodiments, the generative model is a diffusion-based or a transformer-based generative model. In some embodiments, the second differentiable machine learning model comprises one or more models selected from the group consisting of DiffDock, GNINA, E3BIND. In some embodiments, the third differentiable machine learning model or differentiable scoring function comprises one or more models from the group consisting of ANI, Vina, Vinardo, Smina.

In some embodiments, (d) comprises using the first differentiable machine learning model to generate additional candidate structures, wherein the additional candidate structures are not in the plurality of candidate structures in (a). In some embodiments, (d) comprises backpropagating gradient information. In some embodiments, (d) comprises forward propagating gradient information.

In some embodiments, the method further comprises estimating an inference reliability from at least one of differentiable machine learning models. In some embodiments, the method further comprises determining that the inference reliability is less than a threshold, and recalculating an output of the at least one differentiable model using an underlying differentiable method on which the at least one of the differentiable machine learning models is trained or another differentiable method. In some embodiments, the method further comprises retraining the differentiable machine learning model based at least in part on an output from the underlying differentiable machine learning model and a gradient of the underlying differentiable machine learning model to improve the inference reliability.

In an aspect, the present disclosure provides, a system for machine learning aided modeling of a structure, the system comprising a non-transitory computer-readable medium with instructions stored thereon which when executed by a processor are configured to: (a) generate a plurality of candidate structures using a first differentiable machine learning model; (b) predict one or more geometries of one or more candidate structures of the plurality of candidate structures using a second differentiable machine learning model; (c) rank the one or more candidate structures of the plurality of candidate structures in (c) using a third differentiable machine learning model or a differentiable scoring function to predict a score; and (d) propagate the score to (i) the first differentiable machine learning model to update the plurality of candidate structures or (ii) the second differentiable machine learning model to update the one or more geometries.

In some embodiments, the processor is further configured to output a list of the plurality of candidates updated in (d). In some embodiments, the plurality of candidate structures is provided in an environment, wherein the environment is vacuum, a gas phase media, a solvent media, or a solid surface. In some embodiments, the plurality of candidate structures comprises a macromolecule, a biomolecule, or a ligand. In some embodiments, the macromolecule or the biomolecule is a protein. In some embodiments, the protein is an enzyme. In some embodiments, the ligand is selected from the group consisting of another protein, a neurotransmitter, a toxin, a neuropeptide, and a steroid. In some embodiments, the ligand is an active pharmaceutical compound. In some embodiments, the macromolecule is a metal-organic framework. In some embodiments, the macromolecule is a polymer.

In some embodiments, the third machine learning model is the second machine learning model, and wherein the score comprises a confidence estimate for the one or more candidate structures docked in (c). In some embodiments, the confidence estimate is a prediction of the root mean squared distance between a candidate structure and a ground truth structure. In some embodiments, the ground-truth structure is an experimentally determined structure. In some embodiments, the second machine learning model is the first machine learning model. In some embodiments, the score comprises an indication of a binding affinity, a volume of a molecule, or a dipole moment. In some embodiments, at (c) the processor is further configured to generate a scoring function, wherein the scoring function is differentiable. In some embodiments, at (a) the processor is further configured to explore a chemical space using one or more metrics selected from the group consisting of synthesizability, uniqueness, novelty, and diversity of proposals. In some embodiments, the first differentiable machine learning model is a generative model. In some embodiments, the generative model is a diffusion-based or a transformer-based generative model. In some embodiments, the diffusion-based generative model is a denoising diffusion probabilistic model. In some embodiments, the first differentiable machine learning model is a deep learning model. In some embodiments, the first differentiable machine learning model comprises one or more models selected from the group consisting of DiffSBDD, LiGAN, DeepLigBuilder, geoLDM, and RELATION.

In some embodiments, the plurality of candidate structures are represented as SMILES strings. In some embodiments, the second differentiable machine learning model is a generative model. In some embodiments, the generative model is a diffusion-based or a transformer-based generative model. In some embodiments, the second differentiable machine learning model comprises one or more models selected from the group consisting of DiffDock, GNINA, E3BIND, and TANKBind. In some embodiments, the third differentiable machine learning model or differentiable scoring function comprises one or more models from the group consisting of ANI, Vina, Vinardo, Smina.

In some embodiments, at (d) the processor is further configured to use the first differentiable machine learning model to generate additional candidate structures, wherein the additional candidate structures are not in the plurality of candidate structures in (a). In some embodiments, at (d) the processor is further configured to backpropagate gradient information. In some embodiments, at (d) the processor is further configured to forward propagate gradient information.

In some embodiments, the processor is further configured to estimate an inference reliability from at least one of differentiable machine learning models. In some embodiments, the processor is further configured to determine that the inference reliability is less than a threshold, and recalculate an output of the at least one differentiable model using an underlying differentiable method on which the at least one of the differentiable machine learning models is trained or another differentiable method. In some embodiments, the processor is further configured to retrain the differentiable machine learning model based at least in part on an output from the underlying differentiable machine learning model and a gradient of the underlying differentiable machine learning model to improve the inference reliability.

In an aspect, the present disclosure provides, a system for machine learning aided modeling of a structure, the system comprising: (a) a first differentiable machine learning model configured to generate a plurality of candidate structures; (b) a second differentiable machine learning model configured to predict one or more geometries of one or more candidate structures of the plurality of candidate structures using a second differentiable machine learning model; (c) a third differentiable machine learning model configured to rank the one or more candidate structures of the plurality of candidate structures in (c) to predict a score; and (d) an indication of an updated geometry, wherein the updated geometry is generated at least in part on a propagation of the score to (i) the first differentiable machine learning model to update the plurality of candidate structures or (ii) the second differentiable machine learning model to update the one or more geometries.

In an aspect, the present disclosure provides, a method of optimizing reference compounds, comprising: (a) obtaining a first ligand structure; (b) generating a latent vector based on the first ligand structure; (c) processing the latent vector, with or without SE(3) equivariance or other symmetries, to generate a second ligand structure based on a score that is differentiable with respect to a definition comprising particle positions or atom types; and (d) generating a report comprising an identifier for the second ligand structure.

In some embodiments, a machine learning model generates the second ligand structure. In some embodiments, the first ligand structure is a hit compound or a lead compound. In some embodiments, the second ligand structure is a lead compound or a lead-optimized compound. In some embodiments, the first ligand structure is a small molecule, a nucleic acid, a peptide, or a protein. In some embodiments, the latent vector is a noisy latent vector.

In some embodiments, the generating in (b) comprises noising an initial latent vector of the first ligand structure. In some embodiments, the noising comprises diffusing the initial latent vector of the first ligand structure. In some embodiments, the noising comprises stochastic noising. In some embodiments, the processing in (c) comprises denoising the latent vector. In some embodiments, the denoising comprises reverse diffusing the latent vector or a noisy ligand structure thereof.

In some embodiments, the processing in (c) is performed using a neural network. In some embodiments, the neural network is a diffusion model. In some embodiments, the particle positions comprise atom positions, coarse-grained particle positions, residue positions, or any combination thereof. In some embodiments, the particle positions comprise coordinates.

In some embodiments, the processing in (c) is further based on a measure of synthetic accessibility of the second ligand structure. In some embodiments, the measure of synthetic accessibility is based on or not based on an equivariant neural network. In some embodiments, the processing in (c) is further based on a measure of feasibility that is based on an equivariant neural network. In some embodiments, the processing in (c) is further based on a measure of feasibility that is differentiable with respect to a definition comprising particle positions or atom types. In some embodiments, the measure of feasibility comprises measure of absorption, distribution, metabolism, and excretion-toxicity (ADMET). In some embodiments, the method further comprises synthesizing the second ligand structure. In some embodiments, the method further comprises performing the method using the second ligand structure as the first ligand structure. In some embodiments, the first ligand structure is provided in an environment, and wherein the environment is vacuum, a gas phase media, a solvent media, or a solid surface.

In an aspect, the present disclosure provides, a method of generating lead compounds, comprising: (a) obtaining a latent vector; (b) processing the latent vector to generate an intermediate latent vector; (c) processing the intermediate latent vector to generate a ligand structure; and (d) generating a report comprising an identifier for the ligand structure; wherein the processing in (b) and (c) are performed with or without SE(3) equivariance or other symmetries and are based on a score that is differentiable with respect to a definition comprising particle positions or atom types.

In some embodiments, the latent vector is a random latent vector. In some embodiments, the intermediate latent vector corresponds to a noisy ligand structure. In some embodiments, wherein the processing in (c) is performed a plurality of times to generate a plurality of ligand structures. In some embodiments, a gradient of the measure of affinity is propagatable to the intermediate latent vector. In some embodiments, the processing in (b) and (c) are based on a measure of synthesizability of the ligand structure. In some embodiments, a gradient of the measure of synthesizability is propagatable to the intermediate latent vector.

In some embodiments, the latent vector is generated using a machine learning model. In some embodiments, the ligand structure is a small molecule, a nucleic acid, a peptide, or a protein. In some embodiments, the processing in (b) comprises denoising the latent vector. In some embodiments, the denoising comprises reverse diffusing the latent vector. In some embodiments, the processing in (b) is performed using a neural network. In some embodiments, the neural network is a diffusion model. In some embodiments, the particle positions comprise atom positions, coarse-grained particle positions, residue positions, or any combination thereof. In some embodiments, the particle positions comprise coordinates. In some embodiments, the measure of affinity is based on a force-field, a quantum chemical calculation, or a free energy perturbation calculation. In some embodiments, the processing in (b) and (c) are further based on a measure of synthetic accessibility of the ligand structure. In some embodiments, the measure of synthetic accessibility is based on or not on an equivariant neural network. In some embodiments, the processing in (b) is further based on a measure of feasibility that is based on an equivariant neural network. In some embodiments, the processing in (b) is further based on a measure of feasibility that is differentiable with respect to a definition comprising particle positions or atom types. In some embodiments, the measure of feasibility comprises measure of absorption, distribution, metabolism, and excretion-toxicity (ADMET). In some embodiments, the method further comprises synthesizing the ligand structure. In some embodiments, the method further comprises performing the method using the ligand structure to generate the latent vector.

In an aspect, the present disclosure provides, a computer program product comprising a computer-readable medium having computer-executable code encoded therein, the computer-executable code adapted to be executed to implement a method disclosed herein. In some embodiments, the computer-executable code is callable through an active programming interface.

In an aspect, the present disclosure provides, a non-transitory computer-readable storage media encoded with a computer program including instructions executable by one or more processors to implement a method disclosed herein. In some embodiments, the instructions are callable through an active programming interface.

In an aspect, the present disclosure provides, a computer-implemented system comprising: a digital processing device comprising: at least one processor, an operating system configured to perform executable instructions, a memory, and a computer program including instructions executable by the digital processing device to perform a method disclosed herein. In some embodiments, the computer-implemented system is callable through an active programming interface.

In an aspect, the present disclosure provides, a processor comprising a communications interface configured to connect to a computing system over a network, the processor configured to: (a) receive an indication of a problem from a user comprising a first ligand structure; (b) direct instructions via the communications interface to generate a latent vector based on the first ligand structure, wherein the computing system is configured to process the latent vector, with or without SE(3) equivariance or other symmetries, to generate a second ligand structure based on a score comprising that is differentiable with respect to a definition comprising particle positions or atom types; and (c) receive an output via the communications interface, the output comprising a report comprising an identifier for the second ligand structure.

In an aspect, the present disclosure provides, a processor comprising a communications interface configured to connect to a control system over a network, the processor configured to: (a) receive instructions via the communications interface, the instructions comprising an indication of a problem comprising a first ligand structure from a control system; (b) implement instructions to: (i) generate a latent vector based on the first ligand structure; and (ii) process the latent vector, with or without SE(3) equivariance or other symmetries, to generate a second ligand structure based on a score that is differentiable with respect to a definition comprising particle positions or atom types; and (c) direct an output to via the communications interface, the output comprising a report comprising an identifier for the second ligand structure.

In an aspect, the present disclosure provides, a processor comprising a communications interface configured to connect to a computing system over a network, the processor configured to: (a) receive an indication of a problem from a user comprising a latent vector; (b) direct instructions via the communications interface to process the latent vector to generate an intermediate latent vector and to process the intermediate latent vector to generate a ligand structure, wherein the computing system is configured to perform the processing, with or without SE(3) equivariance or other symmetries, based on a score that is differentiable with respect to a definition comprising particle positions or atom types; and (c) receive an output via the communications interface, the output comprising a report comprising an identifier for the ligand structure.

In an aspect, the present disclosure provides, a processor comprising a communications interface configured to connect to a control system over a network, the processor configured to: (a) receive instructions via the communications interface, the instructions comprising an indication of a problem comprising a latent vector from a control system; (b) implement instructions to process the latent vector to generate an intermediate latent vector and to process the intermediate latent vector to generate a ligand structure, with or without SE(3) equivariance or other symmetries, based on a score that is differentiable with respect to a definition comprising particle positions or atom types; and (c) direct an output to via the communications interface, the output comprising a report comprising an identifier for the ligand structure.

In an aspect, the present disclosure provides, a method for machine learning aided modeling of two interacting structures. The method may comprise (a) receiving an input structure comprising an interaction region; (b) generating a plurality of candidate structures using a first differentiable machine learning model; (c) docking one or more candidate structures of the plurality of candidate structures at the interaction region of the input structure using a second differentiable machine learning model to predict a docking geometry; (d) ranking the one or more candidate structures docked in (c) using a third differentiable machine learning model or differentiable scoring function to predict a score; and (e) backpropagating the score to (i) the first differentiable machine learning model to update the plurality of candidate structures or (ii) the second differentiable machine learning model to update the docking geometry.

In some embodiments, the method further comprises outputting a list of the plurality of candidates updated in (e). In some embodiments, the input structure is a host molecule and the plurality of candidate structures comprises a guest molecule. In some embodiments, the input structure is a macromolecule or a biomolecule, the plurality of candidate structures comprises a ligand, and the interaction region is an active site. In some embodiments, the macromolecule or the biomolecule is a protein. In some embodiments, the protein is an enzyme. In some embodiments, the macromolecule or the biomolecule is a protein and the ligand is selected from the group consisting of another protein, a neurotransmitter, a toxin, a neuropeptide, and a steroid. In some embodiments, the macromolecule or the biomolecule is a protein and the ligand is an active pharmaceutical compound. In some embodiments, the macromolecule is a metal-organic framework. In some embodiments, the macromolecule is a polymer. In some embodiments, the input structure is a catalyst.

In some embodiments, the third machine learning model is the second machine learning model, and the score comprises a confidence estimate for the one or more of the plurality of candidate structures docked in (c). In some embodiments, the confidence estimate is a prediction of the root mean squared distance between a candidate structure and a ground truth structure. In some embodiments, the score comprises an indication of a binding affinity, a volume of the molecule, a dipole moment, or an interaction energy between the input structure and the plurality of candidate structures.

In some embodiments, (d) comprises generating a scoring function, wherein the scoring function is differentiable. In some embodiments, (b) comprises exploring a chemical space using one or more metrics selected from the group consisting of synthesizability, uniqueness, novelty, and diversity of proposals. In some embodiments, the first differentiable machine learning model is a generative model. In some embodiments, the generative model is a diffusion-based or a transformer-based generative model. In some embodiments, the diffusion-based generative model is a denoising diffusion probabilistic model. In some embodiments, the first differentiable machine learning model is a deep learning model. In some embodiments, the first differentiable machine learning model comprises one or more models selected from the group consisting of DiffSBDD, LIGAN, DeepLigBuilder, geoLDM, and RELATION. In some embodiments, the input structure, the plurality of candidate structures, or both are represented as SMILES strings. In some embodiments, the docking geometry comprises a predicted pose of the candidate structure with respect to the input structure.

In some embodiments, the second differentiable machine learning model is a generative model. In some embodiments, the generative model is a diffusion-based or a transformer-based generative model. In some embodiments, the second differentiable machine learning model comprises one or more models selected from the group consisting of DiffDock, GNINA, E3BIND, and TANKBind.

In some embodiments, (e) comprises using the first differentiable machine learning model to generate additional candidate structures, wherein the additional candidate structures are not in the plurality of candidate structures in (b). In some embodiments, (e) comprises backpropagating gradient information.

In some embodiments, the method further comprises estimating an inference reliability from at least one of differentiable machine learning models. In some embodiments, the method further comprises determining that the inference reliability is less than a threshold and recalculating an output of the at least one differentiable model using an underlying differentiable method on which the at least one of the differentiable machine learning models is trained or another differentiable method. In some embodiments, the method further comprises retraining the differentiable machine learning model based at least in part on an output from the underlying differentiable machine learning model and a gradient of the underlying differentiable machine learning model to improve the inference reliability.

In another aspect, the present disclosure provides, a system for machine learning aided modeling of two interacting structures. The system may comprise a non-transitory computer-readable medium with instructions stored thereon which when executed by a processor are configured to: (a) receive an input structure comprising an interaction region; (b) generate a plurality of candidate structures using a first differentiable machine learning model; (c) dock one or more candidate structures of the plurality of candidate structures at the interaction region of the input structure using a second differentiable machine learning model to predict a docking geometry; (d) rank the one or more candidate structures of the plurality of candidate structures docked in (c) using a third differentiable machine learning model or a differentiable scoring function to predict a score; and (e) backpropagate the score to (i) the first differentiable machine learning model to update the plurality of candidate structures or (ii) the second differentiable machine learning model to update the docking geometry.

In some embodiments, the processor is further configured to output a list of the plurality of candidates updated in (e). In some embodiments, the input structure is a host molecule and the plurality of candidate structures comprises a guest molecule. In some embodiments, the input structure is a macromolecule or a biomolecule, the plurality of candidate structures comprises a ligand, and the interaction region is an active site. In some embodiments, the macromolecule or the biomolecule is a protein. In some embodiments, the protein is an enzyme. In some embodiments, the macromolecule or the biomolecule is a protein and the ligand is selected from the group consisting of another protein, a neurotransmitter, a toxin, a neuropeptide, and a steroid. In some embodiments, the macromolecule or the biomolecule is a protein and the ligand is an active pharmaceutical compound. In some embodiments, the macromolecule is a metal-organic framework. In some embodiments, the macromolecule is a polymer. In some embodiments, the input structure is a catalyst.

In some embodiments, the third machine learning model is the second machine learning model, and the score comprises a confidence estimate for the one or more of the plurality of candidate structures docked in (c). In some embodiments, the confidence estimate is a prediction of the root mean squared distance between a candidate structure and a ground-truth structure. In some embodiments, the score comprises an indication of a binding affinity, a volume of the molecule, a dipole moment, or an interaction energy between the input structure and the plurality of candidate structures. In some embodiments, at (d) the processor is further configured to generate a scoring function, the scoring function is differentiable.

In some embodiments, at (b) the processor is further configured to explore a chemical space using one or more metrics selected from the group consisting of synthesizability, uniqueness, novelty, and diversity of proposals. In some embodiments, the first differentiable machine learning model is a generative model. In some embodiments, the generative model is a diffusion-based or a transformer-based generative model. In some embodiments, the diffusion-based generative model is a denoising diffusion probabilistic model. In some embodiments, the first differentiable machine learning model is a deep learning model. In some embodiments, the first differentiable machine learning model comprises one or more models selected from the group consisting of DiffSBDD, LiGAN, DeepLigBuilder, geoLDM, and RELATION.

In some embodiments, the input structure, the plurality of candidate structures, or both are represented as SMILES strings. In some embodiments, the docking geometry comprises a predicted pose of the candidate structure with respect to the input structure.

In some embodiments, the second differentiable machine learning model is a generative model. In some embodiments, the generative model is a diffusion-based or a transformer-based generative model. In some embodiments, the second differentiable machine learning model comprises one or more models selected from the group consisting of DiffDock, GNINA, E3BIND, and TANKBind. In some embodiments, at (b) the processor is further configured to use the first differentiable machine learning model or a differentiable scoring function to generate additional candidate structures, wherein the additional candidate structures are not in the plurality of candidate structures in (b).

In some embodiments, at (e) the processor is further configured to backpropagate gradient information. In some embodiments, the processor is further configured to estimate an inference reliability from at least one of differentiable machine learning models. In some embodiments, the processor is further configured to determine that the inference reliability is less than a threshold and recalculate an output of the at least one differentiable model using an underlying differentiable method on which the at least one of the differentiable machine learning models is trained or another differentiable method. In some embodiments, the processor is further configured to retrain the differentiable machine learning model based at least in part on an output from the underlying differentiable machine learning model and a gradient of the underlying differentiable machine learning model to improve the inference reliability.

In another aspect, the present disclosure provides, a system for machine learning aided modeling of two interacting structures. The system may comprise: (a) an indication of an input structure comprising an interaction region; (b) a first differentiable machine learning model configured to generate a plurality of candidate structures; (c) a second differentiable machine learning model configured to dock one or more candidate structures of the plurality of candidate structures at the interaction region of the input structure to predict a docking geometry; (d) a third differentiable machine learning model or a differentiable scoring function configured to rank the one or more candidate structures of the plurality of candidate structures docked by the second differentiable machine learning model to predict a score; and (e) an indication of an updated docking geometry, wherein the updated docking geometry is generated at least in part on a backpropagation of the score to (i) the first differentiable machine learning model to update the plurality of candidate structures or (ii) the second differentiable machine learning model.

In another aspect, the present disclosure provides, a method of optimizing reference compounds, comprising: (a) obtaining a target structure and a first ligand structure; (b) generating a latent vector based on the first ligand structure; (c) processing the latent vector, with or without SE(3) equivariance or other symmetries, to generate a second ligand structure based on (i) the target structure and (ii) a score comprising a measure of affinity between the target structure and the second ligand structure, wherein the score is differentiable with respect to a definition comprising particle positions or atom types; and (d) generating a report comprising an identifier for the second ligand structure.

In some embodiments, the target structure is generated using a machine learning model. In some embodiments, an interaction region of the target structure is generated using a machine learning model. In some embodiments, the machine learning model further generates the second ligand structure.

In some embodiments, the first ligand structure is a hit compound or a lead compound. In some embodiments, the first ligand structure is configured to interact with the target structure. In some embodiments, the first ligand structure is configured to bind to the target structure. In some embodiments, the second ligand structure is a lead compound or a lead-optimized compound. In some embodiments, the second ligand structure is configured to interact with the target structure. In some embodiments, the second ligand structure is configured to bind to the target structure. In some embodiments, the target structure is a protein structure. In some embodiments, the target structure comprises an interaction region. In some embodiments, the interaction region comprises a protein pocket. In some embodiments, the first ligand structure is a small molecule, a nucleic acid, a peptide, or a protein.

In some embodiments, the latent vector is a noisy latent vector. In some embodiments, the generating in (b) comprises noising an initial latent vector of the first ligand structure. In some embodiments, the noising comprises diffusing the initial latent vector of the first ligand structure. In some embodiments, the noising comprises stochastic noising. In some embodiments, the processing in (c) comprises denoising the latent vector. In some embodiments, the denoising comprises reverse diffusing the latent vector or a noisy ligand structure thereof. In some embodiments, processing in (c) is performed using a neural network. In some embodiments, the neural network is a diffusion model. In some embodiments, the target structure is fixed during the denoising. In some embodiments, the target structure is movable during the denoising.

In some embodiments, the measure of affinity is a measure of binding affinity. In some embodiments, the measure of affinity accounts for potential energy of the target structure and the ligand structure. In some embodiments, the measure of affinity accounts for free energy of the target structure and the ligand structure. In some embodiments, the particle positions comprise atom positions, coarse-grained particle positions, residue positions, or any combination thereof. In some embodiments, the particle positions comprise coordinates. In some embodiments, the measure of affinity is based on a force-field, a quantum chemical calculation, or a free energy perturbation calculation. In some embodiments, the processing in (c) is further based on a measure of synthetic accessibility of the second ligand structure. In some embodiments, the measure of synthetic accessibility is based on or not based on an equivariant neural network. In some embodiments, the processing in (c) is further based on a measure of feasibility that is based on an equivariant neural network. In some embodiments, the processing in (c) is further based on a measure of feasibility that is differentiable with respect to a definition comprising particle positions or atom types. In some embodiments, the measure of feasibility comprises measure of absorption, distribution, metabolism, and excretion-toxicity (ADMET).

In some embodiments, the method further comprises synthesizing the second ligand structure. In some embodiments, the method further comprises performing a binding assay to detect a binding event between the target structure and the second ligand structure. In some embodiments, the method further comprises performing the method using the second ligand structure as the first ligand structure.

In some embodiments, the target structure is a host molecule and the second ligand structure is a guest molecule. In some embodiments, the target structure is a macromolecule or a biomolecule, and the interaction region is an active site. In some embodiments, the macromolecule or the biomolecule is a protein. In some embodiments, the protein is an enzyme. In some embodiments, the macromolecule or the biomolecule is a protein and the ligand structure is selected from the group consisting of another protein, a neurotransmitter, a toxin, a neuropeptide, and a steroid. In some embodiments, the macromolecule or the biomolecule is a protein and the ligand structure is an active pharmaceutical compound. In some embodiments, the macromolecule is a metal-organic framework. In some embodiments, the macromolecule is a polymer. In some embodiments, the target structure is a catalyst.

In another aspect, the present disclosure provides, a method of generating lead compounds, comprising: (a) obtaining a target structure and a latent vector; (b) processing the latent vector to generate an intermediate latent vector; (c) processing the intermediate latent vector to generate a ligand structure; and (d) generating a report comprising an identifier for the ligand structure; (e) wherein the processing in (b) and (c) are performed with or without SE(3) equivariance or other symmetries and are based on (i) the target structure and (ii) a measure of affinity between the target structure and the ligand structure, wherein the measure of binding affinity is differentiable with respect to a definition comprising particle positions or atom types.

In some embodiments, the latent vector is a random latent vector. In some embodiments, the intermediate latent vector corresponds to a noisy ligand structure. In some embodiments, the processing in (c) is performed a plurality of times to generate a plurality of ligand structures.

In some embodiments, a gradient of the measure of affinity is propagatable to the intermediate latent vector. In some embodiments, the processing in (b) and (c) are based on a measure of synthesizability of the ligand structure. In some embodiments, a gradient of the measure of synthesizability is propagatable to the intermediate latent vector.

In some embodiments, the target structure is generated using a machine learning model. In some embodiments, an interaction region of the target structure is generated using a machine learning model. In some embodiments, the latent vector is generated using a machine learning model. In some embodiments, the ligand structure is configured to interact with the target structure. In some embodiments, the ligand structure is configured to bind to the target structure. In some embodiments, the target structure is a protein structure. In some embodiments, the target structure comprises an interaction region. In some embodiments, the interaction region comprises a protein pocket. In some embodiments, the ligand structure is a small molecule, a nucleic acid, a peptide, or a protein.

In some embodiments, the processing in (b) comprises denoising the latent vector. In some embodiments, the denoising comprises reverse diffusing the latent vector. In some embodiments, the processing in (b) is performed using a neural network. In some embodiments, the neural network is a diffusion model. In some embodiments, the target structure is fixed during the denoising. In some embodiments, the target structure is movable during the denoising.

In some embodiments, the measure of affinity is a measure of binding affinity. In some embodiments, the measure of affinity accounts for potential energy of the target structure and the ligand structure. In some embodiments, the measure of affinity accounts for free energy of the target structure and the ligand structure. In some embodiments, the particle positions comprise atom positions, coarse-grained particle positions, residue positions, or any combination thereof. In some embodiments, the particle positions comprise coordinates. In some embodiments, the measure of affinity is based on a force-field, a quantum chemical calculation, or a free energy perturbation calculation.

In some embodiments, the processing in (b) and (c) are further based on a measure of synthetic accessibility of the ligand structure. In some embodiments, the measure of synthetic accessibility is based on or not on an equivariant neural network. In some embodiments, the processing in (b) is further based on a measure of feasibility that is based on an equivariant neural network. In some embodiments, the processing in (b) is further based on a measure of feasibility that is differentiable with respect to a definition comprising particle positions or atom types. In some embodiments, the measure of feasibility comprises measure of absorption, distribution, metabolism, and excretion-toxicity (ADMET).

In some embodiments, the method further comprises synthesizing the ligand structure. In some embodiments, the method further comprises performing a binding assay to detect a binding event between the target structure and the ligand structure. In some embodiments, the method further comprises performing the method using the ligand structure to generate the latent vector.

In some embodiments, the target structure is a host molecule and the ligand structure is a guest molecule. In some embodiments, the target structure is a macromolecule or a biomolecule, and the interaction region is an active site. In some embodiments, the macromolecule or the biomolecule is a protein. In some embodiments, the protein is an enzyme. In some embodiments, the macromolecule or the biomolecule is a protein and the ligand structure is selected from the group consisting of another protein, a neurotransmitter, a toxin, a neuropeptide, and a steroid. In some embodiments, the macromolecule or the biomolecule is a protein and the ligand structure is an active pharmaceutical compound. In some embodiments, the macromolecule is a metal-organic framework. In some embodiments, the macromolecule is a polymer. In some embodiments, the target structure is a catalyst.

In another aspect, the present disclosure provides, a processor comprising a communications interface configured to connect to a computing system over a network, the processor configured to: (a) receive an indication of a problem from a user comprising a target structure and a first ligand structure; (b) direct instructions via the communications interface to generate a latent vector based on the first ligand structure, wherein the computing system is configured to process the latent vector, with or without SE(3) equivariance or other symmetries, to generate a second ligand structure based on (i) the target structure and (ii) a score comprising a measure of affinity between the target structure and the second ligand structure, wherein the score is differentiable with respect to a definition comprising particle positions or atom types; and (c) receive an output via the communications interface, the output comprising a report comprising an identifier for the second ligand structure.

In another aspect, the present disclosure provides, a processor comprising a communications interface configured to connect to a control system over a network, the processor configured to: (a) receive instructions via the communications interface, the instructions comprising an indication of a problem comprising a target structure and a first ligand structure from a control system; (b) implement instructions to: (i) generate a latent vector based on the first ligand structure; and (ii) process the latent vector, with or without SE(3) equivariance or other symmetries, to generate a second ligand structure based on (i) the target structure and (ii) a score comprising a measure of affinity between the target structure and the second ligand structure, wherein the score is differentiable with respect to a definition comprising particle positions or atom types; and (iii) direct an output to via the communications interface, the output comprising a report comprising an identifier for the second ligand structure.

In another aspect, the present disclosure provides, a processor comprising a communications interface configured to connect to a computing system over a network, the processor configured to: (a) receive an indication of a problem from a user comprising a target structure and a latent vector; (b) direct instructions via the communications interface to process the latent vector to generate an intermediate latent vector and to process the intermediate latent vector to generate a ligand structure, wherein the computing system is configured to perform the processing, with or without SE(3) equivariance or other symmetries, based on (i) the target structure and (ii) a measure of affinity between the target structure and the ligand structure, wherein the measure of binding affinity is differentiable with respect to a definition comprising particle positions or atom types; and (c) receive an output via the communications interface, the output comprising a report comprising an identifier for the ligand structure.

In another aspect, the present disclosure provides, a processor comprising a communications interface configured to connect to a control system over a network, the processor configured to: (a) receive instructions via the communications interface, the instructions comprising an indication of a problem comprising a target structure and a latent vector from a control system; (b) implement instructions to process the latent vector to generate an intermediate latent vector and to process the intermediate latent vector to generate a ligand structure, with or without SE(3) equivariance or other symmetries, based on (i) the target structure and (ii) a measure of affinity between the target structure and the ligand structure, wherein the measure of binding affinity is differentiable with respect to a definition comprising particle positions or atom types; and (c) direct an output to via the communications interface, the output comprising a report comprising an identifier for the ligand structure.

In another aspect, the present disclosure provides a method for machine learning aided modeling of a structure, the method comprising: (a) generating a plurality of candidate structures using a first differentiable machine learning model; (b) predicting one or more geometries of one or more candidate structures of the plurality of candidate structures using a second differentiable machine learning model; (c) ranking the one or more candidate structures of the plurality of candidate structures using a third differentiable machine learning model or differentiable scoring function to predict a score; and (d) propagating the score to (i) the first differentiable machine learning model to update the plurality of candidate structures or (ii) the second differentiable machine learning model to update the one or more geometries. In some embodiments, the method further comprises outputting a list of the plurality of candidates updated in (d).

In some embodiments, the plurality of candidate structures is provided in an environment, wherein the environment is vacuum, a gas phase media, a solvent media, or a solid surface. In some embodiments, the plurality of candidate structures comprises a macromolecule, a biomolecule, or a ligand. In some embodiments, the macromolecule or the biomolecule is a protein. In some embodiments, the protein is an enzyme. In some embodiments, the ligand is selected from the group consisting of another protein, a neurotransmitter, a toxin, a neuropeptide, and a steroid. In some embodiments, the ligand is an active pharmaceutical compound. In some embodiments, the macromolecule is a metal-organic framework. In some embodiments, the macromolecule is a polymer.

In some embodiments, the third machine learning model is the second machine learning model, and the score comprises a confidence estimate for the one or more geometries of the one or more candidate structures. In some embodiments, the confidence estimate is a prediction of the root mean squared distance between a candidate structure and a ground-truth structure. In some embodiments, the ground-truth structure is an experimentally determined structure. In some embodiments, the second machine learning model is the first machine learning model. In some embodiments, the score comprises an indication of a binding affinity, a volume of a molecule, or a dipole moment. In some embodiments, (c) comprises generating a scoring function, wherein the scoring function is differentiable. In some embodiments, (a) comprises exploring a chemical space using one or more metrics selected from the group consisting of synthesizability, uniqueness, novelty, and diversity of proposals.

In some embodiments, the first differentiable machine learning model is a generative model. In some embodiments, the generative model is a diffusion-based or a transformer-based generative model. In some embodiments, the diffusion-based generative model is a denoising diffusion probabilistic model. In some embodiments, the first differentiable machine learning model is a deep learning model. In some embodiments, the first differentiable machine learning model comprises one or more models selected from the group consisting of DiffSBDD, LiGAN, DeepLigBuilder, geoLDM, and RELATION. In some embodiments, the plurality of candidate structures are represented as SMILES structures.

In some embodiments, the second differentiable machine learning model is a generative model. In some embodiments, the generative model is a diffusion-based or a transformer-based generative model. In some embodiments, the second differentiable machine learning model comprises one or more models selected from the group consisting of DiffDock, GNINA, E3BIND. In some embodiments, the third differentiable machine learning model or differentiable scoring function comprises one or more models from the group consisting of ANI, Vina, Vinardo, Smina. In some embodiments, (d) comprises using the first differentiable machine learning model to generate additional candidate structures, wherein the additional candidate structures are not in the plurality of candidate structures in (a). In some embodiments, (d) comprises backpropagating gradient information. In some embodiments, (d) comprises forward propagating gradient information.

In some embodiments, the method further comprises estimating an inference reliability from at least one of differentiable machine learning models. In some embodiments, the method further comprises determining that the inference reliability is less than a threshold, and recalculating an output of the at least one differentiable model using an underlying differentiable method on which the at least one of the differentiable machine learning models is trained or another differentiable method. In some embodiments, the method further comprises retraining the differentiable machine learning model based at least in part on an output from the underlying differentiable machine learning model and a gradient of the underlying differentiable machine learning model to improve the inference reliability.

In another aspect, the present disclosure provides a system for machine learning aided modeling of a structure, the system comprising a non-transitory computer-readable medium with instructions stored thereon which when executed by a processor are configured to: (a) generate a plurality of candidate structures using a first differentiable machine learning model; (b) predict one or more geometries of one or more candidate structures of the plurality of candidate structures using a second differentiable machine learning model; (c) rank the one or more candidate structures of the plurality of candidate structures in (c) using a third differentiable machine learning model or a differentiable scoring function to predict a score; and (d) propagate the score to (i) the first differentiable machine learning model to update the plurality of candidate structures or (ii) the second differentiable machine learning model to update the one or more geometries. In some embodiments, the processor is further configured to output a list of the plurality of candidates updated in (d).

In some embodiments, plurality of candidate structures is provided in an environment, wherein the environment is vacuum, a gas phase media, a solvent media, or a solid surface. In some embodiments, the plurality of candidate structures comprises a macromolecule, a biomolecule, or a ligand. In some embodiments, macromolecule or the biomolecule is a protein. In some embodiments, the protein is an enzyme. In some embodiments, the ligand is selected from the group consisting of another protein, a neurotransmitter, a toxin, a neuropeptide, and a steroid. In some embodiments, the ligand is an active pharmaceutical compound. In some embodiments, the macromolecule is a metal-organic framework. In some embodiments, the macromolecule is a polymer.

In some embodiments, the third machine learning model is the second machine learning model, and wherein the score comprises a confidence estimate for the one or more candidate structures docked in (c). In some embodiments, the confidence estimate is a prediction of the root mean squared distance between a candidate structure and a ground truth structure. In some embodiments, the ground-truth structure is an experimentally determined structure. In some embodiments, the second machine learning model is the first machine learning model. In some embodiments, the score comprises an indication of a binding affinity, a volume of a molecule, or a dipole moment. In some embodiments, at (c) the processor is further configured to generate a scoring function, and the scoring function is differentiable. In some embodiments, at (a) the processor is further configured to explore a chemical space using one or more metrics selected from the group consisting of synthesizability, uniqueness, novelty, and diversity of proposals.

In some embodiments, the first differentiable machine learning model is a generative model. In some embodiments, the generative model is a diffusion-based or a transformer-based generative model. In some embodiments, the diffusion-based generative model is a denoising diffusion probabilistic model. In some embodiments, the first differentiable machine learning model is a deep learning model. In some embodiments, the first differentiable machine learning model comprises one or more models selected from the group consisting of DiffSBDD, LiGAN, DeepLigBuilder, geoLDM, and RELATION. In some embodiments, the plurality of candidate structures are represented as SMILES strings.

In some embodiments, the second differentiable machine learning model is a generative model. In some embodiments, the generative model is a diffusion-based or a transformer-based generative model. In some embodiments, the second differentiable machine learning model comprises one or more models selected from the group consisting of DiffDock, GNINA, E3BIND, and TANKBind. In some embodiments, the third differentiable machine learning model or differentiable scoring function comprises one or more models from the group consisting of ANI, Vina, Vinardo, Smina.

In some embodiments, at (d) the processor is further configured to use the first differentiable machine learning model to generate additional candidate structures, wherein the additional candidate structures are not in the plurality of candidate structures in (a). In some embodiments, at (d) the processor is further configured to backpropagate gradient information. In some embodiments, at (d) the processor is further configured to forward propagate gradient information. In some embodiments, the processor is further configured to estimate an inference reliability from at least one of differentiable machine learning models. In some embodiments, the processor is further configured to determine that the inference reliability is less than a threshold, and recalculate an output of the at least one differentiable model using an underlying differentiable method on which the at least one of the differentiable machine learning models is trained or another differentiable method. In some embodiments, the processor is further configured to retrain the differentiable machine learning model based at least in part on an output from the underlying differentiable machine learning model and a gradient of the underlying differentiable machine learning model to improve the inference reliability.

In another aspect, the present disclosure provides a system for machine learning aided modeling of a structure, the system comprising: (a) a first differentiable machine learning model configured to generate a plurality of candidate structures; (b) a second differentiable machine learning model configured to predict one or more geometries of one or more candidate structures of the plurality of candidate structures using a second differentiable machine learning model; (c) a third differentiable machine learning model configured to rank the one or more candidate structures of the plurality of candidate structures in (c) to predict a score; and (d) an indication of an updated geometry, wherein the updated geometry is generated at least in part on a propagation of the score to (i) the first differentiable machine learning model to update the plurality of candidate structures or (ii) the second differentiable machine learning model to update the one or more geometries.

In another aspect, the present disclosure provides a method of optimizing reference compounds, comprising:

obtaining a first ligand structure; generating a latent vector based on the first ligand structure; processing the latent vector, with or without SE(3) equivariance or other symmetries, to generate a second ligand structure based on a score that is differentiable with respect to a definition comprising particle positions or atom types; and generating a report comprising an identifier for the second ligand structure. In some embodiments, a machine learning model generates the second ligand structure.

In some embodiments, the first ligand structure is a hit compound or a lead compound. In some embodiments, the second ligand structure is a lead compound or a lead-optimized compound. In some embodiments, the first ligand structure is a small molecule, a nucleic acid, a peptide, or a protein. In some embodiments, the latent vector is a noisy latent vector.

In some embodiments, the generating in (b) comprises noising an initial latent vector of the first ligand structure. In some embodiments, the noising comprises diffusing the initial latent vector of the first ligand structure. In some embodiments, the noising comprises stochastic noising. In some embodiments, the processing in (c) comprises denoising the latent vector. In some embodiments, the denoising comprises reverse diffusing the latent vector or a noisy ligand structure thereof.

In some embodiments, the processing in (c) is performed using a neural network. In some embodiments, the neural network is a diffusion model. In some embodiments, the particle positions comprise atom positions, coarse-grained particle positions, residue positions, or any combination thereof. In some embodiments, the particle positions comprise coordinates.

In some embodiments, the processing in (c) is further based on a measure of synthetic accessibility of the second ligand structure. In some embodiments, in the measure of synthetic accessibility is based on or not based on an equivariant neural network. In some embodiments, the processing in (c) is further based on a measure of feasibility that is based on an equivariant neural network. In some embodiments, the processing in (c) is further based on a measure of feasibility that is differentiable with respect to a definition comprising particle positions or atom types. In some embodiments, the measure of feasibility comprises measure of absorption, distribution, metabolism, and excretion-toxicity (ADMET). In some embodiments, the method further comprises synthesizing the second ligand structure. In some embodiments, the method further comprises performing the method using the second ligand structure as the first ligand structure. In some embodiments, the first ligand structure is provided in an environment, and wherein the environment is vacuum, a gas phase media, a solvent media, or a solid surface.

In another aspect, the present disclosure provides a method of generating lead compounds, comprising: obtaining a latent vector; processing the latent vector to generate an intermediate latent vector; processing the intermediate latent vector to generate a ligand structure; and generating a report comprising an identifier for the ligand structure; wherein the processing in (b) and (c) are performed with or without SE(3) equivariance or other symmetries and are based on a score that is differentiable with respect to a definition comprising particle positions or atom types.

In some embodiments, the latent vector is a random latent vector. In some embodiments, the intermediate latent vector corresponds to a noisy ligand structure. In some embodiments, the processing in (c) is performed a plurality of times to generate a plurality of ligand structures. In some embodiments, a gradient of the measure of affinity is propagatable to the intermediate latent vector. In some embodiments, the processing in (b) and (c) are based on a measure of synthesizability of the ligand structure. In some embodiments, a gradient of the measure of synthesizability is propagatable to the intermediate latent vector. In some embodiments, the latent vector is generated using a machine learning model. In some embodiments, the ligand structure is a small molecule, a nucleic acid, a peptide, or a protein. In some embodiments, the processing in (b) comprises denoising the latent vector. In some embodiments, the denoising comprises reverse diffusing the latent vector. In some embodiments, the processing in (b) is performed using a neural network. In some embodiments, the neural network is a diffusion model. In some embodiments, the particle positions comprise atom positions, coarse-grained particle positions, residue positions, or any combination thereof. In some embodiments, the particle positions comprise coordinates. In some embodiments, the measure of affinity is based on a force-field, a quantum chemical calculation, or a free energy perturbation calculation. In some embodiments, the processing in (b) and (c) are further based on a measure of synthetic accessibility of the ligand structure. In some embodiments, the measure of synthetic accessibility is based on or not on an equivariant neural network. In some embodiments, the processing in (b) is further based on a measure of feasibility that is based on an equivariant neural network. In some embodiments, the processing in (b) is further based on a measure of feasibility that is differentiable with respect to a definition comprising particle positions or atom types. In some embodiments, the measure of feasibility comprises measure of absorption, distribution, metabolism, and excretion-toxicity (ADMET). In some embodiments, the method further comprises synthesizing the ligand structure. In some embodiments, the method further comprises performing the method using the ligand structure to generate the latent vector.

In another aspect, the present disclosure provides a computer program product comprising a computer-readable medium having computer-executable code encoded therein, the computer-executable code adapted to be executed to implement any one of the methods disclosed herein. In some embodiments, the computer-executable code is callable through an active programming interface.

In another aspect, the present disclosure provides a non-transitory computer-readable storage media encoded with a computer program including instructions executable by one or more processors to implement any one of the methods disclosed herein. In some embodiments, the instructions are callable through an active programming interface.

In another aspect, the present disclosure provides a computer-implemented system comprising: a digital processing device comprising: at least one processor, an operating system configured to perform executable instructions, a memory, and a computer program including instructions executable by the digital processing device to perform any one of the methods disclosed herein. In some embodiments, the computer-implemented system is callable through an active programming interface.

In another aspect, the present disclosure provides a processor comprising a communications interface configured to connect to a computing system over a network, the processor configured to: receive an indication of a problem from a user comprising a first ligand structure; direct instructions via the communications interface to generate a latent vector based on the first ligand structure, wherein the computing system is configured to process the latent vector, with or without SE(3) equivariance or other symmetries, to generate a second ligand structure based on a score comprising that is differentiable with respect to a definition comprising particle positions or atom types; and receive an output via the communications interface, the output comprising a report comprising an identifier for the second ligand structure.

In another aspect, the present disclosure provides a processor comprising a communications interface configured to connect to a control system over a network, the processor configured to: receive instructions via the communications interface, the instructions comprising an indication of a problem comprising a first ligand structure from a control system; implement instructions to: generate a latent vector based on the first ligand structure; and process the latent vector, with or without SE(3) equivariance or other symmetries, to generate a second ligand structure based on a score that is differentiable with respect to a definition comprising particle positions or atom types; and direct an output to via the communications interface, the output comprising a report comprising an identifier for the second ligand structure.

In another aspect, the present disclosure provides a processor comprising a communications interface configured to connect to a computing system over a network, the processor configured to: receive an indication of a problem from a user comprising a latent vector; direct instructions via the communications interface to process the latent vector to generate an intermediate latent vector and to process the intermediate latent vector to generate a ligand structure, wherein the computing system is configured to perform the processing, with or without SE(3) equivariance or other symmetries, based on a score that is differentiable with respect to a definition comprising particle positions or atom types; and receive an output via the communications interface, the output comprising a report comprising an identifier for the ligand structure.

In another aspect, the present disclosure provides a processor comprising a communications interface configured to connect to a control system over a network, the processor configured to: receive instructions via the communications interface, the instructions comprising an indication of a problem comprising a latent vector from a control system; implement instructions to process the latent vector to generate an intermediate latent vector and to process the intermediate latent vector to generate a ligand structure, with or without SE(3) equivariance or other symmetries, based on a score that is differentiable with respect to a definition comprising particle positions or atom types; and direct an output to via the communications interface, the output comprising a report comprising an identifier for the ligand structure.

Another aspect of the present disclosure provides a system comprising one or more computer processors and computer memory coupled thereto. The computer memory comprises machine executable code that, upon execution by the one or more computer processors, implements any of the methods above or elsewhere herein.

Another aspect of the present disclosure provides a computer program product, wherein the computer-executable code is callable through an active programming interface.

Another aspect of the present disclosure provides a non-transitory computer-readable storage media encoded with a computer program including instructions executable by one or more processors to implement any one of the systems or methods disclosed herein. In some embodiments, the instructions are callable through an active programming interface.

Another aspect of the present disclosure provides a computer-implemented system comprising: a digital processing device comprising: at least one processor, an operating system configured to perform executable instructions, a memory, and a computer program including instructions executable by the digital processing device to implement any one of the systems or methods disclosed herein. In some embodiments, the computer-implemented system is callable through an active programming interface.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2 is a flowchart of an example of a method for modeling two interacting structures.

FIG. 5A illustrates how random latent vectors are generated (which can be skipped when seeded with a known ligand) and how the reverse diffusion is performed for diffusion time T→$t_{hz}$. FIG. 5B illustrates how the rest of the reverse diffusion process is completed and a ligand is generated (with coordinates and atomic numbers).

30 and $$z_t^1$$

is defined by taking a single optimization step.

Figure 6:
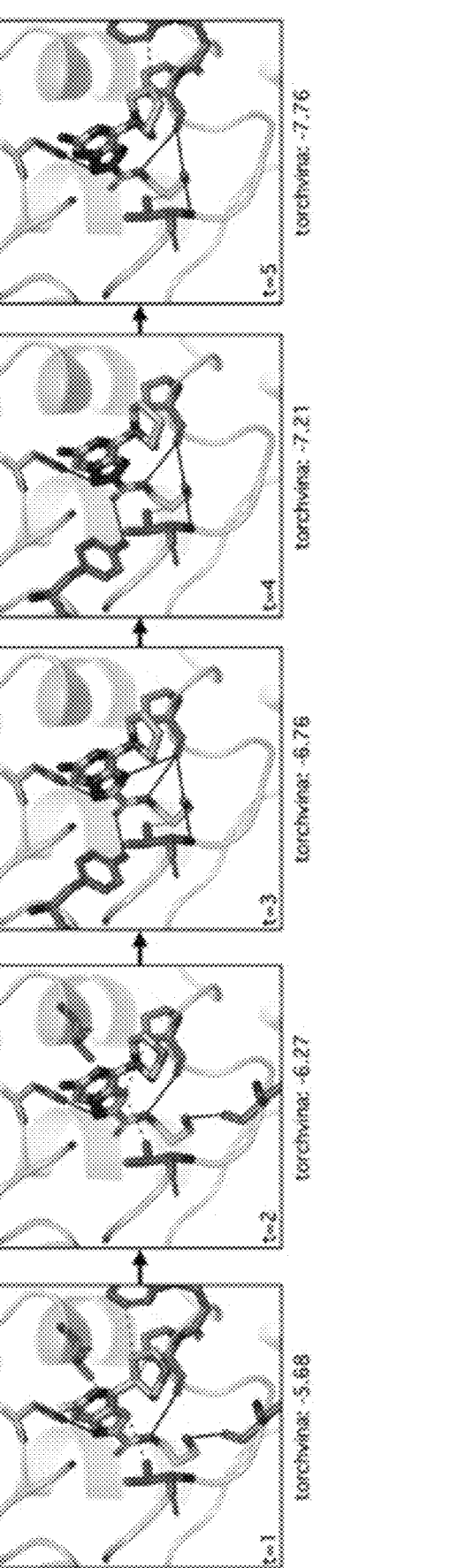

FIG. 6 illustrates a cartoon of an example of protein-ligand binding structure generation. Evolution of a ligand during latent vector optimization is performed with a model disclosed herein. Solid lines represent hydrogen bonding, dotted lines represent hydrophobic interactions or pi-stacking interactions.

Figure 7:
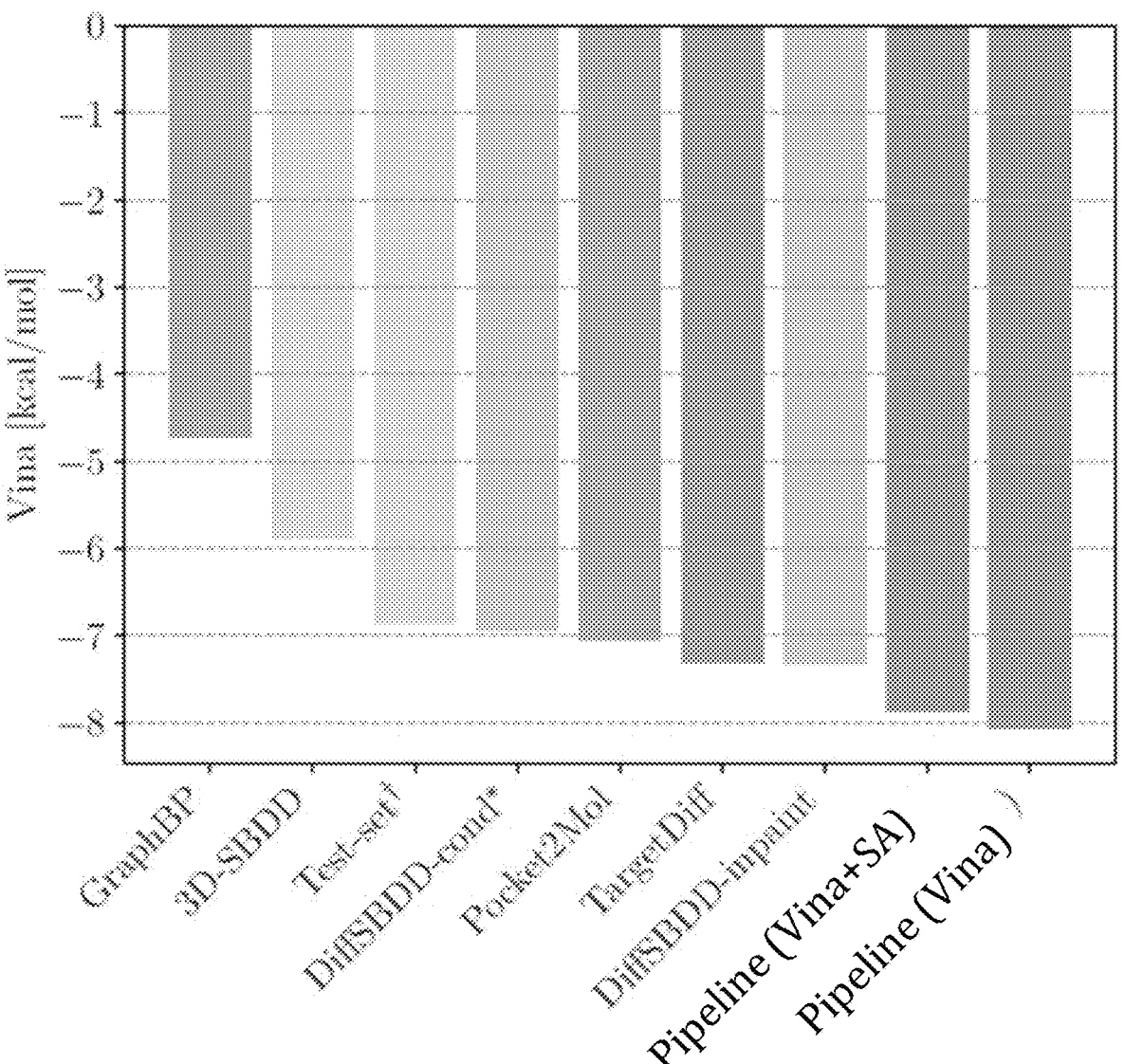

FIG. 7 shows model performance on benchmark test sets for an embodiment of the present disclosure. Average Vina scores of various ML tools are shown for CrossDocked (left), and Binding MOAD (right) are shown. † indicates Vina scores of reference ligands in the test set, redocked with QVina. * indicates baseline method for a model of the present disclosure.

Figure 8:
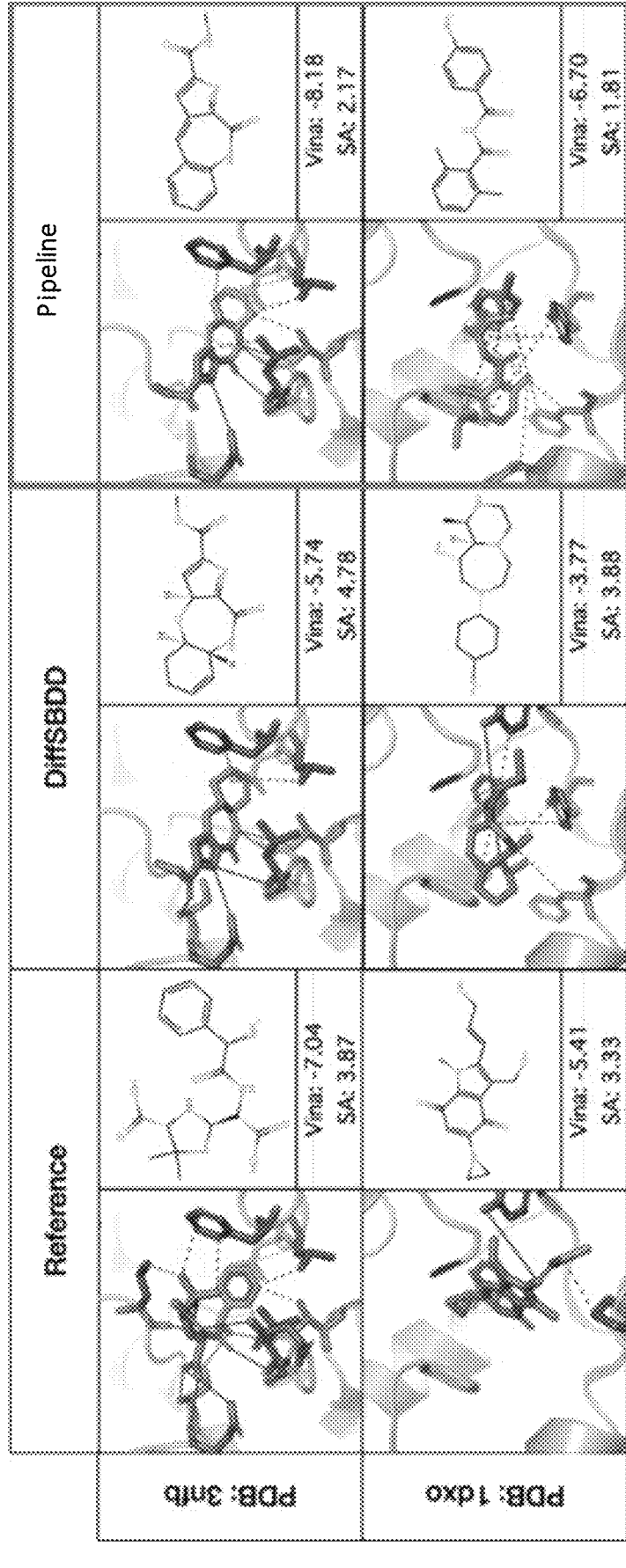

FIG. 8 illustrates cartoons of example molecules produced by various models. Two examples from the CrossDocked test set are shown—protein 3nfb, and protein 1dxo. The left column shows reference molecules from the test sets. The middle column shows initial ligand produced by a reference model prior to latent vector optimization. The right column shows a molecule produced by a model of the present disclosure after optimizing torchvina and torchSA objective functions. For each example, the molecule produced by DiffSBDD exhibited better Vina and SA scores than the reference molecule. After optimization with a model of the present disclosure, both the Vina and SA scores of the generated molecule are better than the reference.

Figure 9:
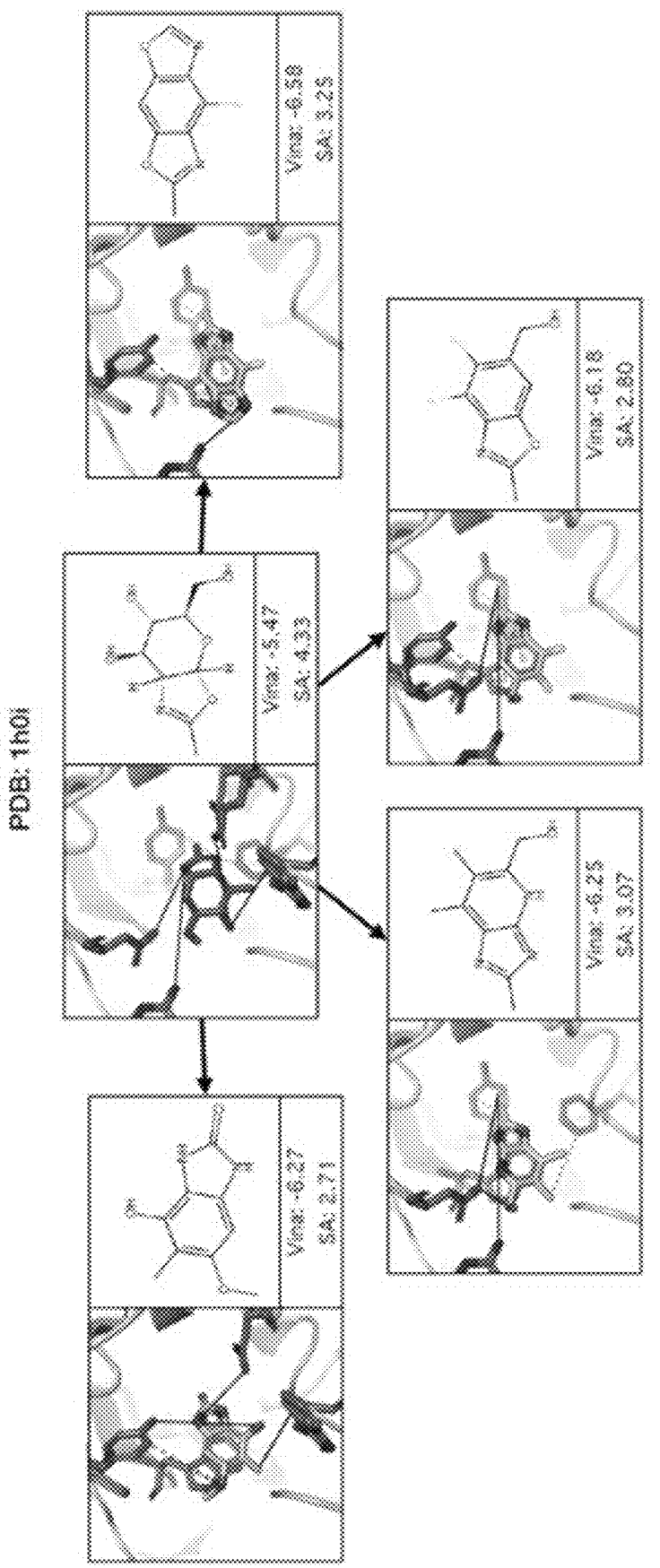

FIG. 9 shows cartoons of example molecules produced by a model of the present disclosure during reference optimization. The ligand ngo is docked into protein 1h0i. The model is used to optimize torchvina and torchSA objective functions. The model yields multiple ligands with improved SA and Vina relative to the reference molecule.

Figure 10:
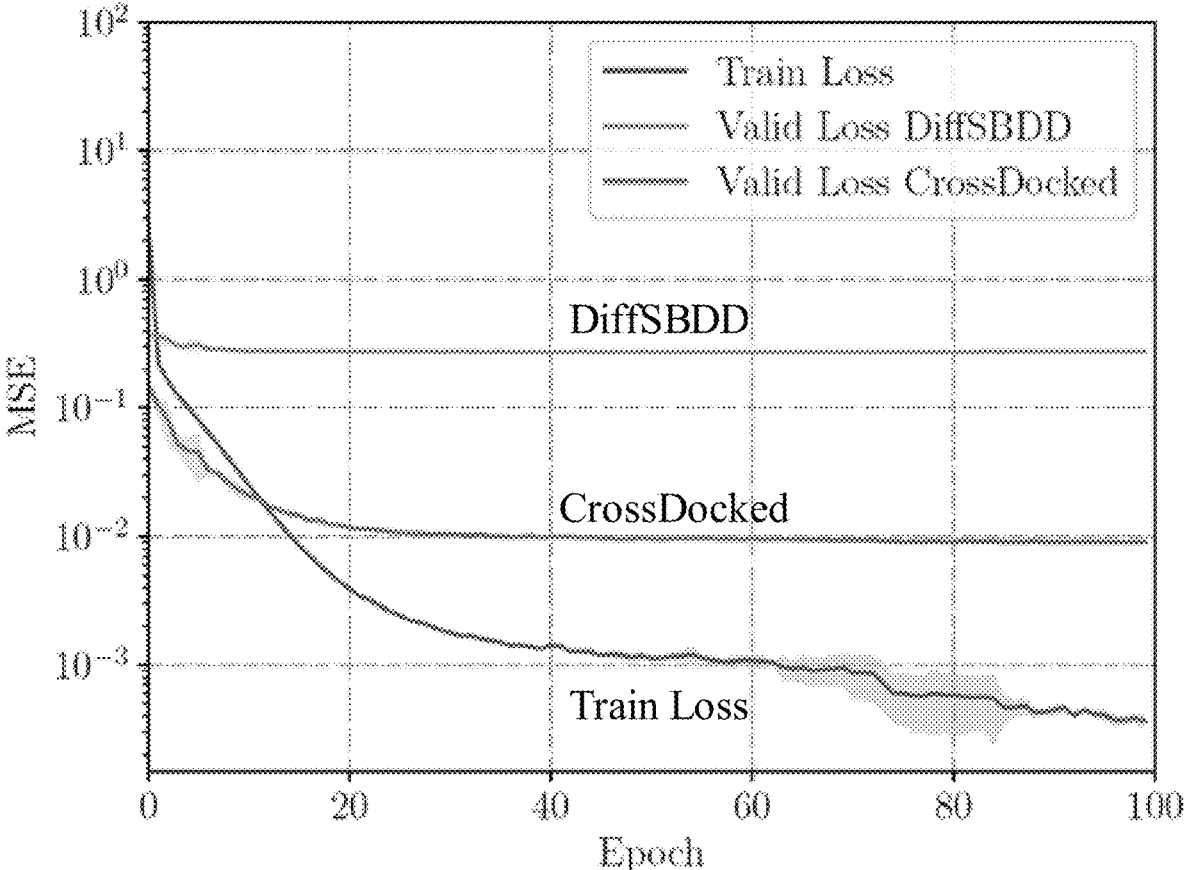

FIG. 10 shows an example of training and validation curve for training PaiNN to predict SA score. The mean squared error (MSE) at each epoch is plotted for the training set, the DiffSBDD validation set, and the CrossDocked validation set. The MSE at each epoch is averaged across the 5 runs, and the standard deviation is plotted as a transparent region.

Figure 11:
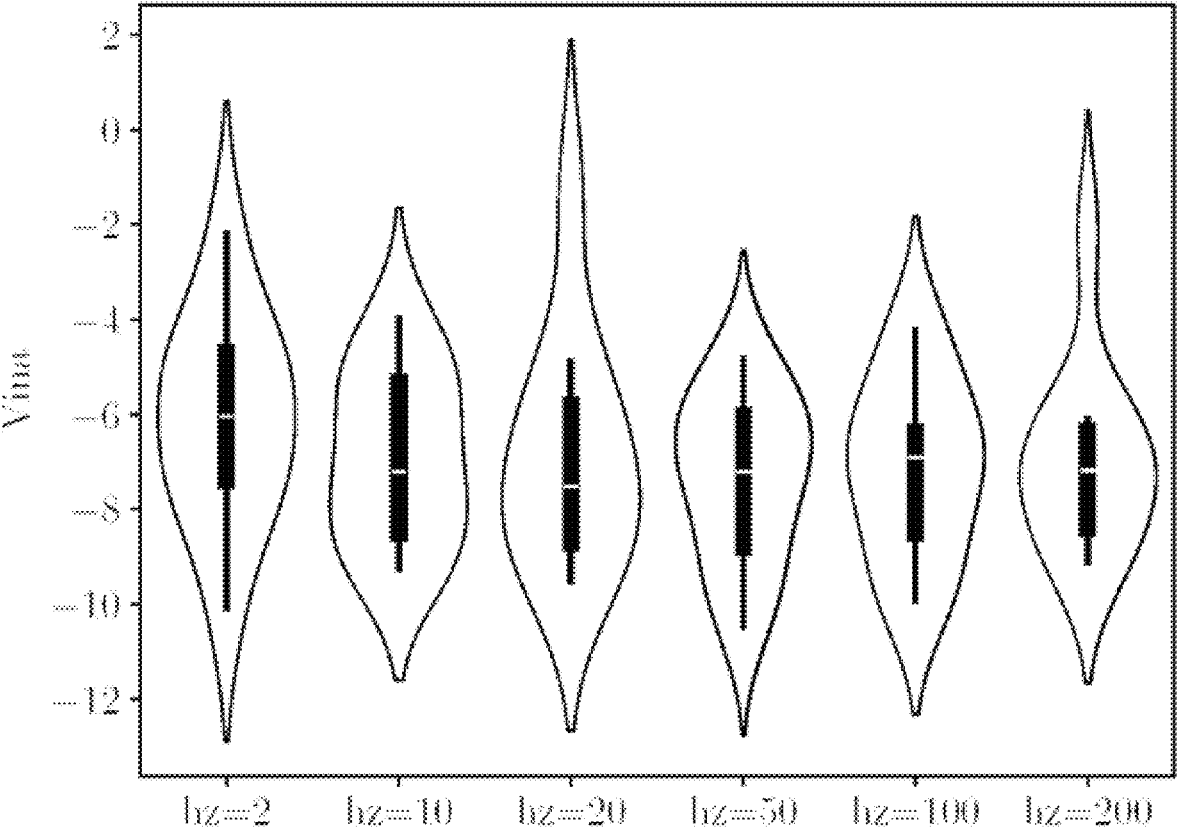

FIG. 11 shows an example of a distribution of average Vina scores on targets in the validation set when used with learning rate (lr)=0.1.

Figure 12:
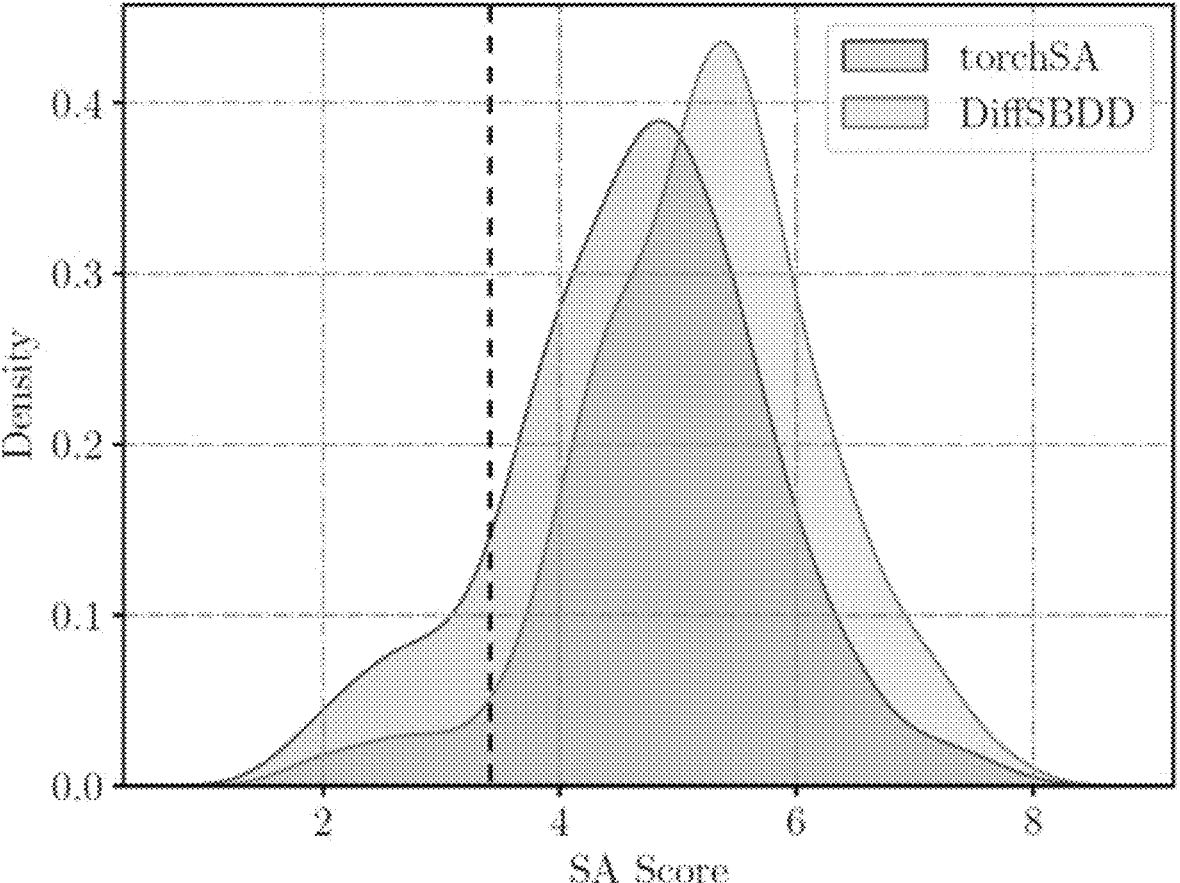

FIG. 12 shows an example of a distribution of SA scores before and after optimization of latent vectors with torchSA, when the lr in Adam is set to 0.05. The cutoff for determining synthesizability is denoted by a bolded dotted black line.

Figure 13:
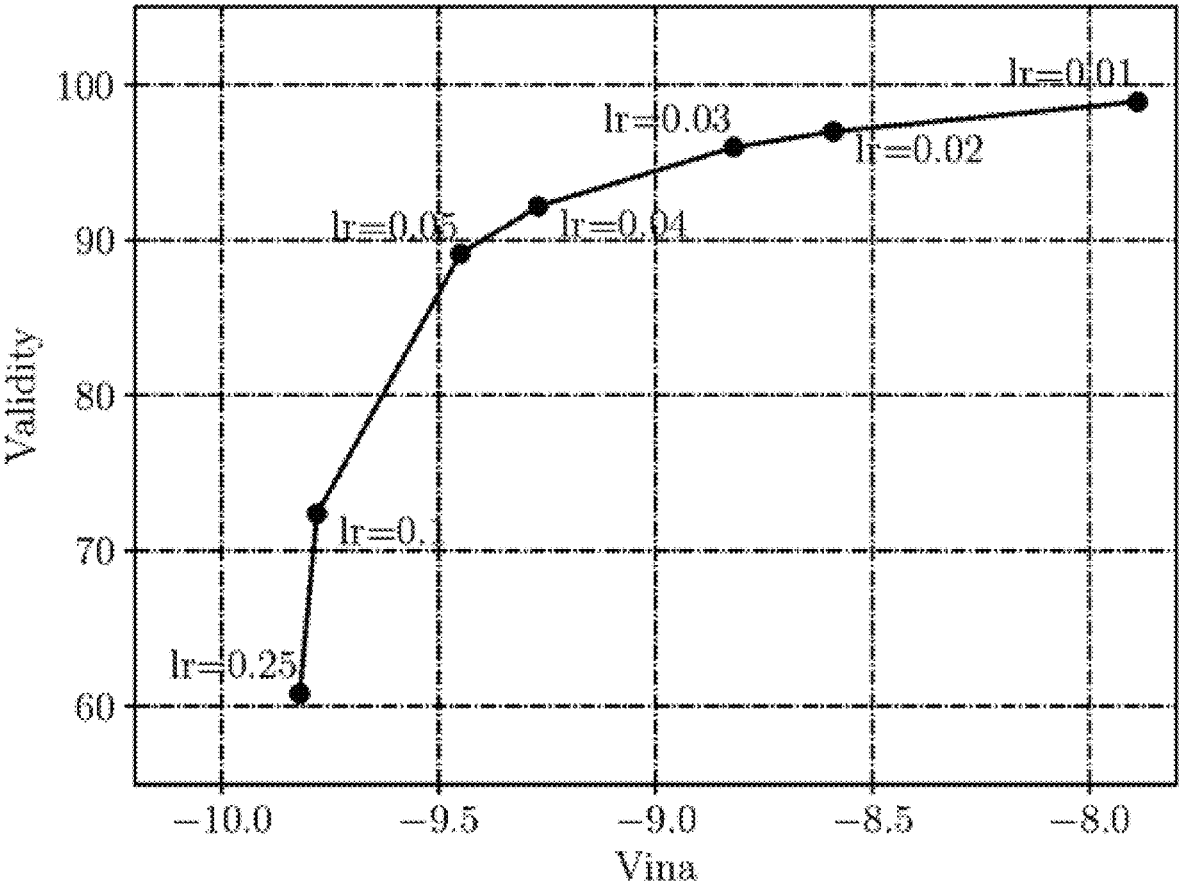

FIG. 13 shows a trade-off between validity and high binding affinity experienced when changing lr in a model of the present disclosure. Once lr exceeds 0.05, a sharp drop-off in validity is exhibited in this example.

Figure 14:
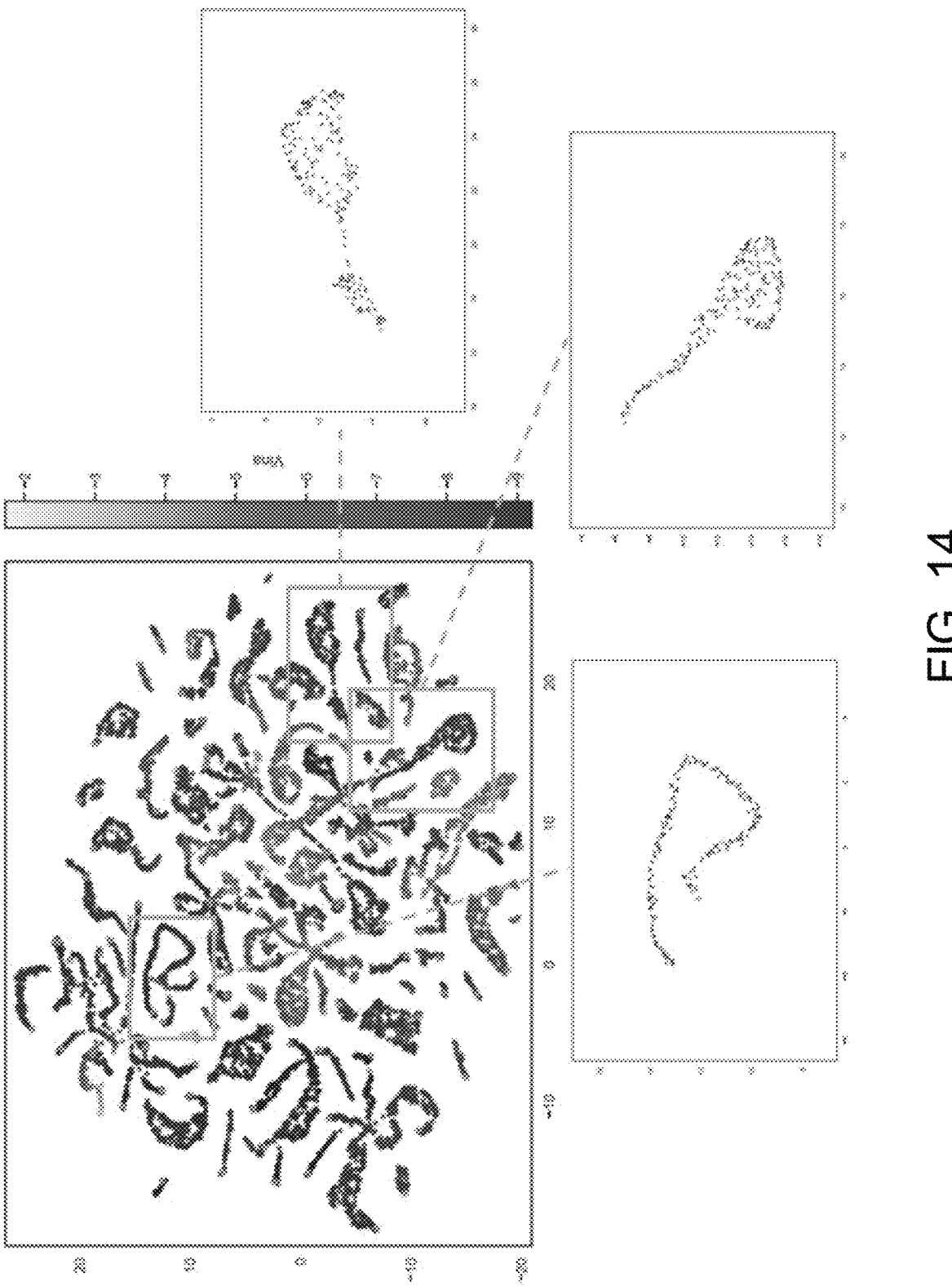

FIG. 14 shows a visualization of latent vector visualizations of a model of the present disclosure when generating ligands for 14 gs. The points are shaded by the magnitude of the Vina score (darker implying lower scores), and a star marks the end of the optimization trajectory.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

The term "plurality" means "two or more," unless expressly specified otherwise.

The term "herein" means "in the present application, including anything which may be incorporated by reference," unless expressly specified otherwise.

The term "e.g.," and like terms mean "for example," and thus do not limit the terms or phrases they explain. For example, in a sentence "the computer sends data (e.g., instructions, a data structure) over the Internet," the term "e.g.," explains that "instructions" are an example of "data" that the computer may send over the Internet, and also explains that "a data structure" is an example of "data" that the computer may send over the Internet. However, both "instructions" and "a data structure" are merely examples of "data," and other things besides "instructions" and "a data structure" can be "data."

Certain inventive embodiments herein contemplate numerical ranges. When ranges are present, the ranges include the range endpoints. Additionally, every sub range and value within the range is present as if explicitly written out.

The term "about" or "approximately" may mean within an acceptable error range for the particular value, which will depend in part on how the value is measured or determined, e.g., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Where particular values are described in the application and claims, unless otherwise stated the term "about" meaning within an acceptable error range for the particular value may be assumed.

As used herein, the term "classical," as used in the context of computing or computation, generally refers to computation performed using binary values using discrete bits without use of quantum mechanical superposition and quantum mechanical entanglement. A classical computer may be a digital computer, such as a computer employing discrete bits (e.g., 0's and 1's) without use of quantum mechanical superposition and quantum mechanical entanglement.

As used herein, the term "non-classical," as used in the context of computing or computation, generally refers to any method or system for performing computational procedures outside of the paradigm of classical computing.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be used, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

In an aspect, the present disclosure provides, systems and methods for machine learning aided modeling of two interacting structures. In some embodiments, the systems and methods make use of gradient information with respect to the objectives in molecule generation/search schemes. The systems and methods can be used to produce a set of chemically feasible ligands for a protein pocket. In some embodiments, latent variables of a generative model can be optimized based on the gradient information for one or more objective of interest. In some embodiments, the objectives can comprise binding affinity, synthetic accessibility, or both. In some embodiments, the gradient information may be generated by a property predictor. In some embodiments, the property predictor may process a noise or intermediate representation of a molecule or a latent variable thereof. In some embodiments, the property predictor may process a molecular structure or a latent variable thereof.

In some aspects, provided herein are systems and methods for producing ligands with desired properties for a given protein pocket. This can be accomplished by constructing a computational graph that begins with latent variables of a diffusion model and ends with important metrics in drug discovery. The latent variables can be modified via optimization routines to optimize the metrics of interest. The optimization routines can comprise uni-variate optimization or multivariate optimization.

In some embodiments, an equivariant probabilistic model can be used to sequentially generate new atoms in a protein given a context of atomic positions. In some embodiments, an equivariant diffusion model can be used to generate ligands from scratch. In some embodiments, an equivariant diffusion model can be used to generate a ligand from scratch. In some embodiments, models can be used as an unsupervised extractor of binding affinity. In some embodiments, models can be used to perform scaffold-hopping, fragment merging, fragment growing, all of which can be facilitated by an inpainting scheme.

Sampling ligands by using these models can be more efficient than searching through a database and may produce new molecules that do not currently exist in databases in the first place. Models can thereby expand the chemical space available during the drug-discovery process. Models can be coupled to an evaluation scheme to filter and rank molecules based on desired properties. A feedback loop from the evaluation scheme can be coupled to a molecule generator of a model to allow for conditional generation, improving the sampling to yield molecules with better target properties.

Conditional generation can be implemented in various ways. For example, it can comprise a policy network with a Monte Carlo Tree Search algorithm. In some embodiments, it can comprise a diffusion model with an evolutionary algorithm. In some embodiments, it can comprise a property predictor that guides a generative model composed of an equivariant autoencoder and transformer decoder in generating molecules with optimal target properties.

Thus, systems and methods of the present disclosure may be used to propose optimal drugs given particular properties. The systems and methods may be used to expand the ability to virtually screen optimized molecules from a vast chemical space. Such screening may be performed without the need of searching through a vast database, or generating molecules randomly until one with desired properties is found, therefore accelerating the drug discovery process.

In some embodiments, other important metrics can be included, which may be dependent on the specific solutions desired for generation. For example, toxicity and solubility may be used as additional objectives to ensure the generation of feasible ligands, along with the consideration of other binding affinity metrics such as estimations of free energy of binding (e.g., based on free energy perturbation (FEP) methods).

In some embodiments, system and methods of the present disclosure provide a pipeline that takes a first structure as an input (e.g., a chemical system, a protein, etc.) and return a shortlist of candidate structures (e.g., ligands, molecules, etc.) that are ranked based on some scoring function. In some embodiments, the systems and methods provided herein use machine learning models to propose candidate structures, combine them, and rank them. In some embodiments, each of the operations of proposing candidate structures, combining them, and ranking them are performed by different machine learning models. In some embodiments, one or more of proposing, combining, and ranking may be proposed by the same machine learning model (e.g., two total models vs. 1 total model). The systems and methods disclosed herein may comprises a differentiable pipeline. A differentiable pipeline may provide a connection between each machine learning model such that all three operations may be optimized together, in sequence, or piece by piece depending on the selection of the user.

An advantage of the systems and methods of the present disclosure can include the use of differentiable machine learning models along with a differentiable scoring function to achieve a fully differentiable pipeline. Full differentiability allows for iteratively updating the proposed set of generated candidate structures to optimize a scoring function. In an example, users may obtain an optimal and accurately ranked set of ligands given a particular protein.

Another advantage the systems and methods of the present disclosure can include acceleration of laboratory-based discovery processes. Such laboratory-based discovery processes, without acceleration, can take 10+ years and cost 2 billion USD. In some embodiments, the systems and methods disclosed herein provide a faster and less expensive approach compared to a laboratory-based drug discovery process.

Another advantage of the systems and methods of the present disclosure can be the use of generative machine learning models to predict candidate structures. Instead of using a pre-enumerated virtual compounds library, such as Enamine REAL containing 6 billion compounds or MolDB containing 1 trillion compounds, systems and methods of the present disclosure may generate new candidate structures based on the optimization. Considering that synthesizable chemical space is estimated to be $10^{180}$, maintaining such large libraries scale both poorly (in terms of both time and cost) and inadequately sample the chemical space ($10^{12}$ is much smaller than $10^{180}$).

Another advantage of the systems and methods of the present disclosure can be the use of gradient information from the differentiable machine learning model. Optimization of scoring functions without gradient information may be slow, as they may run many smaller docking simulations which are costly. Further, optimizing scoring functions without gradient information may produce less optimal results when compared to strategies that incorporate gradient information.

Another advantage of the systems and methods of the present disclosure can be to provide a faster and less expensive approach compared to other machine learning based tools. Derivative-free techniques may use a large number of function evaluations to explore the optimization landscape. For example, in the case of docking, where a function evaluation is typically on the order of 10 seconds (DiffDock) to 2 minutes (Smina), one may need to make potentially thousands of function evaluations to optimize a single ligand resulting in a steep compute cost. With a fully differentiable pipeline, each time the function is evaluated, one can compute the gradient. This additional information can be leveraged to accelerate the optimization, as methods integrating gradient information require significantly less function evaluations than random sampling techniques.

Another advantage of the systems and methods of the present disclosure can be that the use of estimation of inference is more reliable when generated from a differentiable machine learning model. When the reliability is less than a certain threshold, the system can perform the prediction by using the underlying differentiable method on which a machine learning model is trained on or another differentiable method, and its gradient information is used. In some cases, the output from the differentiable method may be used to retrain the machine learning model to improve its inference reliability.

Machine Learning

Systems and methods of the present disclosure may implement various machine learning methods. Machine learning (ML) may comprise training (e.g., tuning parameters within) a flexible computer algorithm with a particular set of data. More specifically, ML may comprise supervised learning, semi-supervised learning, unsupervised learning, and reinforcement learning. In supervised learning, parameters within an ML model may be updated such that the output of the model and the labelled data yield a similar result. In unsupervised learning, a model may learn patterns within a particular dataset without labels. In semi-supervised learning, some labels may be present, and others are not. In reinforcement learning, a model may be used to determine what actions to take given a particular environment. A particular set of machine learning models, used in some embodiments, are neural networks, which may include the layers: fully connected, convolution, pooling, skip connections, etc. When many layers are connected in a neural network, this may be referred to as a deep learning model. Deep learning models have many parameters and require many datapoints to reduce the error in their predictions.

In some embodiments, systems and methods of the present disclosure may comprise differentiable machine learning models. A machine learning model may differentiable may comprise input variables that are input in such a way that a derivative may be defined. In an example, PyTorch may facilitate indexing of variables and operation on the variables, which all for each derivative and how parameters are connected to be monitored.

Computer Systems

Systems and methods of the present disclosure may implement various operations on a digital computer. In some embodiments, a digital computer comprises one or more hardware central processing units (CPUs) that carry out the digital computer's functions. In some embodiments, the digital computer further comprises an operating system configured to perform executable instructions. In some embodiments, the digital computer is connected to a computer network. In some embodiments, the digital computer is connected to the Internet such that it accesses the World Wide Web. In some embodiments, the digital computer is connected to a cloud computing infrastructure. In some cases, the digital computer is connected to an intranet. In some embodiments, the digital computer is connected to a data storage device.

Various types of digital computer may be used. Suitable digital computers may include, by way of non-limiting examples, server computers, desktop computers, laptop computers, notebook computers, sub-notebook computers, netbook computers, netbook computers, set-top computers, media streaming devices, handheld computers, Internet appliances, mobile smartphones, tablet computers, personal digital assistants, video game consoles, and vehicles. Smartphones may be suitable for use with one or more examples of the method and the system described herein. Select televisions, video players, and digital music players, in some embodiments with computer network connectivity, may be suitable for use in some cases of the system and the method described herein. Suitable tablet computers may include those with booklet, slate, and convertible configurations.

In some embodiments, the digital computer comprises an operating system configured to perform executable instructions. The operating system may be, for example, software, comprising programs and data, which manages the device's hardware and provides services for execution of applications. Various types of operating system may be used. For example, suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Suitable personal computer operating systems may include, by way of non-limiting examples, Microsoft® Windows®, Apple® Mac OS X®, UNIX®, and UNIX-like operating systems such as GNU/Linux®. In some embodiments, the operating system is provided by cloud computing. Suitable mobile smart phone operating systems may include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Suitable media streaming device operating systems may include, by way of non-limiting examples, Apple TV®, Roku®, Boxee® Google TV®, Google Chromecast®, Amazon Fire®, and Samsung® HomeSync®. Suitable video game console operating systems may include, by way of non-limiting examples, Sony® PS3®, Sony® PS4®, Microsoft® Xbox 360®, Microsoft® Xbox One®, Nintendo® Wii®, Nintendo® Wii U®, and Ouya®.

In some embodiments, the digital computer comprises a storage and/or memory device. Various types of storage and/or memory may be used in the digital computer. In some embodiments, the storage and/or memory device comprises one or more physical apparatuses used to store data or programs on a temporary or permanent basis. In some embodiments, the device comprises a volatile memory and requires power to maintain stored information. In some embodiments, the device comprises non-volatile memory and retains stored information when the digital computer is not powered. In some embodiments, the non-volatile memory comprises a flash memory. In some embodiments, the non-volatile memory comprises a dynamic random-access memory (DRAM). In some embodiments, the non-volatile memory comprises a ferroelectric random-access memory (FRAM). In some embodiments, the non-volatile memory comprises a phase-change random access memory (PRAM). In some embodiments, the device comprises a storage device including, by way of non-limiting examples, CD-ROMs, DVDs, flash memory devices, magnetic disk drives, magnetic tapes drives, optical disk drives, and cloud computing-based storage. In some embodiments, the storage and/or memory device comprises a combination of devices, such as those disclosed herein.

In some embodiments, the digital computer comprises a display used for providing visual information to a user. Various types of display may be used. In some embodiments, the display comprises a cathode ray tube (CRT). In some embodiments, the display comprises a liquid crystal display (LCD). In some embodiments, the display comprises a thin film transistor liquid crystal display (TFT-LCD). In some embodiments, the display comprises an organic light-emitting diode (OLED) display. In some embodiments, an OLED display comprises a passive-matrix OLED (PMOLED) or active-matrix OLED (AMOLED) display. In some embodiments, the display comprises a plasma display. In some cases, the display comprises a video projector. In some cases, the display comprises a combination of devices, such as those disclosed herein.

In some embodiments, the digital computer comprises an input device to receive information from a user. Various types of input devices may be used. In some embodiments, the input device comprises a keyboard. In some embodiments, the input device comprises a pointing device including, by way of non-limiting examples, a mouse, trackball, trackpad, joystick, game controller, or stylus. In some embodiments, the input device comprises a touch screen or a multi-touch screen. In some embodiments, the input device comprises a microphone to capture voice or other sound input. In some embodiments, the input device comprises a video camera or other sensor to capture motion or visual input. In some embodiments, the input device comprises a Kinect™, Leap Motion™, or the like. In some embodiments, the input device comprises a combination of devices, such as those disclosed herein.

Figure 1:
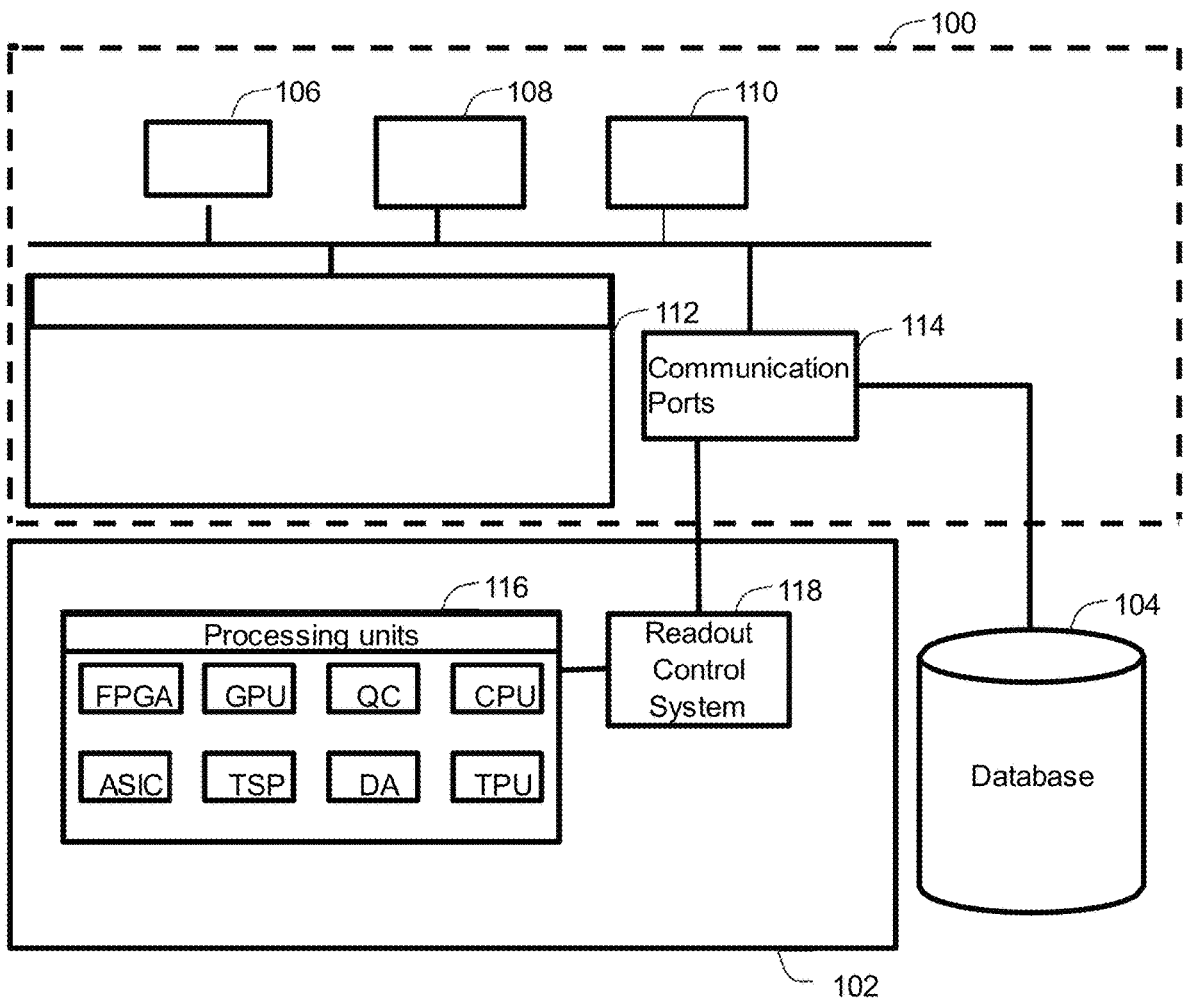
FIG. 1 is a schematic of an example of a computer system for machine learning aided modeling of two interacting structures.

Now referring to FIG. 1, there is shown an example schematic diagram of a system for machine learning aided modeling of two interacting structures. The system can be configured to utilize one or more machine learning (ML) models, e.g., a first differentiable machine learning model, a second differentiable machine learning model, a third differentiable machine learning model, etc.

The system may comprise a digital computer 100. The digital computer may be a digital computer of various types, such as, for example, a digital computer as described elsewhere herein. The digital computer may comprise at least one processing device 106 and at least one memory 112. The at least one memory may comprise a computer program executable by the processing device 106 which may be configured to obtain a request comprising an indication of at least one property of a molecule and a task, to perform inference using at least one machine learning (ML) model using the obtained indication, to perform inference reliability test, if the reliability is satisfactory, to obtain task result using the inference outcomes, if the reliability is not satisfactory, to perform the obtained task to obtain task result, to report electronically the task result.

The system may comprise a computational platform 102 operatively connected to the digital computer 100. The computational platform 102 may comprise at least one processor 116. The at least one processor 116 may be of various types of processors such as, for example, the types of processors as described elsewhere herein. The at least one processor can include Noisy Intermediate-Scale Quantum (NISQ) technology, any quantum device, any high-performance computing device any quantum annealer, any optical computing device, an integrated photonic coherent Ising machine etc. For example, the at least one processor can comprise at least one field-programmable gate array (FPGA), application-specific integrated circuit (ASIC), central processing unit (CPU), graphics processing unit (GPU), tensor processing unit (TPU), tensor streaming processor (TSP), quantum computer, quantum annealer, integrated photonic coherent Ising machine, optical quantum computer, or the like, or any combination thereof. The computational platform 102 may be provided by a cloud computing.

Each component of the system (e.g., the hardware) may be used as part of the system to execute a whole method, or any portion thereof, alone or in combination with other components (e.g., other hardware). In some embodiments, the components may be used for obtaining a request comprising an indication of at least one property of a molecule and a task, performing inference on at least one machine learning (ML) model using the obtained indication, performing inference reliability test, if the reliability is satisfactory obtaining task result using the inference outcomes, if the reliability is not satisfactory, performing the task to obtain task result.

The computational platform 102 may be operatively connected to the digital computer 100. The computational platform may comprise a read-out control system 118. The read-out control system may be configured to read information (e.g., computational results, parameters, etc.) from the at least one processor 116. For example, the read-out control system can be configured to convert data from an FPGA to data usable by a digital computer.

The system may comprise a database 104. The database 104 may be operatively connected to the digital computer 100. The database 104 may be a database of various types. The database 104 may refer to a central repository configured to save the specification of the task and task results. In some embodiments, the database can be, for example, MongoDB. The database 104 may be used to store indications of properties of molecules, corresponding tasks and results thereof. The database 104 may be used to store the task results. The database 104 may be further used to store the output from chemistry discovery toolbox. The database 104 may be further used to store the dataset for training the ML models. The dataset for training ML models may be a subset or complete set of task results. The dataset for training ML models may further be a subset or complete set of the output from chemistry discovery toolbox. The processing device 106 may be further configured to store in the database 104 indications of properties of molecules, corresponding tasks and the results thereof and to read from the database 104 indications of properties of molecules.

The computational platform 102 and the database 104 may be connected to the digital computer 100 over a network. The computational platform, the database, and/or the digital computer can have network communication devices. The network communication devices can enable the computational platform, the database, and/or the digital computer to communicate with each other and with any number of user devices, over a network. The network can be a wired or wireless network. For example, the network can be a fiber optic network, Ethernet® network, a satellite network, a cellular network, a Wi-Fi® network, a Bluetooth® network, or the like. In one or more implementations, the computational platform, the database, and/or digital computer can be several distributed computational platforms, databases, and/or the digital computers that are accessible through the Internet. Such computational platforms, databases, and/or digital computers may be considered cloud computing devices. In some embodiments, the one or more processors of the at least one processor may be located in the cloud.

The at least one processor 116 may comprise one or more virtual machines. The one or more virtual machines may be one or more emulations of one or more computer systems. The virtual machines may be process virtual machines (e.g., virtual machines configured to implement a process in a platform-independent environment). The virtual machines may be systems virtual machines (e.g., virtual machines configured to execute an operating system and related programs). The virtual machine may be configured to emulate a different architecture from the at least one processor. For example, the virtual machine may be configured to emulate a quantum computing architecture on a silicon computer chip. Examples of virtual machines may include, but are not limited to, VMware®, VirtualBox®, Parallels®, QEMU®, Citrix® Hypervisor, Microsoft® Hyper-V®, or the like.

Quantum Computer System

In some embodiments, the systems and methods disclosed herein may be performed with the aid of a quantum computing system. In some embodiments, a computer-implemented method of the present disclosure may be performed at least partially by a quantum computer. In some embodiments, a computing system of the present disclosure may comprise a hybrid computing unit. In some embodiments, a hybrid computing unit may comprise a classical computer and quantum computer. The quantum computer may be configured to perform one or more quantum algorithms for solving a computational problem (e.g., at least a portion of a quantum chemistry simulation).

A quantum device may comprise any device or system used to perform computations using any quantum mechanical phenomenon such as quantum mechanical superposition and quantum mechanical entanglement. Quantum computation, quantum procedure, quantum operation, quantum computer, etc. may comprise any method or system for performing computations using quantum mechanical operations (such as unitary transformations or completely positive trace-preserving (CPTP) maps on quantum channels) on a Hilbert space represented by a quantum device.

The one or more quantum algorithms may be executed using a quantum computer, a quantum-ready computing service, or a quantum-enabled computing service. For instance, the one or more quantum algorithms may be executed using the systems or methods described in U.S. Patent Publication No. 2018/0107526, entitled "METHODS AND SYSETMS FOR QUANTUM READY AND QUANTUM ENABLED COMPUTATIONS", which is entirely incorporated herein by reference. The classical computer may comprise at least one classical processor and computer memory and may be configured to perform one or more classical algorithms for solving a computational problem (e.g., at least a portion of a quantum chemistry simulation).

The digital computer may comprise at least one computer processor and computer memory, wherein the digital computer may include a computer program with instructions executable by the at least one computer processor to render an application. The application may facilitate use of the quantum computer and/or the classical computer by a user.

Some implementations may use quantum computers along with classical computers operating on bits, such as personal desktops, laptops, supercomputers, distributed computing, clusters, cloud-based computing resources, smartphones, or tablets.

The system may comprise an interface for a user. In some embodiments, the interface may comprise an application programming interface (API). The interface may provide a programmatic model that abstracts away (e.g., by hiding from the user) the internal details (e.g., architecture and operations) of the quantum computer. In some embodiments, the interface may minimize a need to update the application programs in response to changing quantum hardware. In some cases, the interface may remain unchanged when the quantum computer has a change in internal structure.

The present disclosure provides systems and methods that may include non-classical (e.g., quantum) computing or use of non-classical (e.g., quantum) computing. Quantum computers may be able to solve certain classes of computational tasks more efficiently than classical computers. However, quantum computation resources may be rare and expensive, and may involve a certain level of expertise to be used efficiently or effectively (e.g., cost-efficiently or cost-effectively). A number of parameters may be tuned in order for a quantum computer to deliver its potential computational power.

Quantum computers (or other types of non-classical computers) may be able to work alongside classical computers as co-processors. A hybrid architecture (e.g., computing system) comprising a classical computer and a quantum computer can be very efficient for addressing complex computational tasks, such as quantum chemistry simulations. Systems and methods disclosed herein may be able to efficiently and accurately decompose or break down a quantum chemistry problem and delegate appropriate components of the quantum chemistry simulations to the quantum computer or the classical computer.

Although the present disclosure has referred to quantum computers, methods and systems of the present disclosure may be employed for use with other types of computers, which may be non-classical computers. Such non-classical computers may comprise quantum computers, hybrid quantum computers, quantum-type computers, or other computers that are not classical computers. Examples of non-classical computers may include, but are not limited to, Hitachi Ising solvers, coherent Ising machines based on optical parameters, and other solvers which utilize different physical phenomena to obtain more efficiency in solving particular classes of problems.

In some embodiments, a quantum computer may comprise one or more adiabatic quantum computers, quantum gate arrays, one-way quantum computers, topological quantum computers, quantum Turing machines, superconductor-based quantum computers, trapped ion quantum computers, trapped atom quantum computers, optical lattices, quantum dot computers, spin-based quantum computers, spatial-based quantum computers, Loss-DiVincenzo quantum computers, nuclear magnetic resonance (NMR) based quantum computers, solution-state NMR quantum computers, solid-state NMR quantum computers, solid-state NMR Kane quantum computers, electrons-on-helium quantum computers, cavity-quantum-electrodynamics based quantum computers, molecular magnet quantum computers, fullerene-based quantum computers, linear optical quantum computers, diamond-based quantum computers, nitrogen vacancy (NV) diamond-based quantum computers, Bose-Einstein condensate-based quantum computers, transistor-based quantum computers, and rare-earth-metal-ion-doped inorganic crystal based quantum computers. A quantum computer may comprise one or more of: quantum annealers, Ising solvers, optical parametric oscillators (OPO), and gate models of quantum computing.

In some embodiments, a non-classical computer of the present disclosure may comprise a noisy intermediate-scale quantum device. Noisy may imply that incomplete control over the qubits is present and the intermediate-scale may refer to the number of qubits which may range from 50 to a few hundreds. Several physical systems made from superconducting qubits, artificial atoms, ion traps are proposed so far as feasible candidates to build NISQ quantum device and ultimately universal quantum computers.

In some embodiments, a classical simulator of the quantum circuit can be used which can run on a classical computer like a MacBook Pro laptop, a Windows laptop, or a Linux laptop. In some embodiments, the classical simulator can run on a cloud computing platform having access to multiple computing nodes in a parallel or distributed manner. In some embodiments, all or a portion of a quantum mechanical energy and/or electronic structure calculation may be performed using the classical simulator.

The methods described herein may be performed on an analogue quantum simulator. An analogue quantum simulator may be a quantum mechanical system consisting of a plurality of manufactured qubits. An analogue quantum simulator may be designed to simulate quantum systems by using physically different but mathematically equivalent or approximately equivalent systems. In an analogue quantum simulator, each qubit may be realized in an ion of strings of trapped atomic ions in linear radiofrequency traps. To each qubit may be coupled a source of bias called a local field bias. The local field biases on the qubits may be programmable and controllable. In some embodiments, a qubit control system comprising a digital processing unit is connected to the system of qubits and is capable of programming and tuning the local field biases on the qubits.

Input Structure

Now referring to FIG. 2, there is illustrated a flowchart of an example of a method for modeling two interacting structures.

At an operation 210, the method 200 may comprise receiving an input structure. The input structure may comprise an interaction region. The input structure may comprise an indication of a structure of a molecule. For example, the input structure may comprise three dimensional coordinates of the atoms on the molecule, a fingerprint, simplified molecular-input line-entry system (SMILES), SMILES arbitrary target specification (SMARTS), or International Chemical Identifier (InChI). In some embodiments, wherein the input structure, the plurality of candidate structures, or both are represented as SMILES structures.

In some embodiments, an indication of a structure of a molecule may be obtained through experimental structure, computational modeling, or a machine learning model such as AlphaFold, RoseTTAFold and NeuralPLexer. In some embodiments, an indication of a structure of a molecule may be obtained through a text-to-molecule task of machine learning models, such as "what is a target protein to cure disease X?"

In some embodiments, the input candidate structure may be represented using latent variables. The latent variables may form a multidimensional latent space. Latent variables may be the variables that are input into a model, and which carry the molecular information (e.g., atom types and positions). Various inputs which can carry the molecular information, and which are differentiable may be used in connection with systems and methods disclosed herein. In some embodiments, the latent space may be unknown or may be known mathematically but convey no physical intuition regarding reasonable geometries or constraints on geometries to conform with reasonable physical structures. Use of a latent space may differ from optimizing physical coordinates, where there is some physical intuition and constraints. For example, optimization of physical coordinates may be constrained such that certain bond lengths or atom spacings are within a reasonable range. Without intuition or physical constraints, the optimization may prove to be much more challenging. For example, the curvature of the optimization parameter with respect to the latent parameters may be different from the curvature with respect to coordinates. In some embodiments, optimization parameters or algorithms that work for coordinates may not work for the latent parameters. When optimization is implemented in a latent space, post processing may be used to impose physical constraints.

In some embodiments, the input candidate structure may be represented using an encoder. For example, the molecular space may be represented using proxy representation. For example, an encoder may comprise a variational auto encoder network, which comprises an encoder network and a decoder network. An example of an implementation of an auto encoder network is provided at R. Gómez-Bombarelli et al., "Automatic Chemical Design Using a Data-Driven Continuous Representation of Molecules," *ACS Cent. Sci.* 2018, 4, 268-276, which is incorporated by reference herein for all purposes. For example, when training, the two networks may work together such that the auto encoder reproduces the input to the network. For example, a molecule is input into the encoder network, the encoder network then outputs values for the latent variables, which indicate where the molecule lives in latent space.

In some embodiments, the input structure is a target structure. In some embodiments, the target structure is a host molecule and wherein the second ligand structure is a guest molecule. In some embodiments, the target structure is a macromolecule or a biomolecule, and wherein the interaction region is an active site. In some embodiments, the macromolecule or the biomolecule is a protein. In some embodiments, the protein is an enzyme. In some embodiments, the macromolecule or the biomolecule is a protein and wherein the ligand structure is selected from the group consisting of another protein, a neurotransmitter, a toxin, a neuropeptide, and a steroid. In some embodiments, the macromolecule or the biomolecule is a protein and wherein the ligand structure is an active pharmaceutical compound. In some embodiments, the macromolecule is a metal-organic framework. In some embodiments, the macromolecule is a polymer. In some embodiments, the target structure is a catalyst.

Candidate Proposal Model

At an operation 220, the method 200 may comprise generating a plurality of candidate structures using a first differentiable machine learning model. The first differentiable machine learning model may be a candidate proposal model as disclosed herein.

In some embodiments, operation 220 comprises exploring a chemical space using one or more metrics selected from the group consisting of synthesizability, uniqueness, novelty, and diversity of proposals. For example, operation 220 may comprises exploring based on novelty, which may comprise finding a new candidate structure not in an initial set. For example, operation 220 may comprises exploring based on uniqueness, which may comprise finding a candidate that has properties that are unlike what is in the set or may comprise finding additional structure like a structure that already exhibits uniqueness. For example, operation 220 may comprises exploring based on diversity, which may comprise generating a candidate set which does not have similar molecules.

In some embodiments, the candidate proposal model is a generative machine learning model. In a generative machine learning model, the exploring a chemical space may comprise generating a new candidate based on one or more steps of the method 200. For example, a new candidate structure may be generated which improves a score or a differentiable scoring function as disclosed herein.

The first differentiable machine learning model may be of various types, such as any machine learning model (ML) described elsewhere herein. In one or more embodiments, the machine learning (ML) model is based on supervised learning. In one or more embodiments, the machine learning (ML) model is based on unsupervised learning. In one or more embodiments, the machine learning (ML) model is based on reinforcement learning. In one or more embodiments, the machine learning (ML) model is based on active learning. In one or more embodiments, the machine learning (ML) model is based on semi-supervised learning. In one or more embodiments, the machine learning (ML) model is based on continuous learning. In one or more embodiments, the machine learning (ML) model is based on transfer learning. In one or more embodiments, modern machine learning (ML) models include an Artificial Neural Network (ANN), a Convolutional Neural Network (CNN), a Graph Neural Network (GNN), a message passing neural network, a transformer network, an autoencoder (AE), a variational autoencoder (VAE), and a Generative Adversarial Network (GAN). These methods utilize automatic differentiation and gradient descent techniques. In one or more embodiments, classical machine learning (ML) modes include a kernel ridge regressor, a random forest regressor, a gradient boosting regressor, a linear regressor, a logistic regressor, a ridge regressor, a lasso regressor, a polynomial regressor, a Bayesian regressor, an elastic net regressor, a principal component regressor, a least squares regressor, a support vector regressor. Some implementations of such ML models may not utilize automatic differentiation and use optimization strategies other than gradient descent. For aforementioned models, ensemble models may be constructed by combining the predictions of 2 or more individual models.

In some embodiments, the first differentiable machine learning model is a generative model. For example, the generative model may be a diffusion-based or a transformer-based generative model. For example, the diffusion-based generative model may be a denoising diffusion probabilistic model. Denoising diffusion probabilistic models may be a class of generative models inspired by non-equilibrium thermodynamics. Briefly, such models can define a Markovian chain of random diffusion steps by slowly adding noise to sample data and then learning the reverse of this process (typically via a neural network) to reconstruct data samples from noise. In some embodiments, the diffusion-based generative model is DiffSBDD.

In some embodiments, the first differentiable machine learning model comprises one or more models selected from the group consisting of DiffSBDD, LiGAN, Deep-LigBuilder, geoLDM, and RELATION. In some embodiments, a differentiable machine learning model of the present disclosure may comprise non-differentiable post-processing steps. LiGAN, DeepLigBuilder, geoLDM, RELATION, etc. may comprise schemes for generative modeling which explore a chemical spaced based on metrics such as synthesizability, uniqueness, novelty, and diversity of proposals. Further information on LiGAN can be found at least at M. Ragoza, T. Masuda, and D. Koes, "Generating 3D molecules conditional on receptor binding sites with deep generative models," *Chem. Sci.,* 2022, 13, 2701-2713, which is incorporated by reference herein for all purposes. Further information on DiffSBDD may be found at least at A. Schneuing et al., "Structure-based Drug Design with Equivariant Diffusion Models" arXiv: 2210.13695v2, which is incorporated by reference herein for all purposes. Further information on DeepLigBuilder can be found at least at Y. Li, J. Pei, and L. Lai, "Structure-based de novo drug design using 3D deep generative models," *Chem. Sci.,* 2021, 12, 13664-13675, which is incorporated by reference herein for all purposes. Further information on RELATION can be found at least at M. Wang et al., "RELATION: A Deep Generative Model for Structure-Based De Novo Drug Design," *J. Med. Chem.* 2022, 65, 13, 9478-9492, which is incorporated by reference herein for all purposes. In some embodiments, the first differentiable machine learning model is a deep learning model.

Interaction Model

At an operation 230, the method 200 may comprise docking one or more candidate structures of the plurality of candidate structures at the interaction region of the input structure using a second differentiable machine learning model to predict a docking geometry. The second machine learning model may comprise an interaction model as disclosed herein. In some embodiments, the docking geometry comprises a predicted pose of the candidate structure with respect to the input structure. Docking can comprise docking between a macromolecule and a ligand. Docking can comprise docking between a protein and a ligand. Docking can comprise docking between a macromolecule and a small molecule, e.g., a neurotransmitter, a toxin, a neuropeptide, a steroid, or otherwise, a pharmaceutical. Docking can comprise docking between a polymer and a ligand. Docking can comprise docking between a polynucleotide and a ligand. Docking can comprise docking between a metal-organic framework and a ligand. Docking can comprise docking between a macromolecule and another macromolecule. Docking can comprise docking between a macromolecule and another macromolecule. Docking can comprise docking between a macromolecule and polynucleotide. Docking can comprise docking between a polynucleotide and another polynucleotide. Docking can comprise docking between a macromolecule and a catalyst, e.g., an enzyme.

The second differentiable machine learning model may comprise use of a machine learning model. The second differentiable model may be configured to approximate the results of a computational chemistry calculation. The second differentiable model may be configured to approximate the results of a quantum chemistry computation (such as DFT, CCSD (T), and FCI), Monte Carlo simulation, molecular docking simulation, or a molecular dynamic simulation. A quantum chemistry calculation may comprise a calculation to predict the electronic structure and molecular properties using quantum mechanics. A molecular mechanical calculation may comprise molecular modeling calculations based on the classical mechanics. A computational chemistry calculation may comprise a computer simulation to assist in solving chemical problems. A computational chemistry calculation may comprise quantum chemistry calculations. A quantum chemistry method may comprise at least one member of the group consisting of Density Functional Theory (DFT), Coupled-Cluster Single-, Double-, and perturbative Triple-excitations (CCSD (T)), Full Configuration Interaction (FCI), Heat-Bath Configuration Interaction (HBCI), Quantum Monte Carlo Full Configuration Interaction (QMCFCI), Density Matrix Embedding Theory (DMET), Fragment Molecular Orbital method (FMO), Incremental Full Configuration Interaction (iFCI), ML-based Schrodinger equation solver such as Paulinet, Hybrid quantum mechanics-molecular mechanics (QM/MM), and ab initio molecular dynamics (AIMD) simulation.

The computational chemistry calculation may further comprise molecular mechanical calculations. In some embodiments, the task may comprise computing energy, computing electronic structure, optimizing molecular geometry, performing the transition state search, performing conformational search, performing molecular similarity search, performing classical molecular dynamics simulation, performing ab initio molecular dynamics simulation, performing protein structure prediction, performing protein binding site prediction, performing virtual screening, performing protein-ligand binding structure prediction, performing free energy perturbation, performing ligand optimization, performing catalyst optimization, performing reaction path prediction, performing synthesizability prediction, performing spectroscopic information prediction, performing reactivity prediction, performing toxicity prediction, performing the binding structure prediction between enzyme and substrate, performing the structure prediction of self-assembled nanomaterials, optimizing the composition of the material, optimizing the experimental condition.

For example, the second differentiable model may predict a binding-pose or a conformation of a candidate structure in an interaction region of the input structure. In an example, the machine learning model may predict the intramolecular forces of protein-bound drugs within molecular dynamics simulations. For example, the machine learning model may predict the binding pose and/or the conformational component of the absolute Gibbs energy of binding for a pair of interacting structures. In some embodiments, the intramolecular forces comprise electrostatic interactions and Van der Waals interactions. The Van der Waals interactions may comprise long range and short range interactions. The Van der Waals interactions may be modeled using a Lennard-Jones model, e.g., which has a short-range repulsive potential and a long-range repulsive potential. Both the short-range and the long-range repulsive potential may be used.

In some embodiments, the second differentiable machine learning model comprises a neural network. In some embodiments, the second differentiable machine learning model comprises a deep learning model. In some embodiments, the second differentiable machine learning model comprises a convolutional neural network. In some embodiments, the second differentiable machine learning model is a generative model. In some embodiments, the generative model is a diffusion-based or a transformer-based generative model.

For example, a neural network may be trained to mimic a QM/MM calculation, a molecular mechanics calculation, a quantum chemistry calculation, etc. In some embodiments, the second differentiable machine learning model comprises one or more models selected from the group consisting of DiffDock, GNINA, E3BIND, and TANKBind. Further information regarding GNINA can be found for example at A. T. McNutt et al., "GNINA 1.0: molecular docking with deep learning," *J. Cheminform.* 13, 43 (2021), which is incorporated by reference herein for all purposes. Further information regarding DiffDock can be found for example at G. Corso et al., "DIFFDOCK: DIFFUSION STEPS, TWISTS, AND TURNS FOR MOLECULAR DOCKING," arXiv: 2210.01776v2, which is incorporated by reference herein for all purposes. Further information regarding E3Bind can be found for example at Y. Zhang et al., "E3BIND: AN END-TO-END EQUIVARIANT NETWORK FOR PROTEIN-LIGAND DOCKING," arXiv: 2210.06069v2, which is incorporated by reference herein for all purposes. Further information regarding SMINA can be found for example at D. R. Koes, M. P. Baumgartner, C. J. Camacho "Lessons Learned in Empirical Scoring with smina from the CSAR 2011 Benchmarking Exercise," *J. Chem. Inf. Model.* 2013, 53, 8, 1893-1904, which is incorporated by reference herein for all purposes.

The at least one machine learning (ML) model may be of various types, such as any machine learning model (ML) described elsewhere herein. In some embodiments, the machine learning (ML) model is based on supervised learning. In some embodiments, the machine learning (ML) model is based on unsupervised learning. In some embodiments, the machine learning (ML) model is based on reinforcement learning. In some embodiments, the machine learning (ML) model is based on active learning. In some embodiments, the machine learning (ML) model is based on semi-supervised learning. In some embodiments, the machine learning (ML) model is based on continuous learning. In some embodiments, the machine learning (ML) model is based on transfer learning. In some embodiments, modern machine learning (ML) models include an Artificial Neural Network (ANN), a Convolutional Neural Network (CNN), a Graph Neural Network (GNN), a message passing neural network, a transformer network, an autoencoder (AE), a variational autoencoder (VAE), and a Generative Adversarial Network (GAN). These methods can utilize automatic differentiation and gradient descent techniques. In some embodiments, classical machine learning (ML) modes include a kernel ridge regressor, a random forest regressor, a gradient boosting regressor, a linear regressor, a logistic regressor, a ridge regressor, a lasso regressor, a polynomial regressor, a Bayesian regressor, an elastic net regressor, a principal component regressor, a least squares regressor, a support vector regressor. Some implementations of such ML models may not utilize automatic differentiation and use optimization strategies other than gradient descent. For the aforementioned models, ensemble models may be constructed by combining the predictions of 2 or more individual models.

Scoring Model

At an operation 240, the method 200 may comprise ranking the one or more candidate structures of the plurality of docked candidate structures using a third differentiable machine learning model to predict a score.

In some embodiments, a score is based on a chemical property of a molecule. In some embodiments, the score comprises an indication of a binding affinity, a volume of the molecule, a dipole moment, or an interaction energy between the input structure and the plurality of candidate structures. In some embodiments, a good candidate between the two interacting structures may comprise one with a good (e.g., net attractive) binding energy. In some embodiments, a good candidate between the two interacting structures may comprise one with a high interaction energy between the two structures. In some embodiments, a good candidate between the two interacting structures may comprise one with a low total volume of the interacting structures, which may indicate a good "fit" with the pocket.

For example, the property of a molecule may further include ground state energy, excited states energies, highest occupied molecular orbital (HOMO)-lowest unoccupied molecular orbital (LUMO) gap, ionization potential, electron affinity, singlet-triplet gap, atomic charge, dipole moment, charge density, spectroscopic properties, peak position at X nm wherein X is the peak position, and binding affinity with a target molecule, equilibrium geometry, transition state geometry, reactivity, hydrophobicity, synthesizability, conformational entropy, and residence time of a molecule interacting with another molecule. In some more embodiments, the property of a molecule may further include effective carrier mass, acoustic wave propagation and elastic constants, the band structure, density of states, and forces on each atom and the stress tensor. In some embodiments, the property of a molecule may further include intercalation voltages, voltage profile, and phase diagram. In some embodiments, the property of a molecule may further include radial distribution functions, diffusion constant, viscosity, and conductivity.

The third differentiable machine learning model may comprise use of a machine learning model. The third differentiable model may be a scoring model. In some embodiments, the third differentiable model is configured to mimic the results of a computational chemistry calculation. In some embodiments, the third differentiable model is configured to approximate the results of a quantum chemistry computation (such as DFT, CCSD (T), and FCI), Monte Carlo simulation, or a molecular dynamic simulation such as free energy perturbation simulation. In some embodiments, the third differentiable model may be configured to approximate experimental results.

A quantum chemistry calculation may comprise a calculation to predict the electronic structure and molecular properties using quantum mechanics. A molecular mechanical calculation may comprise molecular modeling calculations based on the classical mechanics. A computational chemistry calculation may comprise a computer simulation to assist in solving chemical problems. A computational chemistry calculation may comprise quantum chemistry calculations. A quantum chemistry method may comprise at least one member of the group consisting of Density Functional Theory (DFT), Coupled-Cluster Single-, Double-, and perturbative Triple-excitations (CCSD (T)), Full Configuration Interaction (FCI), Heat-Bath Configuration Interaction (HBCI), Quantum Monte Carlo Full Configuration Interaction (QMCFCI), Density Matrix Embedding Theory (DMET), Fragment Molecular Orbital method (FMO), Incremental Full Configuration Interaction (iFCI), ML-based Schrodinger equation solver such as Paulinet, Hybrid quantum mechanics-molecular mechanics (QM/MM), and ab initio molecular dynamics (AIMD) simulation. The computational chemistry calculation may further comprise molecular mechanical calculations.

For example, the third differentiable model may predict a chemical property of a molecule, such as any chemical property of a molecule disclosed herein. For example, the third differentiable model may predict a binding affinity, a volume of the molecule, a dipole moment, or an interaction energy between the input structure and the plurality of candidate structures. In some embodiments, the task may comprise computing energy, computing electronic structure, optimizing molecular geometry, performing the transition state search, performing conformational search, performing molecular similarity search, performing classical molecular dynamics simulation, performing ab initio molecular dynamics simulation, performing protein structure prediction, performing protein binding site prediction, performing virtual screening, performing protein-ligand binding structure prediction, performing free energy perturbation, performing ligand optimization, performing catalyst optimization, performing reaction path prediction, performing synthesizability prediction, performing spectroscopic information prediction, performing reactivity prediction, performing toxicity prediction, performing the binding structure prediction between enzyme and substrate, performing the structure prediction of self-assembled nanomaterials, optimizing the composition of the material, optimizing the experimental condition, or any combination thereof.

In an example, the machine learning model may predict the property of the model based on training data comprising a set of molecules whose relevant property has already been determined experimentally or using a quantum chemical computation. For example, if the property is a binding affinity, the third machine learning model may be trained on a set of molecules with known binding affinities. An example of using a machine learning model to predict a binding energy is provided at least at Lehey, S-L. J. and Rowley, C. N., "Simulating protein-ligand binding with neural network potentials," *Chem. Sci.*, 2020, 11, 2362, which is incorporated by reference herein for all purposes. Lehey and Rowley's model is based at least in part on the ANI model described herein with respect to the section "Interaction Model" herein above. Further information regarding ANI can be found for example at J. S. Smith, O. Isayev and A. E. Roitberg, Chem. Sci., 2017, 8, 3192-3203 or J. S. Smith, B. T. Nebgen, R. Zubatyuk, N. Lubbers, C. Devereux, K. Barros, S. Tretiak, O. Isayev and A. E. Roitberg, Nat. Commun., 2019, 10, 2903, which are each incorporated herein by reference for all purposes.

The at least one machine learning (ML) model may be of various types, such as any machine learning model (ML) described elsewhere herein. In some embodiments, the machine learning (ML) model is based on supervised learning. In some embodiments, the machine learning (ML) model is based on unsupervised learning. In some embodiments, the machine learning (ML) model is based on reinforcement learning. In some embodiments, the machine learning (ML) model is based on active learning. In some embodiments, the machine learning (ML) model is based on semi-supervised learning. In some embodiments, the machine learning (ML) model is based on continuous learning. In some embodiments, the machine learning (ML) model is based on transfer learning. In some embodiments, modern machine learning (ML) models include an Artificial Neural Network (ANN), a Convolutional Neural Network (CNN), a Graph Neural Network (GNN), a message passing neural network, a transformer network, an autoencoder (AE), a variational autoencoder (VAE), and a Generative Adversarial Network (GAN). These methods utilize automatic differentiation and gradient descent techniques. In some embodiments, classical machine learning (ML) modes include a kernel ridge regressor, a random forest regressor, a gradient boosting regressor, a linear regressor, a logistic regressor, a ridge regressor, a lasso regressor, a polynomial regressor, a Bayesian regressor, an elastic net regressor, a principal component regressor, a least squares regressor, a support vector regressor. Some implementations of such ML models may not utilize automatic differentiation and use optimization strategies other than gradient descent. For such aforementioned models, ensemble models may be constructed by combining the predictions of 2 or more individual models.

In some examples, the third machine learning model is the second machine learning model. For example, when the same model is used both for docking and determination of the score, the score may comprise a confidence estimate for the one or more of the plurality of candidate structures. The confidence estimate may comprise a prediction of the root mean squared distance between a candidate structure and a ground truth structure. The root mean squared distance may indicate that the candidate structure is physically close to the ground truth structure and thus "fits" well.

In some embodiments, operation 240 comprises generating a scoring function. The scoring function may be differentiable. The scoring function may be a function of any score disclosed herein, e.g., a root mean square distance, a binding affinity, a volume of the molecule, a dipole moment, or an interaction energy between the input structure and the plurality of candidate structures. The scoring function may be a function of a molecular coordinate. The scoring function may be a function of a latent variable.

Backpropagating

At an operation 250, the method 200 may comprise backpropagating the score to (i) the first differentiable machine learning model to update the plurality of candidate structures or (ii) the second differentiable machine learning model to update the docking geometry.

In some embodiments, operation 250 comprises using the first differentiable machine learning model to generate additional candidate structures. In some embodiments, the additional candidate structures are not in the plurality of candidate structures in operation 220. For example, the first differentiable machine learning structures may be a generative machine learning model which generates one or more additional candidate structures based on the score or the scoring function.

In some embodiments, operation 250 comprises back propagating gradient information. For example, the backpropagating may comprise differentiating the score with respect to the coordinates in the latent space to find a minimum or an approximation thereof and using the minimized coordinates in either the first machine learning model, the second machine learning model, or both. For example, backpropagating may comprise evaluating each derivative collectively or sequence. Each derivative may be attached via chain rule and therefore gradients may be computed backwards up until the gradients of the latent variables. Once these gradients are known, an optimization algorithm may be implemented to update the latent variables. In an example, where the first machine learning model is to be updated, the minimized variables can go into the first machine learning model, and the output of that can go into second machine learning model, etc. In some embodiments, the derivative of the score can be calculated with respect to the output of the second machine learning model, and those coordinates may be used to update the third machine learning model (e.g., bypassing the first).

An example implementation of backpropagating is provided in the pseudo-code below:

```
import torch
#in an example, these are torch ML models
model_1, model_2, model_3 = Model1( ), Model2( ), Model3( )
n_steps = 100 # the number of optimization steps, the number 100 being
provided for example purposes
alpha = 0.1 # parameter for gradient descent
for _ in range(n_steps):
# mol depends on latents
latents, mol = Model1( )
# dock it
docked_mol = Model2(mol)
# score it
score = Model3(docked_mol)
grad = torch.autograd.grad(score, latents)
latents = latents – alpha * grad
```

In some embodiments, the method 200 further comprises outputting a list of the updated plurality of candidates. In some embodiments, the method 200 further comprises outputting an optimized candidate structure. In some embodiments, the method 200 further comprises outputting a candidate structure with improved binding to the interaction site.

While backpropagating is provided as an example of propagating information or gradients through a neural network, other propagation methods also may be suitable. For example, in some embodiments, forward propagation may be used.

Systems

Figure 3:
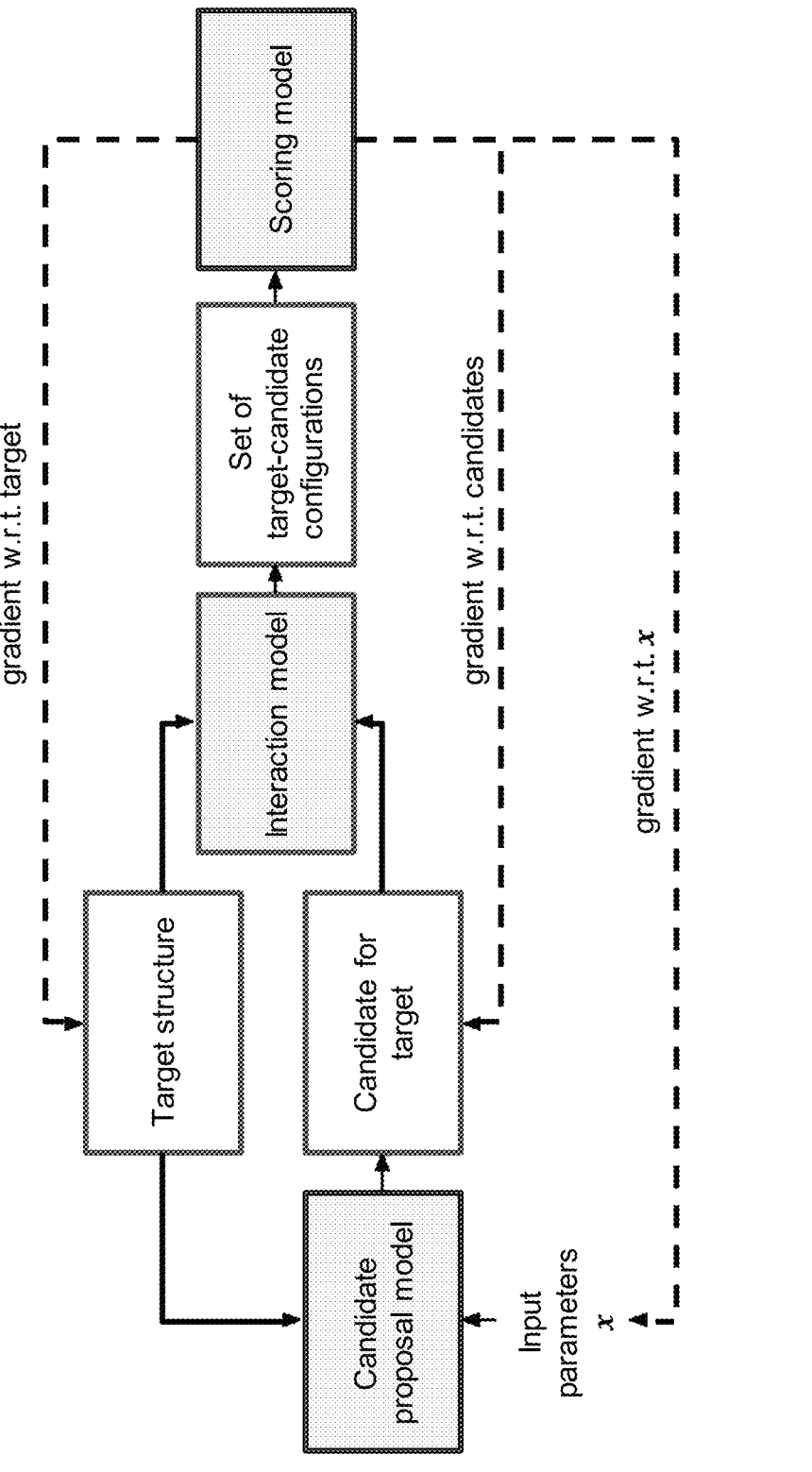
FIG. 3 illustrates a schematic of an example of a system for modeling two interacting structures.
Figure 4:
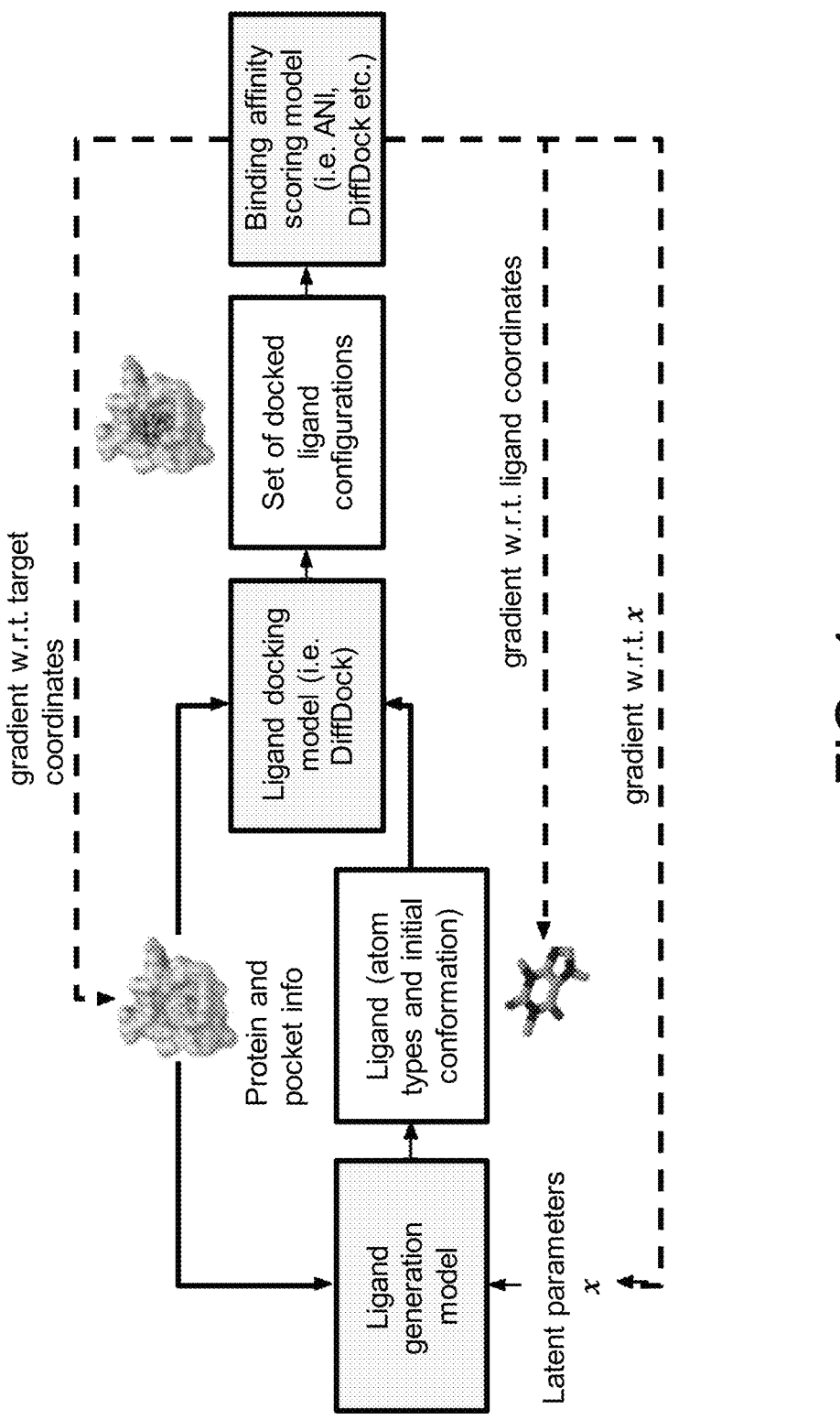
FIG. 4 illustrate a schematic of an example of the pipeline disclosed herein for protein-ligand binding.
Figure 5A:
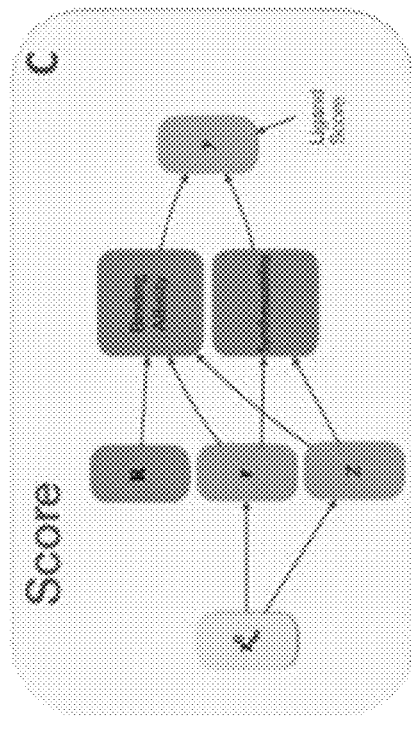
FIGS. 5A-5B illustrates a schematic of an example of a pipeline disclosed herein for protein-ligand binding.
Figure 5C:
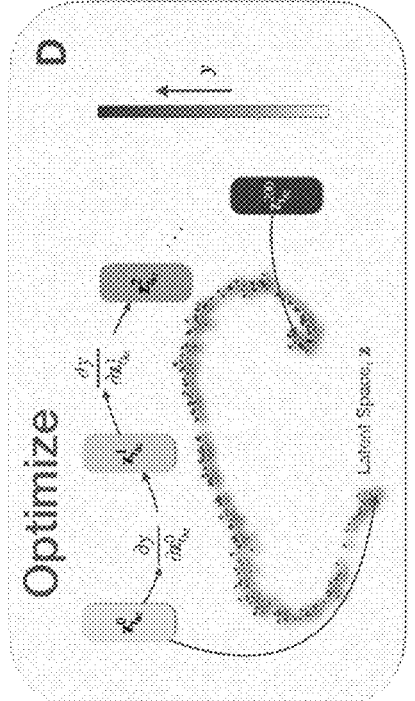
FIG. 5C illustrates how the ligand is scored by evaluating the binding affinity, synthesizability, or both.
Figure 5B:
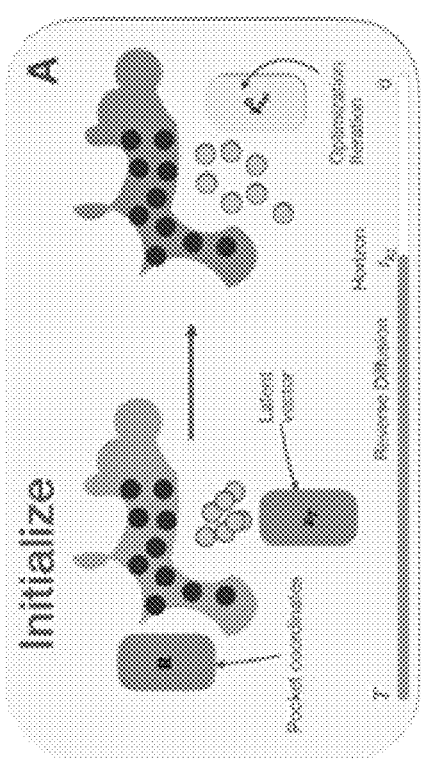
Figure 5D:
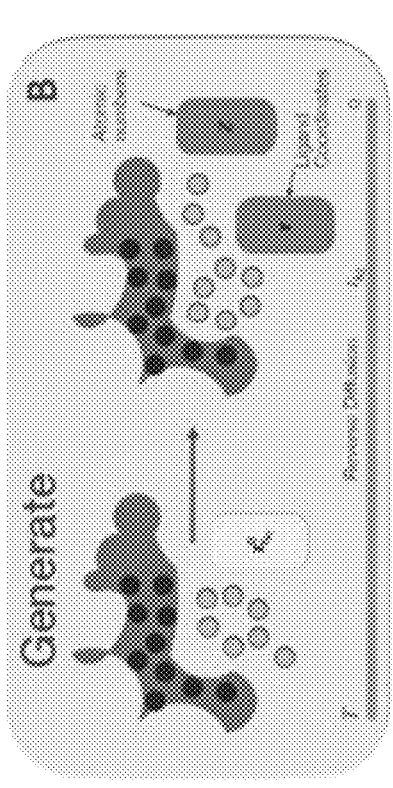
FIG. 5D illustrates how the ligand score is differentiated with respect to the latent vector $$z_t^0,$$

Now referring to FIG. 3 and FIG. 4, there are illustrated schematics of examples of a system for modeling two interacting structures.

Referring to FIG. 3, a system may comprise a candidate proposal model, an interaction model, and a scoring model. The candidate proposal model may comprise any example, variation, case, or embodiment described herein with respect to the section "Candidate Proposal Model." The interaction model may comprise any example, variation, case, or embodiment described herein with respect to the section "Interaction Model." The scoring model may comprise any example, variation, case, or embodiment described herein with respect to the section "Scoring Model."

The system shown in FIG. 3 may be implemented on a computing system, for example, the computing systems described herein with respect to the section "Computing System." In some embodiments, digital computer 100 may be configured to implement various operations of the method 200. In some embodiments, digital computer 100 may be configured to implement a candidate proposal model, an interaction model, and a scoring model disclosed herein. In some embodiments, one or more of a candidate proposal model, an interaction model, and a scoring model may directed to processing units 116. For example, one model may be implemented on a first processing unit (e.g., an FPGA, a GPU, a QC, a CPU, an ASIC, etc.) and another model may be implemented on a second processing unit (e.g., an FPGA, a GPU, a QC, a CPU, an ASIC, etc.). In some embodiments, parts of a model, for example, one or more nodes or groups of nodes of a neural network, may be implemented on a first processing unit (e.g., an FPGA, a GPU, a QC, a CPU, an ASIC, etc.) and another part of a model may be implemented on a second processing unit (e.g., an FPGA, a GPU, a QC, a CPU, an ASIC, etc.).

As shown in FIG. 3, the candidate proposal model may generate a candidate for a target, which may be passed to the interaction model to find a pose. The interaction model may create a set of target candidate configurations. The set of target candidate configurations may be scored.

As described herein above, in some embodiments, the score may be differentiated with respect to the input parameters (e.g., latent variables herein) and backpropagated to find a target structure. In some embodiments, the score may be differentiated with respect to the candidate structures and back propagated to find an improved pose in the interaction region.

In some embodiments, the score may be differentiated with respect to the target structure and back propagated to find a better conformation of the input structure. For example, if a candidate with a high binding affinity is known. Then the model described herein may be used to improve the input structure (e.g., a protein folding).

Two Interacting Structures

The systems and method disclosed herein may be useful for various interacting structures. In some embodiments, the input structure is a host molecule, and plurality of candidate structures comprises a guest molecule. In some embodiments, the input structure is a macromolecule or a biomolecule, the plurality of candidate structures comprises a ligand, and the interaction region is an active site. In some embodiments, the macromolecule or the biomolecule is a protein. In some embodiments, the protein is an enzyme. In some cases, the macromolecule or the biomolecule is a protein, and the ligand is selected from the group consisting of another protein, a neurotransmitter, a toxin, a neuropeptide, and a steroid. In some embodiments, the macromolecule or the biomolecule is a protein, and the ligand is an active pharmaceutical compound. In some embodiments, the macromolecule is a metal-organic framework. In some embodiments, the macromolecule is a polymer. In some cases, the input structure is a catalyst. In some embodiments, the input structure is a metal organic framework, and the plurality of candidate structures comprises a hazardous molecule such as Perfluoroalkyl and Polyfluoroalkyl Substances (PFAS). In some embodiments, the input structure is the anode or cathode material of a battery, and the plurality of candidate structures comprises an electrolyte. In some embodiments, the input structure is a grain or crystallite of an alloy, and the plurality of candidate structures comprises another grain or crystallite of the same alloy, together forming a grain boundary.

In some embodiments, modeling two interacting structures comprises performing conformational search, performing protein structure prediction, performing protein binding site prediction, performing virtual screening of drugs, performing protein-ligand binding structure prediction, performing ligand optimization, performing catalyst optimization, performing reactivity prediction, performing toxicity prediction, performing the binding structure prediction between enzyme and substrate, performing the structure prediction of self-assembled nanomaterials, etc.

FIG. 4 illustrates an example of the pipeline disclosed herein for protein-ligand binding. As shown in FIG. 4, the candidate proposal model may be a ligand generation model which generates a candidate for a target ligand. The candidate may be passed to the interaction model to find a pose. The interaction model may be a protein docking model. The protein docking model may create a set of docked ligand configurations. The set of docked ligand configurations may be scored. The score may be a binding affinity scoring model, e.g., ANI, DiffDock, etc.

As described herein above, in some embodiments, the score may be differentiated with respect to the input parameters (e.g., latent variables herein) and backpropagated to find a target ligand structure. In some embodiments, the score may be differentiated with respect to the candidate ligand structures and back propagated to find an improved docked ligand pose in the protein pocket.

In some embodiments, the score may be differentiated with respect to the target ligand structure and back propagated to find a better conformation of the input protein structure, for example, if a ligand with a high binding affinity is known. Then the model described herein may be used to improve the input structure (e.g., a protein folding or a cryptic pocket formation of a protein, or a composition and self-assembled structure of metal organic frameworks).

In another example, the systems and methods disclosed herein could be adapted for organic crystal structure prediction by changing the role of the second machine learning model from generating protein-ligand docked poses to generating candidate molecular crystal structures.

In another example, the systems and methods disclosed herein could be adapted for more general chemical compounds screening, such as ligand-based virtual screening.

Structure in an Environment

The systems and method disclosed herein may be useful for generating a structure for a predetermined environment. The predetermined environment can be, e.g., vacuum, a gas phase media, a solvent media, or a solid surface. The systems and methods disclosed herein can generate the structure such that it meets or exceeds a threshold value for a property of interest.

For example, the property of interest is solvation energy in a solvent media. A differentiable machine learning model can be created to predict the solvation energy given a molecule structure. The machine learning model can be used to propagate gradients to a generative model that is configured generate a variety of candidate structures. By propagating such gradients, the generative model can be steered towards generating candidate structures that are more likely to meet a certain objective or criteria for solvation energy. It shall be understood that solvation energy is just one example of a property that could be of interest, and various other objectives may be used. Other objectives can be toxicity, reactivity, stability, synthetic accessibility, crystal structures, or any combination thereof.

In some embodiments, the structure is a macromolecule or a biomolecule. In some embodiments, the structure is a ligand. In some embodiments, the macromolecule or the biomolecule is a protein. In some embodiments, the protein is an enzyme. In some cases, the ligand is selected from the group consisting of another protein, a neurotransmitter, a toxin, a neuropeptide, and a steroid. In some embodiments, the ligand is an active pharmaceutical compound. In some embodiments, the macromolecule is a polymer. In some embodiments, the structure is a catalyst. In some embodiments, the structure is a metal organic framework. In some embodiments, the structure is a compound that is used as a substitute to the hazardous molecule such as Perfluoroalkyl and Polyfluoroalkyl Substances (PFAS). In some embodiments, the structure is the anode or cathode material of a battery. In some embodiments, the structure is an electrolyte of a battery. In some embodiments, the structure is a grain or crystallite of an alloy.

Generating and Optimizing Compounds

In an aspect, the present disclosure provides, a method of optimizing reference compounds. In some embodiments, a reference compound may be an initial candidate for a particular application, e.g., binding to a target protein. However, it may be the reference compound may not be perfectly suitable for the application. In such instances, optimizing the reference compound such that it satisfies a plurality of objectives, e.g., ADMET, solubility, synthetic accessibility, etc., may be useful for screening a number of related compounds. In some embodiments, the method can comprise obtaining a target structure. In some embodiments, the method can comprise a first ligand structure. In some embodiments, the method can comprise generating a latent vector based on the first ligand structure. In some embodiments, the method can comprise processing the latent vector. In some embodiments, the processing can be performed with or without SE(3) equivariance or other symmetries. In some embodiments, the processing generates a second ligand structure based on (i) the target structure and/or (ii) a score comprising a measure of affinity between the target structure and the second ligand structure. In some embodiments, the score is differentiable with respect to a definition. In some embodiments, the definition can comprise particle positions and/or atom types. In some embodiments, the method can comprise generating a report comprising an identifier for the second ligand structure.

In another aspect, the present disclosure provides, a processor comprising a communications interface configured to connect to a computing system over a network. In some embodiments, the processor is configured to receive an indication of a problem from a user comprising a target structure and a first ligand structure. In some embodiments, the processor is configured to direct instructions via the communications interface to generate a latent vector based on the first ligand structure. In some embodiments, the computing system is configured to process the latent vector with or without SE(3) equivariance or other symmetries. In some embodiments, the computing system is configured to generate a second ligand structure. The generation can be based on (i) the target structure and/or (ii) a score comprising a measure of affinity between the target structure and the second ligand structure. In some embodiments, the score is differentiable with respect to a definition. In some embodiments, the definition can comprise particle positions and/or atom types. In some embodiments, the processor is configured to receive an output via the communications interface. In some embodiment, the output comprises a report comprising an identifier for the second ligand structure.

In another aspect, the present disclosure provides, a processor comprising a communications interface configured to connect to a control system over a network. In some embodiments, the processor is configured to receive instructions via the communications interface. In some embodiments, the instructions comprise an indication of a problem comprising a target structure and/or a first ligand structure from a control system. In some embodiments, the processor is configured to implement instructions. In some embodiments, the instructions are configured to generate a latent vector based on the first ligand structure. In some embodiments, the instructions are configured to process the latent vector, with or without SE(3) equivariance or other symmetries. In some embodiments, the instructions are configured to generate a second ligand structure based on (i) the target structure and/or (ii) a score comprising a measure of affinity between the target structure and the second ligand structure. In some embodiments, the score is differentiable with respect to a definition. In some embodiments, the definition comprises particle positions or atom types. In some embodiments, the instructions are configured to direct an output to via the communications interface. In some embodiments, the output comprises a report comprising an identifier for the second ligand structure.

In some embodiments, the target structure is generated using a machine learning model. In some embodiments, an interaction region of the target structure is generated using a machine learning model. In some embodiments, the machine learning model further generates the second ligand structure.

In some embodiments, the first ligand structure is a hit compound or a lead compound. In some embodiments, the first ligand structure is configured to interact with the target structure. In some embodiments, the first ligand structure is configured to bind to the target structure. In some embodiments, the second ligand structure is a lead compound or a lead-optimized compound. In some embodiments, the second ligand structure is configured to interact with the target structure. In some embodiments, the second ligand structure is configured to bind to the target structure. In some embodiments, the target structure is a protein structure. In some embodiments, the target structure comprises an interaction region. In some embodiments, the interaction region comprises a protein pocket. In some embodiments, the first ligand structure is a small molecule, a nucleic acid, a peptide, or a protein.

In some embodiments, the latent vector is a noisy latent vector. In some embodiments, the generating comprises noising an initial latent vector of the first ligand structure. In some embodiments, the noising comprises diffusing the initial latent vector of the first ligand structure. In some embodiments, the noising comprises stochastic noising. In some embodiments, the processing comprises denoising the latent vector. In some embodiments, the denoising comprises reverse diffusing the latent vector or a noisy ligand structure thereof. In some embodiments, the processing is performed using a neural network. In some embodiments, the neural network is a diffusion model. In some embodiments, the target structure is fixed during the denoising. In some embodiments, the target structure is movable during the denoising.

In some embodiments, the measure of affinity is a measure of binding affinity. In some embodiments, the measure of affinity accounts for potential energy of the target structure and the ligand structure. In some embodiments, the measure of affinity accounts for free energy of the target structure and the ligand structure. In some embodiments, the particle positions comprise atom positions, coarse-grained particle positions, residue positions, or any combination thereof. In some embodiments, the particle positions comprise coordinates. In some embodiments, the measure of affinity is based on a force-field, a quantum chemical calculation, or a free energy perturbation calculation. In some embodiments, the processing is further based on a measure of synthetic accessibility of the second ligand structure. In some embodiments, the measure of synthetic accessibility is based on or not based on an equivariant neural network. In some embodiments, the processing is further based on a measure of feasibility that is based on an equivariant neural network. In some embodiments, the processing is further based on a measure of feasibility that is differentiable with respect to a definition. In some embodiments, the definition comprises particle positions or atom types. In some embodiments, the measure of feasibility comprises measure of absorption, distribution, metabolism, and excretion-toxicity (ADMET).

In another aspect, the present disclosure provides, a method of generating lead compounds. In some embodiments, generating compounds for a particular application may involve de novo generation. For instance, a protein target for treating a drug may be known, however, a drug candidate that can bind to or affect the protein may be unknown. In such cases, generating a structure of a drug molecule, without a prior known candidate molecule, can be useful. In some embodiments, the method comprises obtaining a target structure and/or a latent vector. In some embodiments, the method comprises processing the latent vector to generate an intermediate latent vector. In some embodiments, the method comprises processing the intermediate latent vector to generate a ligand structure. In some embodiments, the method comprises generating a report comprising an identifier for the ligand structure. In some embodiments, the processing is performed with or without SE(3) equivariance or other symmetries. In some embodiments, the processing is based on (i) the target structure and/or (ii) a measure of affinity between the target structure and the ligand structure. In some embodiments, the measure of binding affinity is differentiable with respect to a definition. In some embodiments, the definition comprises particle positions or atom types.

In another aspect, the present disclosure provides, a processor comprising a communications interface configured to connect to a computing system over a network. In some embodiments, the processor is configured to receive an indication of a problem from a user comprising a target structure and a latent vector. In some embodiments, the processor is configured to direct instructions via the communications interface to process the latent vector to generate an intermediate latent vector and to process the intermediate latent vector to generate a ligand structure. In some embodiments, the computing system is configured to perform the processing, with or without SE(3) equivariance or other symmetries. In some embodiments, the processing is based on (i) the target structure and/or (ii) a measure of affinity between the target structure and the ligand structure. In some embodiments, the measure of binding affinity is differentiable with respect to a definition. In some embodiments, the definition comprises particle positions or atom types. In some embodiments, the computing system is configured to receive an output via the communications interface. In some embodiments, the output comprises a report comprising an identifier for the ligand structure.

In another aspect, the present disclosure provides, a processor comprising a communications interface configured to connect to a control system over a network, the processor configured to receive instructions via the communications interface. In some embodiments, the instructions comprise an indication of a problem comprising a target structure and/or a latent vector from a control system. In some embodiments, the processor is configured to implement instructions to process the latent vector to generate an intermediate latent vector. In some embodiments, the processor is configured to process the intermediate latent vector to generate a ligand structure, with or without SE(3) equivariance or other symmetries. In some embodiments, the processing is based on (i) the target structure and/or (ii) a measure of affinity between the target structure and the ligand structure. In some embodiments, the measure of binding affinity is differentiable with respect to a definition comprising particle positions or atom types. In some embodiments, the processor is configured to direct an output to via the communications interface. In some embodiments, the output comprises a report comprising an identifier for the ligand structure.

In some embodiments, the latent vector is a random latent vector. In some embodiments, the intermediate latent vector corresponds to a noisy ligand structure. In some embodiments, the processing in (c) is performed a plurality of times to generate a plurality of ligand structures.

In some embodiments, a gradient of the measure of affinity is propagatable to the intermediate latent vector. In some embodiments, the processing in (b) and (c) are based on a measure of synthesizability of the ligand structure. In some embodiments, a gradient of the measure of synthesizability is propagatable to the intermediate latent vector.

In some embodiments, the target structure is generated using a machine learning model. In some embodiments, an interaction region of the target structure is generated using a machine learning model. In some embodiments, the latent vector is generated using a machine learning model. In some embodiments, the ligand structure is configured to interact with the target structure. In some embodiments, the ligand structure is configured to bind to the target structure. In some embodiments, the target structure is a protein structure. In some embodiments, the target structure comprises an interaction region. In some embodiments, the interaction region comprises a protein pocket. In some embodiments, the ligand structure is a small molecule, a nucleic acid, a peptide, or a protein.

In some embodiments, the processing in (b) comprises denoising the latent vector. In some embodiments, the denoising comprises reverse diffusing the latent vector. In some embodiments, the processing in (b) is performed using a neural network. In some embodiments, the neural network is a diffusion model. In some embodiments, the target structure is fixed during the denoising. In some embodiments, the target structure is movable during the denoising.

In some embodiments, the measure of affinity is a measure of binding affinity. In some embodiments, the measure of affinity accounts for potential energy of the target structure and the ligand structure. In some embodiments, the measure of affinity accounts for free energy of the target structure and the ligand structure. In some embodiments, the particle positions comprise atom positions, coarse-grained particle positions, residue positions, or any combination thereof. In some embodiments, the particle positions comprise coordinates. In some embodiments, the measure of affinity is based on a force-field, a quantum chemical calculation, or a free energy perturbation calculation.

In some embodiments, the processing in (b) and (c) are further based on a measure of synthetic accessibility of the ligand structure. In some embodiments, the measure of synthetic accessibility is based on or not on an equivariant neural network. In some embodiments, the processing in (b) is further based on a measure of feasibility that is based on an equivariant neural network. In some embodiments, the processing in (b) is further based on a measure of feasibility that is differentiable with respect to a definition comprising particle positions or atom types. In some embodiments, the measure of feasibility comprises measure of absorption, distribution, metabolism, and excretion-toxicity (ADMET).

In some embodiments, the method further comprises synthesizing the ligand structure. In some embodiments, the method further comprises performing a binding assay to detect a binding event between the target structure and the ligand structure. In some embodiments, the method further comprises performing the method using the ligand structure to generate the latent vector.

In some embodiments, the target structure is a host molecule and wherein the ligand structure is a guest molecule. In some embodiments, the target structure is a macromolecule or a biomolecule, and wherein the interaction region is an active site. In some embodiments, the macromolecule or the biomolecule is a protein. In some embodiments, the protein is an enzyme. In some embodiments, the macromolecule or the biomolecule is a protein and wherein the ligand structure is selected from the group consisting of another protein, a neurotransmitter, a toxin, a neuropeptide, and a steroid. In some embodiments, the macromolecule or the biomolecule is a protein and wherein the ligand structure is an active pharmaceutical compound. In some embodiments, the macromolecule is a metal-organic framework. In some embodiments, the macromolecule is a polymer. In some embodiments, the target structure is a catalyst.

In some embodiments, the method further comprises synthesizing the second ligand structure. In some embodiments, the method further comprises performing a binding assay to detect a binding event between the target structure and the second ligand structure. In some embodiments, the method further comprises performing the method using the second ligand structure as the first ligand structure.

LIST OF EMBODIMENTS

The following list of embodiments of the invention are to be considered as disclosing various features of the invention, which features can be considered to be specific to the particular embodiment under which they are discussed, or which are combinable with the various other features as listed in other embodiments. Thus, simply because a feature is discussed under one particular embodiment does not necessarily limit the use of that feature to that embodiment.

Embodiment 1. A method for machine learning aided modeling of two interacting structures, the method comprising: (a) receiving an input structure comprising an interaction region; (b) generating a plurality of candidate structures using a first differentiable machine learning model; (c) docking one or more candidate structures of the plurality of candidate structures at the interaction region of the input structure using a second differentiable machine learning model to predict a docking geometry; (d) ranking the one or more candidate structures of the plurality of candidate structures docked in (c) using a third differentiable machine learning model or differentiable scoring function to predict a score; and (e) propagating the score to (i) the first differentiable machine learning model to update the plurality of candidate structures or (ii) the second differentiable machine learning model to update the docking geometry.

Embodiment 2. The method of Embodiment 1, further comprising outputting a list of the plurality of candidates updated in (e).

Embodiment 3. The method of Embodiment 1 or 2, wherein the input structure is a host molecule and wherein the plurality of candidate structures comprises a guest molecule.

Embodiment 4. The method of any one of Embodiments 1-3, wherein the input structure is a macromolecule or a biomolecule, wherein the plurality of candidate structures comprises a ligand, and wherein the interaction region is an active site.

Embodiment 5. The method of Embodiment 4, wherein the macromolecule or the biomolecule is a protein.

Embodiment 6. The method of Embodiment 5, wherein the protein is an enzyme.

Embodiment 7. The method of any one of Embodiments 4-6, wherein the macromolecule or the biomolecule is a protein and wherein the ligand is selected from the group consisting of another protein, a neurotransmitter, a toxin, a neuropeptide, and a steroid.

Embodiment 8. The method of any one of Embodiments 4-7, wherein the macromolecule or the biomolecule is a protein and wherein the ligand is an active pharmaceutical compound.

Embodiment 9. The method of Embodiment 4, wherein the macromolecule is a metal-organic framework.

Embodiment 10. The method of Embodiment 4, wherein the macromolecule is a polymer.

Embodiment 11. The method of Embodiment 1, wherein the input structure is a catalyst.

Embodiment 12. The method of any one of Embodiments 1-11, wherein the third machine learning model is the second machine learning model, and wherein the score comprises a confidence estimate for the one or more candidate structures docked in (c).

Embodiment 13. The method of Embodiment 12, wherein the confidence estimate is a prediction of the root mean squared distance between a candidate structure and a ground-truth structure.

Embodiment 14. The method of Embodiment 13, wherein the ground-truth structure is an experimentally determined structure.

Embodiment 15. The method of any one of Embodiments 1-14, wherein the second machine learning model is the first machine learning model, and wherein the generating comprises generating directly into the interaction region of the input structure.

Embodiment 16. The method of any one of Embodiments 1-15, wherein the interaction region is determined by the second machine learning model.

Embodiment 17. The method of any one of Embodiments 1-16, wherein the interaction region is determined by a fourth machine learning model.

Embodiment 18. The method of any one of Embodiments 1-17, wherein the score comprises an indication of a binding affinity, a volume of a molecule, a dipole moment, or an interaction energy between the input structure and the plurality of candidate structures.

Embodiment 19. The method of any one of Embodiments 1-18, wherein (d) comprises generating a scoring function, wherein the scoring function is differentiable.

Embodiment 20. The method of any one of Embodiments 1-19, wherein (b) comprises exploring a chemical space using one or more metrics selected from the group consisting of synthesizability, uniqueness, novelty, and diversity of proposals.

Embodiment 21. The method of any one of Embodiments 1-20, wherein the first differentiable machine learning model is a generative model.

Embodiment 22. The method of Embodiment 21, wherein the generative model is a diffusion-based or a transformer-based generative model.

Embodiment 23. The method of Embodiment 22, wherein the diffusion-based generative model is a denoising diffusion probabilistic model.

Embodiment 24. The method of any one of Embodiments 1-23, wherein the first differentiable machine learning model is a deep learning model.

Embodiment 25. The method of any one of Embodiments 1-24, wherein the first differentiable machine learning model comprises one or more models selected from the group consisting of DiffSBDD, LiGAN, DeepLigBuilder, geoLDM, and RELATION.

Embodiment 26. The method of any one of Embodiments 1-25, wherein the input structure, the plurality of candidate structures, or both are represented as SMILES structures.

Embodiment 27. The method of any one of Embodiments 1-26, wherein the docking geometry comprises a predicted pose of a candidate structure with respect to the input structure.

Embodiment 28. The method of any one of Embodiments 1-27, wherein the second differentiable machine learning model is a generative model.

Embodiment 29. The method of Embodiment 28, wherein the generative model is a diffusion-based or a transformer-based generative model.

Embodiment 30. The method of any one of Embodiments 1-29, wherein the second differentiable machine learning model comprises one or more models selected from the group consisting of DiffDock, GNINA, E3BIND.

Embodiment 31. The method of any one of Embodiments 1-30, wherein the third differentiable machine learning model or differentiable scoring function comprises one or more models from the group consisting of ANI, Vina, Vinardo, Smina.

Embodiment 32. The method of any one of Embodiments 1-31, wherein (e) comprises using the first differentiable machine learning model to generate additional candidate structures, wherein the additional candidate structures are not in the plurality of candidate structures in (b).

Embodiment 33. The method of any one of Embodiments 1-32, wherein (e) comprises backpropagating gradient information.

Embodiment 34. The method of any one of Embodiments 1-32, wherein (e) comprises forward propagating gradient information.

Embodiment 35. The method of any one of Embodiments 1-34, further comprising estimating an inference reliability from at least one of differentiable machine learning models.

Embodiment 36. The method of Embodiment 35, further comprising determining that the inference reliability is less than a threshold, and recalculating an output of the at least one differentiable model using an underlying differentiable method on which the at least one of the differentiable machine learning models is trained or another differentiable method.

Embodiment 37. The method of Embodiment 36, further comprising retraining the differentiable machine learning model based at least in part on an output from the underlying differentiable machine learning model and a gradient of the underlying differentiable machine learning model to improve the inference reliability.

Embodiment 38. A system for machine learning aided modeling of two interacting structures, the system comprising a non-transitory computer-readable medium with instructions stored thereon which when executed by a processor are configured to: (a) receive an input structure comprising an interaction region; (b) generate a plurality of candidate structures using a first differentiable machine learning model; (c) dock one or more candidate structures of the plurality of candidate structures at the interaction region of the input structure using a second differentiable machine learning model to predict a docking geometry; (d) rank the one or more candidate structures of the plurality of candidate structures docked in (c) using a third differentiable machine learning model or a differentiable scoring function to predict a score; and (e) propagate the score to (i) the first differentiable machine learning model to update the plurality of candidate structures or (ii) the second differentiable machine learning model to update the docking geometry.

Embodiment 39. The system of Embodiment 38, wherein the processor is further configured to output a list of the plurality of candidates updated in (e).

Embodiment 40. The system of Embodiment 38 or 39, wherein the input structure is a host molecule and wherein the plurality of candidate structures comprises a guest molecule.

Embodiment 41. The system of any one of Embodiments 38-40, wherein the input structure is a macromolecule or a biomolecule, wherein the plurality of candidate structures comprises a ligand, and wherein the interaction region is an active site.

Embodiment 42. The system of Embodiment 41, wherein the macromolecule or the biomolecule is a protein.

Embodiment 43. The system of Embodiment 42, wherein the protein is an enzyme.

Embodiment 44. The system of any one of Embodiments 41-43, wherein the macromolecule or the biomolecule is a protein and wherein the ligand is selected from the group consisting of another protein, a neurotransmitter, a toxin, a neuropeptide, and a steroid.

Embodiment 45. The system of any one of Embodiments 41-44, wherein the macromolecule or the biomolecule is a protein and wherein the ligand is an active pharmaceutical compound.

Embodiment 46. The system of Embodiment 41, wherein the macromolecule is a metal-organic framework.

Embodiment 47. The system of Embodiment 41, wherein the macromolecule is a polymer.

Embodiment 48. The system of Embodiment 35, wherein the input structure is a catalyst.

Embodiment 49. The system of any one of Embodiments 38-48, wherein the third machine learning model is the second machine learning model, and wherein the score comprises a confidence estimate for the one or more candidate structures docked in (c).

Embodiment 50. The system of Embodiment 49, wherein the confidence estimate is a prediction of the root mean squared distance between a candidate structure and a ground truth structure.

Embodiment 51. The system of Embodiment 50, wherein the ground-truth structure is an experimentally determined structure.

Embodiment 52. The system of any one of Embodiments 38-51, wherein the second machine learning model is the first machine learning model, and wherein the generating comprises generating directly into the interaction region of the input structure.

Embodiment 53. The system of any one of Embodiments 38-52, wherein the interaction region is determined by the second machine learning model.

Embodiment 54. The system of any one of Embodiments 38-53, wherein the interaction region is determined by a fourth machine learning model.

Embodiment 55. The system of any one of Embodiments 38-54, wherein the score comprises an indication of a binding affinity, a volume of a molecule, a dipole moment, or an interaction energy between the input structure and the plurality of candidate structures.

Embodiment 56. The system of any one of Embodiments 38-55, wherein at (d) the processor is further configured to generate a scoring function, wherein the scoring function is differentiable.

Embodiment 57. The system of any one of Embodiments 38-56, wherein at (b) the processor is further configured to explore a chemical space using one or more metrics selected from the group consisting of synthesizability, uniqueness, novelty, and diversity of proposals.

Embodiment 58. The system of Embodiment 57, wherein the first differentiable machine learning model is a generative model.

Embodiment 59. The system of Embodiment 58, wherein the generative model is a diffusion-based or a transformer-based generative model.

Embodiment 60. The system of Embodiment 59, wherein the diffusion-based generative model is a denoising diffusion probabilistic model.

Embodiment 61. The system of any one of Embodiments 38-60, wherein the first differentiable machine learning model is a deep learning model.

Embodiment 62. The system of any one of Embodiments 38-61, wherein the first differentiable machine learning model comprises one or more models selected from the group consisting of DiffSBDD, LiGAN, DeepLigBuilder, geoLDM, and RELATION.

Embodiment 63. The system of any one of Embodiments 38-62, wherein the input structure, the plurality of candidate structures, or both are represented as SMILES strings.

Embodiment 64. The system of any one of Embodiments 38-63, wherein the docking geometry comprises a predicted pose of the candidate structure with respect to the input structure.

Embodiment 65. The system of any one of Embodiments 38-64, wherein the second differentiable machine learning model is a generative model.

Embodiment 66. The system of Embodiment 65, wherein the generative model is a diffusion-based or a transformer-based generative model.

Embodiment 67. The system of any one of Embodiments 38-66, wherein the second differentiable machine learning model comprises one or more models selected from the group consisting of DiffDock, GNINA, E3BIND, and TANKBind.

Embodiment 68. The system of any one of Embodiments 38-67, wherein the third differentiable machine learning model or differentiable scoring function comprises one or more models from the group consisting of ANI, Vina, Vinardo, Smina.

Embodiment 69. The system of any one of Embodiments 38-68, wherein at (b) the processor is further configured to use the first differentiable machine learning model to generate additional candidate structures, wherein the additional candidate structures are not in the plurality of candidate structures in (b).

Embodiment 70. The system of any one of Embodiments 38-69, wherein at (e) the processor is further configured to backpropagate gradient information.

Embodiment 71. The system of any one of Embodiments 38-69, wherein at (e) the processor is further configured to forward propagate gradient information.

Embodiment 72. The system of any one of Embodiments 38-71, wherein the processor is further configured to estimate an inference reliability from at least one of differentiable machine learning models.

Embodiment 73. The system of Embodiment 72, wherein the processor is further configured to determine that the inference reliability is less than a threshold, and recalculate an output of the at least one differentiable model using an underlying differentiable method on which the at least one of the differentiable machine learning models is trained or another differentiable method.

Embodiment 74. The system of Embodiment 73, wherein the processor is further configured to retrain the differentiable machine learning model based at least in part on an output from the underlying differentiable machine learning model and a gradient of the underlying differentiable machine learning model to improve the inference reliability.

Embodiment 75. A system for machine learning aided modeling of two interacting structures, the system comprising: (a) an indication of an input structure comprising an interaction region; (b) a first differentiable machine learning model configured to generate a plurality of candidate structures; (c) a second differentiable machine learning model configured to dock one or more candidate structures of the plurality of candidate structures at the interaction region of the input structure to predict a docking geometry; (d) a third differentiable machine learning model configured to rank the one or more candidate structures of the plurality of candidate structures docked by the second differentiable machine learning model to predict a score; and (e) an indication of an updated docking geometry, wherein the updated docking geometry is generated at least in part on a backpropagation of the score to (i) the first differentiable machine learning model to update the plurality of candidate structures or (ii) the second differentiable machine learning model.

Embodiment 76. A method of optimizing reference compounds, comprising: (a) obtaining a target structure and a first ligand structure; (b) generating a latent vector based on the first ligand structure; (c) processing the latent vector, with or without SE(3) equivariance or other symmetries, to generate a second ligand structure based on (i) the target structure and (ii) a score comprising a measure of affinity between the target structure and the second ligand structure, wherein the score is differentiable with respect to a definition comprising particle positions or atom types; and (d) generating a report comprising an identifier for the second ligand structure.

Embodiment 77. The method of Embodiment 76, wherein the target structure is generated using a machine learning model.

Embodiment 78. The method of Embodiment 76 or 77, wherein an interaction region of the target structure is generated using a machine learning model.

Embodiment 79. The method of any one of Embodiments 76-78, wherein the machine learning model further generates the second ligand structure.

Embodiment 80. The method of any one of Embodiments 76-79, wherein the first ligand structure is a hit compound or a lead compound.

Embodiment 81. The method of any one of Embodiments 76-80, wherein the first ligand structure is configured to interact with the target structure.

Embodiment 82. The method of any one of Embodiments 76-81, wherein the first ligand structure is configured to bind to the target structure.

Embodiment 83. The method of any one of Embodiments 76-82, wherein the second ligand structure is a lead compound or a lead-optimized compound.

Embodiment 84. The method of any one of Embodiments 76-83, wherein the second ligand structure is configured to interact with the target structure.

Embodiment 85. The method of any one of Embodiments 76-84, wherein the second ligand structure is configured to bind to the target structure.

Embodiment 86. The method of any one of Embodiments 76-85, wherein the target structure is a protein structure.

Embodiment 87. The method of any one of Embodiments 76-86, wherein the target structure comprises an interaction region.

Embodiment 88. The method of Embodiment 87, wherein the interaction region comprises a protein pocket.

Embodiment 89. The method of any one of Embodiments 76-88, wherein the first ligand structure is a small molecule, a nucleic acid, a peptide, or a protein.

Embodiment 90. The method of any one of Embodiments 76-89, wherein the latent vector is a noisy latent vector.

Embodiment 91. The method of any one of Embodiments 76-90, wherein the generating in (b) comprises noising an initial latent vector of the first ligand structure.

Embodiment 92. The method of any one of Embodiments 76-91, wherein the noising comprises diffusing the initial latent vector of the first ligand structure.

Embodiment 93. The method of any one of Embodiments 76-92, wherein the noising comprises stochastic noising.

Embodiment 94. The method of any one of Embodiments 76-93, wherein the processing in (c) comprises denoising the latent vector.

Embodiment 95. The method of Embodiment 94, wherein the denoising comprises reverse diffusing the latent vector or a noisy ligand structure thereof.

Embodiment 96. The method of any one of Embodiments 76-95, wherein the processing in (c) is performed using a neural network.

Embodiment 97. The method of Embodiment 95 or 96, wherein the neural network is a diffusion model.

Embodiment 98. The method of any one of Embodiments 95-97, wherein the target structure is fixed during the denoising.

Embodiment 99. The method of any one of Embodiments 95-98, wherein the target structure is movable during the denoising.

Embodiment 100. The method of any one of Embodiments 76-99, wherein the measure of affinity is a measure of binding affinity.

Embodiment 101. The method of any one of Embodiments 76-100, wherein the measure of affinity accounts for a potential energy of the target structure and the ligand structure.

Embodiment 102. The method of any one of Embodiments 76-101, wherein the measure of affinity accounts for a free energy of the target structure and the ligand structure.

Embodiment 103. The method of any one of Embodiments 76-102, wherein the particle positions comprise atom positions, coarse-grained particle positions, residue positions, or any combination thereof.

Embodiment 104. The method of any one of Embodiments 76-103, wherein the particle positions comprise coordinates.

Embodiment 105. The method of any one of Embodiments 76-104, wherein the measure of affinity is based on a force-field, a quantum chemical calculation, or a free energy perturbation calculation.

Embodiment 106. The method of any one of Embodiments 76-105, wherein the processing in (c) is further based on a measure of synthetic accessibility of the second ligand structure.

Embodiment 107. The method of any one of Embodiments 76-106, wherein the measure of synthetic accessibility is based on or not based on an equivariant neural network.

Embodiment 108. The method of any one of Embodiments 76-107, wherein the processing in (c) is further based on a measure of feasibility that is based on an equivariant neural network.

Embodiment 109. The method of any one of Embodiments 76-108, wherein the processing in (c) is further based on a measure of feasibility that is differentiable with respect to a definition comprising particle positions or atom types.

Embodiment 110. The method of Embodiment 108 or 109, wherein the measure of feasibility comprises measure of absorption, distribution, metabolism, and excretion-toxicity (ADMET).

Embodiment 111. The method of any one of Embodiments 76-110, further comprising synthesizing the second ligand structure.

Embodiment 112. The method of any one of Embodiments 76-111, further comprising performing a binding assay to detect a binding event between the target structure and the second ligand structure.

Embodiment 113. The method of any one of Embodiments 76-112, further comprising performing the method using the second ligand structure as the first ligand structure.

Embodiment 114. The method of any one of Embodiments 76-113, wherein the target structure is a host molecule and wherein the second ligand structure is a guest molecule.

Embodiment 115. The method of any one of Embodiments 76-114, wherein the target structure is a macromolecule or a biomolecule, and wherein the interaction region is an active site.

Embodiment 116. The method of Embodiment 115, wherein the macromolecule or the biomolecule is a protein.

Embodiment 117. The method of Embodiment 116, wherein the protein is an enzyme.

Embodiment 118. The method of any one of Embodiments 115-117, wherein the macromolecule or the biomolecule is a protein and wherein the ligand structure is selected from the group consisting of another protein, a neurotransmitter, a toxin, a neuropeptide, and a steroid.

Embodiment 119. The method of any one of Embodiments 115-118, wherein the macromolecule or the biomolecule is a protein and wherein the ligand structure is an active pharmaceutical compound.

Embodiment 120. The method of Embodiment 115, wherein the macromolecule is a metal-organic framework.

Embodiment 121. The method of Embodiment 115, wherein the macromolecule is a polymer.

Embodiment 122. The method of any one of Embodiments 76-113, wherein the target structure is a catalyst.

Embodiment 123. A method of generating lead compounds, comprising: (a) obtaining a target structure and a latent vector; (b) processing the latent vector to generate an intermediate latent vector; (c) processing the intermediate latent vector to generate a ligand structure; and (d) generating a report comprising an identifier for the ligand structure; wherein the processing in (b) and (c) are performed with or without SE(3) equivariance or other symmetries and are based on (i) the target structure and (ii) a measure of affinity between the target structure and the ligand structure, wherein the measure of binding affinity is differentiable with respect to a definition comprising particle positions or atom types.

Embodiment 124. The method of Embodiment 123, wherein the latent vector is a random latent vector.

Embodiment 125. The method of Embodiment 123 or 124, wherein the intermediate latent vector corresponds to a noisy ligand structure.

Embodiment 126. The method of any one of Embodiments 123-125, wherein the processing in (c) is performed a plurality of times to generate a plurality of ligand structures.

Embodiment 127. The method of any one of Embodiments 123-126, wherein a gradient of the measure of affinity is propagatable to the intermediate latent vector.

Embodiment 128. The method of any one of Embodiments 123-127, wherein the processing in (b) and (c) are based on a measure of synthesizability of the ligand structure.

Embodiment 129. The method of Embodiment 128, wherein a gradient of the measure of synthesizability is propagatable to the intermediate latent vector.

Embodiment 130. The method of any one of Embodiments 123-129, wherein the target structure is generated using a machine learning model.

Embodiment 131. The method of any one of Embodiments 123-130, wherein an interaction region of the target structure is generated using a machine learning model.

Embodiment 132. The method of any one of Embodiments 123-131, wherein the latent vector is generated using a machine learning model.

Embodiment 133. The method of any one of Embodiments 123-132, wherein the ligand structure is configured to interact with the target structure.

Embodiment 134. The method of any one of Embodiments 123-133, wherein the ligand structure is configured to bind to the target structure.

Embodiment 135. The method of any one of Embodiments 123-134, wherein the target structure is a protein structure.

Embodiment 136. The method of any one of Embodiments 123-135, wherein the target structure comprises an interaction region.

Embodiment 137. The method of any one of Embodiments 123-136, wherein the interaction region comprises a protein pocket.

Embodiment 138. The method of any one of Embodiments 123-137, wherein the ligand structure is a small molecule, a nucleic acid, a peptide, or a protein.

Embodiment 139. The method of any one of Embodiments 123-138, wherein the processing in (b) comprises denoising the latent vector.

Embodiment 140. The method of Embodiment 139, wherein the denoising comprises reverse diffusing the latent vector.

Embodiment 141. The method of Embodiment 139 or 140, wherein the processing in (b) is performed using a neural network.

Embodiment 142. The method of Embodiment 141, wherein the neural network is a diffusion model.

Embodiment 143. The method of any one of Embodiments 139-142, wherein the target structure is fixed during the denoising.

Embodiment 144. The method of any one of Embodiments 139-142, wherein the target structure is movable during the denoising.

Embodiment 145. The method of any one of Embodiments 123-144, wherein the measure of affinity is a measure of binding affinity.

Embodiment 146. The method of any one of Embodiments 123-145, wherein the measure of affinity accounts for a potential energy of the target structure and the ligand structure.

Embodiment 147. The method of any one of Embodiments 123-146, wherein the measure of affinity accounts for a free energy of the target structure and the ligand structure.

Embodiment 148. The method of any one of Embodiments 123-147, wherein the particle positions comprise atom positions, coarse-grained particle positions, residue positions, or any combination thereof.

Embodiment 149. The method of any one of Embodiments 123-148, wherein the particle positions comprise coordinates.

Embodiment 150. The method of any one of Embodiments 123-149, wherein the measure of affinity is based on a force-field, a quantum chemical calculation, or a free energy perturbation calculation.

Embodiment 151. The method of any one of Embodiments 123-150, wherein the processing in (b) and (c) are further based on a measure of synthetic accessibility of the ligand structure.

Embodiment 152. The method of any one of Embodiments 123-151, wherein the measure of synthetic accessibility is based on or not on an equivariant neural network.

Embodiment 153. The method of any one of Embodiments 123-152, wherein the processing in (b) is further based on a measure of feasibility that is based on an equivariant neural network.

Embodiment 154. The method of any one of Embodiments 123-153, wherein the processing in (b) is further based on a measure of feasibility that is differentiable with respect to a definition comprising particle positions or atom types.

Embodiment 155. The method of Embodiment 153 or 154, wherein the measure of feasibility comprises measure of absorption, distribution, metabolism, and excretion-toxicity (ADMET).

Embodiment 156. The method of any one of Embodiments 123-155, further comprising synthesizing the ligand structure.

Embodiment 157. The method of any one of Embodiments 123-156, further comprising performing a binding assay to detect a binding event between the target structure and the ligand structure.

Embodiment 158. The method of any one of Embodiments 123-157, further comprising performing the method using the ligand structure to generate the latent vector.

Embodiment 159. The method of any one of Embodiments 123-158, wherein the target structure is a host molecule and wherein the ligand structure is a guest molecule.

Embodiment 160. The method of any one of Embodiments 123-159, wherein the target structure is a macromolecule or a biomolecule, and wherein the interaction region is an active site.

Embodiment 161. The method of Embodiment 160, wherein the macromolecule or the biomolecule is a protein.

Embodiment 162. The method of Embodiment 161, wherein the protein is an enzyme.

Embodiment 163. The method of any one of Embodiments 160-162, wherein the macromolecule or the biomolecule is a protein and wherein the ligand structure is selected from the group consisting of another protein, a neurotransmitter, a toxin, a neuropeptide, and a steroid.

Embodiment 164. The method of any one of Embodiments 160-163, wherein the macromolecule or the biomolecule is a protein and wherein the ligand structure is an active pharmaceutical compound.

Embodiment 165. The method of Embodiment 160, wherein the macromolecule is a metal-organic framework.

Embodiment 166. The method of Embodiment 160, wherein the macromolecule is a polymer.

Embodiment 167. The method of any one of Embodiments 123-159, wherein the target structure is a catalyst.

Embodiment 168. A computer program product comprising a computer-readable medium having computer-executable code encoded therein, the computer-executable code adapted to be executed to implement any one of the method of Embodiments 76-167.

Embodiment 169. The computer program product of Embodiment 169, wherein the computer-executable code is callable through an active programming interface.

Embodiment 170. A non-transitory computer-readable storage media encoded with a computer program including instructions executable by one or more processors to implement any one of the method of Embodiments 76-167.

Embodiment 171. The non-transitory computer-readable storage media of Embodiment 169, wherein the instructions are callable through an active programming interface.

Embodiment 172. A computer-implemented system comprising: a digital processing device comprising: at least one processor, an operating system configured to perform executable instructions, a memory, and a computer program including instructions executable by the digital processing device to perform any one of the method of Embodiments 76-167.

Embodiment 173. The computer-implemented system of Embodiment 172, wherein the computer-implemented system is callable through an active programming interface.

Embodiment 174. A processor comprising a communications interface configured to connect to a computing system over a network, the processor configured to: (a) receive an indication of a problem from a user comprising a target structure and a first ligand structure; (b) direct instructions via the communications interface to generate a latent vector based on the first ligand structure, wherein the computing system is configured to process the latent vector, with or without SE(3) equivariance or other symmetries, to generate a second ligand structure based on (i) the target structure and (ii) a score comprising a measure of affinity between the target structure and the second ligand structure, wherein the score is differentiable with respect to a definition comprising particle positions or atom types; and (c) receive an output via the communications interface, the output comprising a report comprising an identifier for the second ligand structure.

Embodiment 175. A processor comprising a communications interface configured to connect to a control system over a network, the processor configured to: (a) receive instructions via the communications interface, the instructions comprising an indication of a problem comprising a target structure and a first ligand structure from a control system; (a) implement instructions to: (i) generate a latent vector based on the first ligand structure; and (ii) process the latent vector, with or without SE(3) equivariance or other symmetries, to generate a second ligand structure based on (i) the target structure and (ii) a score comprising a measure of affinity between the target structure and the second ligand structure, wherein the score is differentiable with respect to a definition comprising particle positions or atom types; and (b) direct an output to via the communications interface, the output comprising a report comprising an identifier for the second ligand structure.

Embodiment 176. A processor comprising a communications interface configured to connect to a computing system over a network, the processor configured to: (a) receive an indication of a problem from a user comprising a target structure and a latent vector; (b) direct instructions via the communications interface to process the latent vector to generate an intermediate latent vector and to process the intermediate latent vector to generate a ligand structure, wherein the computing system is configured to perform the processing, with or without SE(3) equivariance or other symmetries, based on (i) the target structure and (ii) a measure of affinity between the target structure and the ligand structure, wherein the measure of binding affinity is differentiable with respect to a definition comprising particle positions or atom types; and (c) receive an output via the communications interface, the output comprising a report comprising an identifier for the ligand structure.

Embodiment 177. A processor comprising a communications interface configured to connect to a control system over a network, the processor configured to: (a) receive instructions via the communications interface, the instructions comprising an indication of a problem comprising a target structure and a latent vector from a control system; (b) implement instructions to process the latent vector to generate an intermediate latent vector and to process the intermediate latent vector to generate a ligand structure, with or without SE(3) equivariance or other symmetries, based on (i) the target structure and (ii) a measure of affinity between the target structure and the ligand structure, wherein the measure of binding affinity is differentiable with respect to a definition comprising particle positions or atom types; and (c) direct an output to via the communications interface, the output comprising a report comprising an identifier for the ligand structure.

Embodiment 178. A method for machine learning aided modeling of a structure, the method comprising: (a) generating a plurality of candidate structures using a first differentiable machine learning model; (b) predicting one or more geometries of one or more candidate structures of the plurality of candidate structures using a second differentiable machine learning model; (c) ranking the one or more candidate structures of the plurality of candidate structures using a third differentiable machine learning model or differentiable scoring function to predict a score; and (d) propagating the score to (i) the first differentiable machine learning model to update the plurality of candidate structures or (ii) the second differentiable machine learning model to update the one or more geometries.

Embodiment 179. The method of Embodiment 178, further comprising outputting a list of the plurality of candidates updated in (d).

Embodiment 180. The method of Embodiment 178 or 179, wherein the plurality of candidate structures is provided in an environment, wherein the environment is vacuum, a gas phase media, a solvent media, or a solid surface.

Embodiment 181. The method of any one of Embodiments 178-180, wherein the plurality of candidate structures comprises a macromolecule, a biomolecule, or a ligand.

Embodiment 182. The method of Embodiment 181, wherein the macromolecule or the biomolecule is a protein.

Embodiment 183. The method of Embodiment 182, wherein the protein is an enzyme.

Embodiment 184. The method of Embodiment 181, wherein the ligand is selected from the group consisting of another protein, a neurotransmitter, a toxin, a neuropeptide, and a steroid.

Embodiment 185. The method of Embodiment 181, wherein the ligand is an active pharmaceutical compound.

Embodiment 186. The method of Embodiment 181, wherein the macromolecule is a metal-organic framework.

Embodiment 187. The method of Embodiment 181, wherein the macromolecule is a polymer.

Embodiment 188. The method of any one of Embodiments 178-187, wherein the third machine learning model is the second machine learning model, and wherein the score comprises a confidence estimate for the one or more geometries of the one or more candidate structures.

Embodiment 189. The method of Embodiment 188, wherein the confidence estimate is a prediction of the root mean squared distance between a candidate structure and a ground-truth structure.

Embodiment 190. The method of Embodiment 189, wherein the ground-truth structure is an experimentally determined structure.

Embodiment 191. The method of any one of Embodiments 178-190, wherein the second machine learning model is the first machine learning model.

Embodiment 192. The method of any one of Embodiments 178-191, wherein the score comprises an indication of a binding affinity, a volume of a molecule, or a dipole moment.

Embodiment 193. The method of any one of Embodiments 178-192, wherein (c) comprises generating a scoring function, wherein the scoring function is differentiable.

Embodiment 194. The method of any one of Embodiments 178-193, wherein (a) comprises exploring a chemical space using one or more metrics selected from the group consisting of synthesizability, uniqueness, novelty, and diversity of proposals.

Embodiment 195. The method of any one of Embodiments 178-194, wherein the first differentiable machine learning model is a generative model.

Embodiment 196. The method of Embodiment 195, wherein the generative model is a diffusion-based or a transformer-based generative model.

Embodiment 197. The method of Embodiment 196, wherein the diffusion-based generative model is a denoising diffusion probabilistic model.

Embodiment 198. The method of any one of Embodiments 178-197, wherein the first differentiable machine learning model is a deep learning model.

Embodiment 199. The method of any one of Embodiments 178-198, wherein the first differentiable machine learning model comprises one or more models selected from the group consisting of DiffSBDD, LiGAN, Deep-LigBuilder, geoLDM, and RELATION.

Embodiment 200. The method of any one of Embodiments 178-199, wherein the plurality of candidate structures are represented as SMILES structures.

Embodiment 201. The method of any one of Embodiments 178-200, wherein the second differentiable machine learning model is a generative model.

Embodiment 202. The method of Embodiment 201, wherein the generative model is a diffusion-based or a transformer-based generative model.

Embodiment 203. The method of any one of Embodiments 178-202, wherein the second differentiable machine learning model comprises one or more models selected from the group consisting of DiffDock, GNINA, E3BIND.

Embodiment 204. The method of any one of Embodiments 178-203, wherein the third differentiable machine learning model or differentiable scoring function comprises one or more models from the group consisting of ANI, Vina, Vinardo, Smina.

Embodiment 205. The method of any one of Embodiments 178-204, wherein (d) comprises using the first differentiable machine learning model to generate additional candidate structures, wherein the additional candidate structures are not in the plurality of candidate structures in (a).

Embodiment 206. The method of any one of Embodiments 178-205, wherein (d) comprises backpropagating gradient information.

Embodiment 207. The method of any one of Embodiments 178-206, wherein (d) comprises forward propagating gradient information.

Embodiment 208. The method of any one of Embodiments 178-207, further comprising estimating an inference reliability from at least one of differentiable machine learning models.

Embodiment 209. The method of Embodiment 208, further comprising determining that the inference reliability is less than a threshold, and recalculating an output of the at least one differentiable model using an underlying differentiable method on which the at least one of the differentiable machine learning models is trained or another differentiable method.

Embodiment 210. The method of Embodiment 209, further comprising retraining the differentiable machine learning model based at least in part on an output from the underlying differentiable machine learning model and a gradient of the underlying differentiable machine learning model to improve the inference reliability.

Embodiment 211. A system for machine learning aided modeling of a structure, the system comprising a non-transitory computer-readable medium with instructions stored thereon which when executed by a processor are configured to: (a) generate a plurality of candidate structures using a first differentiable machine learning model; (b) predict one or more geometries of one or more candidate structures of the plurality of candidate structures using a second differentiable machine learning model; (c) rank the one or more candidate structures of the plurality of candidate structures in (c) using a third differentiable machine learning model or a differentiable scoring function to predict a score; and (d) propagate the score to (i) the first differentiable machine learning model to update the plurality of candidate structures or (ii) the second differentiable machine learning model to update the one or more geometries.

Embodiment 212. The system of Embodiment 211, wherein the processor is further configured to output a list of the plurality of candidates updated in (d).

Embodiment 213. The system of Embodiment 211 or 212, wherein the plurality of candidate structures is provided in an environment, wherein the environment is vacuum, a gas phase media, a solvent media, or a solid surface.

Embodiment 214. The system of any one of Embodiments 211-213, wherein the plurality of candidate structures comprises a macromolecule, a biomolecule, or a ligand.

Embodiment 215. The system of Embodiment 214, wherein the macromolecule or the biomolecule is a protein.

Embodiment 216. The system of Embodiment 215, wherein the protein is an enzyme.

Embodiment 217. The system of Embodiment 214, wherein the ligand is selected from the group consisting of another protein, a neurotransmitter, a toxin, a neuropeptide, and a steroid.

Embodiment 218. The system of Embodiment 214, wherein the ligand is an active pharmaceutical compound.

Embodiment 219. The system of Embodiment 214, wherein the macromolecule is a metal-organic framework.

Embodiment 220. The system of Embodiment 214, wherein the macromolecule is a polymer.

Embodiment 221. The system of any one of Embodiments 211-220, wherein the third machine learning model is the second machine learning model, and wherein the score comprises a confidence estimate for the one or more candidate structures docked in (c).

Embodiment 222. The system of Embodiment 221, wherein the confidence estimate is a prediction of the root mean squared distance between a candidate structure and a ground truth structure.

Embodiment 223. The system of Embodiment 222, wherein the ground-truth structure is an experimentally determined structure.

Embodiment 224. The system of any one of Embodiments 211-223, wherein the second machine learning model is the first machine learning model.

Embodiment 225. The system of any one of Embodiments 211-224, wherein the score comprises an indication of a binding affinity, a volume of a molecule, or a dipole moment.

Embodiment 226. The system of any one of Embodiments 211-225, wherein at (c) the processor is further configured to generate a scoring function, wherein the scoring function is differentiable.

Embodiment 227. The system of any one of Embodiments 211-226, wherein at (a) the processor is further configured to explore a chemical space using one or more metrics selected from the group consisting of synthesizability, uniqueness, novelty, and diversity of proposals.

Embodiment 228. The system of Embodiment 227, wherein the first differentiable machine learning model is a generative model.

Embodiment 229. The system of Embodiment 228, wherein the generative model is a diffusion-based or a transformer-based generative model.

Embodiment 230. The system of Embodiment 229, wherein the diffusion-based generative model is a denoising diffusion probabilistic model.

Embodiment 231. The system of any one of Embodiments 211-230, wherein the first differentiable machine learning model is a deep learning model.

Embodiment 232. The system of any one of Embodiments 211-231, wherein the first differentiable machine learning model comprises one or more models selected from the group consisting of DiffSBDD, LiGAN, DeepLigBuilder, geoLDM, and RELATION.

Embodiment 233. The system of any one of Embodiments 211-62, wherein the plurality of candidate structures are represented as SMILES strings.

Embodiment 234. The system of any one of Embodiments 211-234, wherein the second differentiable machine learning model is a generative model.

Embodiment 235. The system of Embodiment 234, wherein the generative model is a diffusion-based or a transformer-based generative model.

Embodiment 236. The system of any one of Embodiments 211-235, wherein the second differentiable machine learning model comprises one or more models selected from the group consisting of DiffDock, GNINA, E3BIND, and TANKBind.

Embodiment 237. The system of any one of Embodiments 211-236, wherein the third differentiable machine learning model or differentiable scoring function comprises one or more models from the group consisting of ANI, Vina, Vinardo, Smina.

Embodiment 238. The system of any one of Embodiments 211-237, wherein at (d) the processor is further configured to use the first differentiable machine learning model to generate additional candidate structures, wherein the additional candidate structures are not in the plurality of candidate structures in (a).

Embodiment 239. The system of any one of Embodiments 211-238, wherein at (d) the processor is further configured to backpropagate gradient information.

Embodiment 240. The system of any one of Embodiments 211-239, wherein at (d) the processor is further configured to forward propagate gradient information.

Embodiment 241. The system of any one of Embodiments 211-240, wherein the processor is further configured to estimate an inference reliability from at least one of differentiable machine learning models.

Embodiment 242. The system of Embodiment 241, wherein the processor is further configured to determine that the inference reliability is less than a threshold, and recalculate an output of the at least one differentiable model using an underlying differentiable method on which the at least one of the differentiable machine learning models is trained or another differentiable method.

Embodiment 243. The system of Embodiment 242, wherein the processor is further configured to retrain the differentiable machine learning model based at least in part on an output from the underlying differentiable machine learning model and a gradient of the underlying differentiable machine learning model to improve the inference reliability.

Embodiment 244. A system for machine learning aided modeling of a structure, the system comprising: (a) a first differentiable machine learning model configured to generate a plurality of candidate structures; (b) a second differentiable machine learning model configured to predict one or more geometries of one or more candidate structures of the plurality of candidate structures using a second differentiable machine learning model; (c) a third differentiable machine learning model configured to rank the one or more candidate structures of the plurality of candidate structures in (c) to predict a score; and (d) an indication of an updated geometry, wherein the updated geometry is generated at least in part on a propagation of the score to (i) the first differentiable machine learning model to update the plurality of candidate structures or (ii) the second differentiable machine learning model to update the one or more geometries.

Embodiment 245. A method of optimizing reference compounds, comprising: (a) obtaining a first ligand structure; (b) generating a latent vector based on the first ligand structure; (c) processing the latent vector, with or without SE(3) equivariance or other symmetries, to generate a second ligand structure based on a score that is differentiable with respect to a definition comprising particle positions or atom types; and (d) generating a report comprising an identifier for the second ligand structure.

Embodiment 246. The method of Embodiment 245, wherein a machine learning model generates the second ligand structure.

Embodiment 247. The method of Embodiment 245 or 246, wherein the first ligand structure is a hit compound or a lead compound.

Embodiment 248. The method of any one of Embodiments 245-247, wherein the second ligand structure is a lead compound or a lead-optimized compound.

Embodiment 249. The method of any one of Embodiments 245-248, wherein the first ligand structure is a small molecule, a nucleic acid, a peptide, or a protein.

Embodiment 250. The method of any one of Embodiments 245-249, wherein the latent vector is a noisy latent vector.

Embodiment 251. The method of any one of Embodiments 245-250, wherein the generating in (b) comprises noising an initial latent vector of the first ligand structure.

Embodiment 252. The method of Embodiment 251, wherein the noising comprises diffusing the initial latent vector of the first ligand structure.

Embodiment 253. The method of Embodiment 251 or 252, wherein the noising comprises stochastic noising.

Embodiment 254. The method of any one of Embodiments 251-253, wherein the processing in (c) comprises denoising the latent vector.

Embodiment 255. The method of Embodiment 254, wherein the denoising comprises reverse diffusing the latent vector or a noisy ligand structure thereof.

Embodiment 256. The method of any one of Embodiments 245-255, wherein the processing in (c) is performed using a neural network.

Embodiment 257. The method of Embodiment 256, wherein the neural network is a diffusion model.

Embodiment 258. The method of any one of Embodiments 245-257, wherein the particle positions comprise atom positions, coarse-grained particle positions, residue positions, or any combination thereof.

Embodiment 259. The method of any one of Embodiments 245-258, wherein the particle positions comprise coordinates.

Embodiment 260. The method of any one of Embodiments 245-259, wherein the processing in (c) is further based on a measure of synthetic accessibility of the second ligand structure.

Embodiment 261. The method of any one of Embodiments 245-260, wherein the measure of synthetic accessibility is based on or not based on an equivariant neural network.

Embodiment 262. The method of any one of Embodiments 245-261, wherein the processing in (c) is further based on a measure of feasibility that is based on an equivariant neural network.

Embodiment 263. The method of any one of Embodiments 245-262, wherein the processing in (c) is further based on a measure of feasibility that is differentiable with respect to a definition comprising particle positions or atom types.

Embodiment 264. The method of Embodiment 262 or 263, wherein the measure of feasibility comprises measure of absorption, distribution, metabolism, and excretion-toxicity (ADMET).

Embodiment 265. The method of any one of Embodiments 245-264, further comprising synthesizing the second ligand structure.

Embodiment 266. The method of any one of Embodiments 245-265, further comprising performing the method using the second ligand structure as the first ligand structure.

Embodiment 267. The method of any one of Embodiments 245-266, wherein the first ligand structure is provided in an environment, and wherein the environment is vacuum, a gas phase media, a solvent media, or a solid surface.

Embodiment 268. A method of generating lead compounds, comprising: (a) obtaining a latent vector; (b) processing the latent vector to generate an intermediate latent vector; (c) processing the intermediate latent vector to generate a ligand structure; and (d) generating a report comprising an identifier for the ligand structure; wherein the processing in (b) and (c) are performed with or without SE(3) equivariance or other symmetries and are based on a score that is differentiable with respect to a definition comprising particle positions or atom types.

Embodiment 269. The method of Embodiment 268, wherein the latent vector is a random latent vector.

Embodiment 270. The method of Embodiment 268 or 269, wherein the intermediate latent vector corresponds to a noisy ligand structure.

Embodiment 271. The method of any one of Embodiments 268-270, wherein the processing in (c) is performed a plurality of times to generate a plurality of ligand structures.

Embodiment 272. The method of any one of Embodiments 268-271, wherein a gradient of the measure of affinity is propagatable to the intermediate latent vector.

Embodiment 273. The method of any one of Embodiments 268-272, wherein the processing in (b) and (c) are based on a measure of synthesizability of the ligand structure.

Embodiment 274. The method of Embodiment 273, wherein a gradient of the measure of synthesizability is propagatable to the intermediate latent vector.

Embodiment 275. The method of any one of Embodiments 268-274, wherein the latent vector is generated using a machine learning model.

Embodiment 276. The method of any one of Embodiments 268-275, wherein the ligand structure is a small molecule, a nucleic acid, a peptide, or a protein.

Embodiment 277. The method of any one of Embodiments 268-276, wherein the processing in (b) comprises denoising the latent vector.

Embodiment 278. The method of Embodiment 277, wherein the denoising comprises reverse diffusing the latent vector.

Embodiment 279. The method of Embodiment 277 or 278, wherein the processing in (b) is performed using a neural network.

Embodiment 280. The method of Embodiment 279, wherein the neural network is a diffusion model.

Embodiment 281. The method of any one of Embodiments 268-280, wherein the particle positions comprise atom positions, coarse-grained particle positions, residue positions, or any combination thereof.

Embodiment 282. The method of any one of Embodiments 268-281, wherein the particle positions comprise coordinates.

Embodiment 283. The method of any one of Embodiments 268-282, wherein the measure of affinity is based on a force-field, a quantum chemical calculation, or a free energy perturbation calculation.

Embodiment 284. The method of any one of Embodiments 268-283, wherein the processing in (b) and (c) are further based on a measure of synthetic accessibility of the ligand structure.

Embodiment 285. The method of any one of Embodiments 268-284, wherein the measure of synthetic accessibility is based on or not on an equivariant neural network.

Embodiment 286. The method of any one of Embodiments 268-285, wherein the processing in (b) is further based on a measure of feasibility that is based on an equivariant neural network.

Embodiment 287. The method of any one of Embodiments 268-286, wherein the processing in (b) is further based on a measure of feasibility that is differentiable with respect to a definition comprising particle positions or atom types.

Embodiment 288. The method of Embodiment 286 or 287, wherein the measure of feasibility comprises measure of absorption, distribution, metabolism, and excretion-toxicity (ADMET).

Embodiment 289. The method of any one of Embodiments 268-288, further comprising synthesizing the ligand structure.

Embodiment 290. The method of any one of Embodiments 268-289, further comprising performing the method using the ligand structure to generate the latent vector.

Embodiment 291. A computer program product comprising a computer-readable medium having computer-executable code encoded therein, the computer-executable code adapted to be executed to implement any one of the method of Embodiments 245-290.

Embodiment 292. The computer program product of Embodiment 291, wherein the computer-executable code is callable through an active programming interface.

Embodiment 293. A non-transitory computer-readable storage media encoded with a computer program including instructions executable by one or more processors to implement any one of the method of Embodiments 245-290.

Embodiment 294. The non-transitory computer-readable storage media of Embodiment 293, wherein the instructions are callable through an active programming interface.

Embodiment 295. A computer-implemented system comprising: a digital processing device comprising: at least one processor, an operating system configured to perform executable instructions, a memory, and a computer program including instructions executable by the digital processing device to perform any one of the method of Embodiments 245-290.

Embodiment 296. The computer-implemented system of Embodiment 295, wherein the computer-implemented system is callable through an active programming interface.

Embodiment 297. A processor comprising a communications interface configured to connect to a computing system over a network, the processor configured to: (a) receive an indication of a problem from a user comprising a first ligand structure; (b) direct instructions via the communications interface to generate a latent vector based on the first ligand structure, wherein the computing system is configured to process the latent vector, with or without SE(3) equivariance or other symmetries, to generate a second ligand structure based on a score comprising that is differentiable with respect to a definition comprising particle positions or atom types; and (c) receive an output via the communications interface, the output comprising a report comprising an identifier for the second ligand structure.

Embodiment 298. A processor comprising a communications interface configured to connect to a control system over a network, the processor configured to: (a) receive instructions via the communications interface, the instructions comprising an indication of a problem comprising a first ligand structure from a control system; (b) implement instructions to: (i) generate a latent vector based on the first ligand structure; and (ii) process the latent vector, with or without SE(3) equivariance or other symmetries, to generate a second ligand structure based on a score that is differentiable with respect to a definition comprising particle positions or atom types; and (c) direct an output to via the communications interface, the output comprising a report comprising an identifier for the second ligand structure.

Embodiment 299. A processor comprising a communications interface configured to connect to a computing system over a network, the processor configured to: (a) receive an indication of a problem from a user comprising a latent vector; (b) direct instructions via the communications interface to process the latent vector to generate an intermediate latent vector and to process the intermediate latent vector to generate a ligand structure, wherein the computing system is configured to perform the processing, with or without SE(3) equivariance or other symmetries, based on a score that is differentiable with respect to a definition comprising particle positions or atom types; and (c) receive an output via the communications interface, the output comprising a report comprising an identifier for the ligand structure.

Embodiment 300. A processor comprising a communications interface configured to connect to a control system over a network, the processor configured to: (a) receive instructions via the communications interface, the instructions comprising an indication of a problem comprising a latent vector from a control system; (b) implement instructions to process the latent vector to generate an intermediate latent vector and to process the intermediate latent vector to generate a ligand structure, with or without SE(3) equivariance or other symmetries, based on a score that is differentiable with respect to a definition comprising particle positions or atom types; and (c) direct an output to via the communications interface, the output comprising a report comprising an identifier for the ligand structure.

EXAMPLES

The following examples are provided to further illustrate some embodiments of the present disclosure but are not intended to limit the scope of the disclosure; it will be understood by their exemplary nature that other procedures, methodologies, or techniques known to those skilled in the art may alternatively be used.

Example 1: The Pipeline

This example provides a system and a method that combines a diffusion model with multi-objective optimization, where the latent variables of the diffusion model are guided to generate ligands while optimizing a plurality of target properties. Two target properties are used: binding affinity and synthetic accessibility.

To estimate binding affinity, several objectives were integrated, including a torch-based version of Vina (referred to as torchvina), DiffDock score, and the ANI2x model. To estimate synthetic accessibility (SA), an equivariant neural network model was trained to predict the SA score reported from RDKit. All metrics were written in PyTorch to be fully differentiable and connected to the latent variables within the diffusion model, allowing for the use of gradient-based optimization strategies to design optimal ligands.

The model outperforms state-of-the-art reference methods by achieving 10% and 16% higher binding scores. On a test set of experimental complexes, the model surpassed the performance of the reference ligands. The model is able to accommodate other scoring functions as well (e.g., ADME-Tox prediction), which could further improve hit-finding, hit-to-lead optimization, and lead optimization in drug discovery. The lowest Vina scores are achieved compared to previous, state-of-the-art methods. More specifically, when considering CrossDocked and Binding MOAD, an improvement of 10% (0.73 kcal/mol) and 16% (1.17 kcal/mol) to the next best tool is observed. When performing multivariate optimization with Vina and SA scores, a 7% (0.54 kcal/mol) and 15% (1.09 kcal/mol) improvement to the Vina score compared to the next best tool is observed. For Binding MOAD, the pipeline produces molecules with a lower average Vina score than reference molecules in the test set, which were derived through experiment. The pipeline also performs lead optimization by starting with a reference molecule. The lead optimization finds other ligands with lower Vina scores 100% of the time, while also lowering the SA score for ~95% of cases.

The model is implemented as a cloud-based simulation package that includes several methods to compute different properties of molecules and materials. The model takes the protein pocket information as input and iteratively modifies the predictions of a generator that generates molecules directly into the pocket to produce optimal ligands, according to a set of differentiable scores defining target properties. The model accomplishes this task by modifying the latent vectors of the generative model. Once a set of optimal ligands are produced, ligand binding poses are further refined by performing structural optimization within the pocket. The structural optimization algorithm interfaces with the same differentiable scores used for latent optimization and iteratively modifies the ligands' coordinates.

The ability of the model to discover novel ligands with improved binding affinity and synthetic accessibility is evaluated. A torch-based implementation of the Vina score was developed (referred to as torchvina herein). To evaluate synthetic accessibility, an equivariant neural network model is trained to predict the synthetic accessibility (SA) score (referred to as torchSA).

The performance of the pipeline is evaluated with two separate tests sets: (1) a subset of CrossDocked, and (2) a subset of the Binding MOAD (Mother of all Databases). Both databases contain protein pocket-ligand pairs. The protein-ligand pairs in CrossDocked are derived via re-docking ligands to non-cognate receptors with smina. The Binding MOAD contains high resolution (<2.5 Å) protein-ligand pairs derived through experiment.

For each protein pocket in each test set, 100 optimized ligands were generated using the model. The ability of the model to discover novel ligands with improved binding affinity and synthetic accessibility is assessed. In particular, univariate optimization is performed with torchvina and multivariate optimization using torchvina and torchSA scores.

Validation of Latent Vector Optimization

To assess the ability of the model to augment the performance of the baseline model via the optimization of latent vectors, the model is run to optimize torchvina, and the summation of torchvina and torchSA, to analyze its capability to improve Vina and SA scores relative to DiffSBDD-Cond. For each of the protein pockets in the CrossDocked test set, the Vina and SA scores of the ligand are calculated before and after latent vector optimization with the model. The average Vina and SA scores, and the top-10% Vina and SA scores for each method are reported in Table 1. The average Vina score of synthesizable ligands across all pockets are also reported A ligand was considered to be synthesizable if it achieves an SA score of less than 3.5. The results are shown in Table 2.

TABLE 1

Performance of the model when used to optimize torchvina, and the combination of torchvina and torchSA relative to the baseline model, DiffSBDD-cond. For the average Vina score of synthesizable molecules, the number of targets that are included in the calculation are indicated. DiffSBDD-Cond is used as a reference method for predicting ligands within a protein pocket. DiffSBDD-Cond is able to consistently generate ligands within the protein pocket without clashes.

| Method | Vina (kcal/mol) | Vina$_{10\%}$ (kcal/mol) | Vina$_{synth}$ (kcal/mol) | SA | SA$_{10\%}$ |
|---|---|---|---|---|---|
| DiffSBDD-cond | −4.56 | −7.62 | −4.50 (94/100) | 4.96 | 3.26 |

TABLE 1-continued

Performance of the model when used to optimize torchvina,
and the combination of torchvina and torchSA relative to
the baseline model, DiffSBDD-cond. For the average Vina score
of synthesizable molecules, the number of targets that are
included in the calculation are indicated. DiffSBDD-Cond
is used as a reference method for predicting ligands within
a protein pocket. DiffSBDD-Cond is able to consistently generate
ligands within the protein pocket without clashes.

| Method | Vina (kcal/mol) | Vina$_{10\%}$ (kcal/mol) | Vina$_{synth}$ (kcal/mol) | SA | SA$_{10\%}$ |
|---|---|---|---|---|---|
| Model (Vina) | −7.26 | −10.13 | −5.79 (76/100) | 5.75 | 4.01 |
| Model (Vina + SA) | −7.08 | −9.85 | −6.15 (89/100) | 5.09 | 3.29 |

TABLE 2

Results of ML tools compared on targets from the CrossDocked and Binding MOAD
datasets. The average, along with the standard deviation across the protein
pockets in each dataset are reported for each metric. The top performing
model is bolded in each column. Time is based on running DiffSBDD-cond.

| Dataset | Method | Vina (kcal/mol) | Vina$_{10\%}$ (kcal/mol) | SA |
|---|---|---|---|---|
| CrossDocked | Test Set | −6.87 +/− 2.32 | — | 3.45 +/− 1.26 |
| | 3D-SBDD | −5.89 +/− 1.91 | −7.29 +/− 2.34 | 3.93 +/− 1.26 |
| | Pocket2Mol | −7.06 +/− 2.80 | −8.71 +/− 3.18 | 3.23 +/− 1.08 |
| | GraphBP | −4.72 +/− 4.03 | −7.17 +/− 1.40 | 7.24 +/− 0.81 |
| | TargetDiff | −7.32 +/− 2.47 | −9.67 +/− 2.55 | 4.74 +/− 1.17 |
| | DiffSBDD-cond | −6.95 +/− 2.06 | −9.12 +/− 2.16 | 4.80 +/− 1.17 |
| | DiffSBDD-inpaint | −7.33 +/− 2.56 | −9.93 +/− 2.59 | 5.01 +/− 1.08 |
| | Pipeline (vina) | −8.06 +/− 2.18 | −10.87 +/− 2.76 | 5.75 +/− 0.35 |
| | Pipeline (vina + SA) | −7.87 +/− 2.22 | −10.57 +/− 2.75 | 5.09 +/− 0.53 |
| MOAD | Test Set | −8.41 +/− 2.03 | — | 3.77 +/− 1.08 |
| | GraphBP | −4.84 +/− 2.24 | −6.63 +/− 0.95 | 7.21 +/− 0.81 |
| | DiffSBDD-cond | −7.17 +/− 1.89 | −9.18 +/− 2.23 | 4.89 +/− 1.08 |
| | DiffSBDD-inpaint | −7.31 +/− 4.03 | −9.84 +/− 2.18 | 4.47 +/− 1.08 |
| | Pipeline (vina) | −8.48 +/− 2.54 | −11.30 +/− 3.02 | 5.86 +/− 0.47 |
| | Pipeline (vina + SA) | −8.40 +/− 2.29 | −11.16 +/− 2.96 | 5.31 +/− 0.59 |

| Dataset | Method | QED | Diversity | Time (s/ligand) |
|---|---|---|---|---|
| CrossDocked | Test Set | 0.48 +/− 0.20 | — | — |
| | 3D-SBDD | 0.50 +/− 0.17 | 0.74 +/− 0.09 | 328.13 +/− 245.43 |
| | Pocket2Mol | 0.57 +/− 0.16 | 0.74 +/− 0.15 | 41.79 +/− 36.84 |
| | GraphBP | 0.50 +/− 0.12 | 0.84 +/− 0.01 | 0.17 +/− 0.02 |
| | TargetDiff | 0.48 +/− 0.20 | 0.72 +/− 0.09 | ~57.22 |
| | DiffSBDD-cond | 0.47 +/− 0.21 | 0.73 +/− 0.07 | 2.27 +/− 0.86 |
| | DiffSBDD-inpaint | 0.47 +/− 0.18 | 0.76 +/− 0.05 | 2.67 +/− 1.22 |
| | Pipeline (vina) | 0.39 +/− 0.08 | 0.65 +/− 0.08 | 34.26 +/− 16.69 |
| | Pipeline (vina + SA) | 0.39 +/− 0.09 | 0.67 +/− 0.09 | 43.74 +/− 15.97 |
| MOAD | Test Set | 0.52 +/− 0.17 | — | — |
| | GraphBP | 0.51 +/− 0.11 | 0.83 +/− 0.01 | 0.23 +/− 0.03 |
| | DiffSBDD-cond | 0.44 +/− 0.20 | 0.71 +/− 0.08 | 5.61 +/− 1.42 |
| | DiffSBDD-inpaint | 0.54 +/− 0.21 | 0.74 +/− 0.05 | 6.17 +/− 2.08 |
| | Pipeline (vina) | 0.32 +/− 0.04 | 0.62 +/− 0.13 | 69.89 +/− 64.78 |
| | Pipeline (vina + SA) | 0.32 +/− 0.07 | 0.64 +/− 0.12 | 85.57 +/− 61.70 |

The model generates ligands with significantly better Vina scores than DiffSBDD-cond, yielding molecules with ~59% lower Vina score when performing univariate optimization, and ~55% improvement when optimizing the combined torchvina and torchSA score. The model also generates ligands with a drastically improved top-10% Vina score relative to DiffSBDD-cond, yielding molecules with ~33% and 29% lower top-10% Vina score when used with torchvina and torchvina+torchSA respectively.

Although using torchvina yielded molecules with improved binding affinity, the improvement had showed a tradeoff against synthetic accessibility. The average SA score and top-10% SA score of molecules generated by Pipeline with torchvina are 5.75 and 4.01 respectively, compared to 4.96 and 3.26 for DiffSBDD-Cond. Multivariate optimization with the objective torchvina+torchSA elicits molecules with better synthetic accessibility, 5.09 for average SA score, and 3.29 top-10% SA score. The binding affinity of synthesizable ligands improves relative to both DiffSBDD-cond and when optimizing torchvina alone.

The model, including latent vector optimization and structural refinement, is compared to other tools tested against the CrossDocked and Binding MOAD test sets. Additional metrics are considered, including QED (quantitative estimate of drug-likeness; a metric combining severable desirable molecular properties for screening drug-like molecules), diversity (a measure of the average pairwise dissimilarity between all generated molecules for a given protein pocket), and generation speed (measure of the average time taken to generate a single ligand with each framework). Dissimilarity is measured as 1−Tanimoto similarity.

The model is run to completion from start to finish, first optimizing latent vectors, followed by structural refinement. For CrossDocked, the model achieves significantly improved average and top-10% Vina scores over other tools, with a 0.69 kcal/mol improvement and 0.94 kcal/mol improvement respectively compared to the next best tool, DiffSBDD-inpaint when used with just torchvina. When the model is run with both torchvina and torchSA, the SA score of generated ligands improves, achieving similar average SA to DiffSBDD-inpaint. The model remains computationally tractable, achieving run times competitive with two other tools, TargetDiff and Pocket2Mol, and is even faster than 3D-SBDD. The full results are shown in Table 2.

The model with torchvina finds ligands that have better binding affinity than the reference ligand for 99/100 targets, while the model with torchvina+torchSA does for 98/100 targets. The model demonstrates its ability to find ligands that improve upon both the Vina score and SA score compared to the reference ligand when run with both torchvina and torchSA, finding such a ligand for 71/100 targets in the CrossDocked test set.

For the Binding MOAD dataset, the advantage of the model for generating molecules with high binding affinity is even more pronounced, with a 1.17 kcal/mol improvement in average Vina score, and 1.46 kcal/mol improvement in top-10% Vina score compared to the next best method, DiffSBDD-inpaint, when used with just torchvina. In particular, the model with torchvina is the first model to surpass the average Vina score of reference molecules in the Binding MOAD. This is noteworthy, especially because molecules in the Binding MOAD were derived through experiment. When used with both torchvina and torchSA, the model achieved slightly lower average Vina and top-10% Vina scores, while improving the SA. The time to generate a single ligand for a protein pocket in the Binding MOAD test set is approximately twice as slow as for the CrossDocked dataset, reflecting DiffSBDD's slowdown in proposing novel molecules for targets in this set. The model with torchvina finds a molecule with a lower Vina score than the reference for 128/130 cases, while torchvina+torchSA did so for 125/130 cases. The torchvina+torchSA model finds a molecule with a better Vina score and SA score for 123/130 targets. The SA scores in the Binding MOAD dataset are larger than the ones from CrossDocked.

Overall, the model generates ligands with state-of-the-art binding affinity, and good synthetic accessibility. Improving metrics with the model is straightforward, which can be done by coupling a differentiable score for evaluating the desired metric. Desired metrics can be, e.g., solubility or toxicity.

Improving Reference Molecules

In addition to de novo generation, the system and the method can also be used to optimize a known ligand in the protein pocket. This functionality is useful for lead optimization, where a molecule is progressed from an initial promising candidate towards one having optimal properties.

To accomplish the task of reference optimization, the generation task is seeded with a latent vector derived from the input ligand. The given ligand is noised for $t_{hz}$ timesteps, creating latent vector $z^{thz}$. From this point, the optimization proceeds as it does when generating molecules from scratch.

To test this capability of this framework, the protein-pockets from the CrossDocked test set is used to generate the same number of molecules as when generating ligands from scratch. The torchvina+torchSA model is used to optimize reference molecules from the dataset. The results are compared against molecule generation from scratch. The results are reported in Table 3.

TABLE 3

Comparison between optimizing ligands from scratch versus optimizing ligands when starting with a reference ligand. The final column (Improved) is the percentage of ligands where the final Vina and SA scores are less than the reference.

| Method | Vina (kcal/mol) | Vina$_{10\%}$ (kcal/mol) | SA | SA$_{10\%}$ | Improved (%) |
|---|---|---|---|---|---|
| Test Set | −5.49 | — | 3.45 | — | — |
| Model (Vina + SA) (scratch) | −7.06 | −9.82 | 5.08 | 3.28 | 72 |
| Model (Vina + SA) (reference) | −6.58 | −7.60 | 4.05 | 3.04 | 95 |

The average Vina scores of the optimized ligands are significantly better than the seed molecules (1.12 kcal/mol). Starting from scratch results in a slightly better average Vina score (0.42 kcal/mol), and a significantly better top-10% Vina score (2.23 kcal/mol) than seeding with the references from the test set. However, when comparing the performance of the model for finding molecules that have both a better binding affinity and SA score than the reference, starting from a given molecule has a significant advantage-such a target was found ~95% of the time, compared to only ~72% of the time when starting from scratch. Furthermore, the top-10% SA score is better than the average SA found in the reference molecules. Starting from a reference molecule can be used to fine-tune a given ligand producing other ligands with better binding affinity and synthesizability scores. Meanwhile, generating the molecule from scratch is better for achieving a lower binding affinity score.

Generator Model

The following describes the generation methodology in further detail. A denoising diffusion probabilistic model (DDPM) generates samples from a target distribution by learning the reverse of a noising process. Gaussian random noise is iteratively injected into samples from the target distribution until no information from the original sample remains. The model reverses this process during generation, transforming random noise into samples from the target distribution. The diffusion model generates samples by denoising a random initial latent vector for T steps. The initial latent vector is drawn from a normal distribution, $z_T \sim \mathcal{N}(0, I)$.

The model generates consecutive latent vectors by predicting the noise at time t, $\epsilon_\theta(z_t, t)$, where $\theta$ are the model weights. The noise is removed from $z_t$ in order to generate $z_{t-1}$. $z_0$ is the final prediction of the model.

This example employs DiffSBDD, an SE(3)-equivariant 3D-conditional DDPM which respects translation, rotation, and permutation symmetries. DiffSBDD was trained to predict ligands with high binding affinity given a target protein pocket. In DiffSBDD, data samples comprise protein pocket and ligand point clouds (atomic numbers and coordinates), i.e., $z=[r,h]$ where $r \in R^{N \times 3}$ is a tensor of atomic coordinates, and $h \in R^{N \times 10}$ is a tensor of atomic probabilities over the atom types which the model can generate. Within the model, each $z_t$ is converted to a graph and processed by an EGNN to produce a prediction of $\epsilon_\theta(z_t, t)$. DiffSBDD contains two different models for 3D pocket conditioning—a conditional DDPM that receives a fixed pocket representation as the context in each denoising step, and a model that is trained to approximate the joint distribution of ligand-protein pocket pairs and is combined with a modified sampling procedure, inpainting, at inference time. The generation can be performed with a constraint that the generated ligands do not overlap with the target protein pocket. The ligands can be later docked using structural optimization.

DiffSBDD was trained on a subset of the CrossDocked, and the Binding MOAD datasets. For training, train/test splits comprised 100,000 complexes for training, and 100 protein pockets for testing.

DiffSBDD showed state-of-the-art performance on both test sets. In particular, DiffSBDD achieved the best average, and best top-10% Vina score when compared with other state-of-the-art models in the literature—3D-SBDD, Pocket2Mol, GraphBP, and TargetDiff.

Although DiffSBDD is used in this example, any other generative model, including those which makes use of latent vectors as intermediate representations during generation, can be used.

Ligand Validity Checks

Chemical and structural checks are used to ensure that the generated ligand is valid. A number of these checks are performed using RDKit. These include verifying that hydrogens can be added to the ligand and assigned a Cartesian coordinate, that the ligand is not fragmented, and that the ligand can be sanitized. All of these except for the valency check can also be performed within DiffSBDD.

Other checks are employed to ensure the structural validity of the ligand. Various checks can allow subsequent docking calculations to proceed using other models or frameworks. The checks were performed to make sure that the ligand contains only atoms compatible with ANI2x. DiffSBDD can generate ligands with four atom types that are incompatible with ANI2x, e.g., B, P, Br, and I. The checks were performed to make sure that the bond lengths in the ligand are correct by referring to covalent radii, and that the ligand does not overlap with the protein pocket. This is done via ASE's (Atomic Simulation Environment) NeighborList class. The checks were performed to make sure that the atoms do not have significant overlap within the ligand itself. This is done via pymatgen's Molecule class.

Scoring Functions

Generated ligands are scored using a scoring function. The scoring functions include a custom torch-based Vina score (torchvina), an ensemble of neural networks trained to predict the synthetic accessibility (torchSA), the scoring function from DiffDock, and the ANI2x model. These objectives are written in Pytorch with differentiable operations and hence can be differentiated automatically using autograd.

Torchvina

The Vina force field was implemented using Pytorch to allow for automatic differentiation with respect to the latent parameters of the generator. The Vina force field is composed of a weighted sum of atomic interactions. Steric, hydrophobic, and hydrogen bonding interactions are calculated and weighted according to a nonlinear fit to structural data. The final score is re-weighted by the number of rotatable bonds to account for entropic penalties. The Vina score is composed of a sum of intramolecular and intermolecular terms. Only the intermolecular interaction term between the ligand and protein pocket is implemented for the measure of binding affinity.

Docking with Vina can outperform state-of-the-art ML models such as DiffDock when stricter chemical and physical validity checks were enforced on docked molecules, or when these procedures were evaluated on a dataset composed of examples distinct from the ML models' training data.

To have an evaluator model capable of estimating synthesizability, an ensemble of neural networks was trained to predict the synthetic accessibility (SA) score. SA score used ranges from 1 (easy to make) to 10 (very difficult to make) and is effective for biasing generative pipelines towards synthesizable molecules. It is used with DiffSBDD to measure the performance of the pipeline.

To allow the SA score to be differentiable, a machine learning model is constructed to receive atomic point clouds, $z=[r,h]$, where $r \in R^{N \times 3}$ is a tensor of atomic coordinates of atoms in the ligand, and $h \in R^{N \times 10}$ is a tensor of probability distributions over the possible atom types. The machine learning model is trained on a constructed dataset of atomic point clouds of ligands labeled with SA score. To allow for predictions on probability distributions of atom types, atom types are encoded as one-hot vectors.

ANI2x

ANI2x is a neural network ensemble model that is part of the ANI suite of models. The ANI models are trained on quantum chemistry calculations (at the density functional theory level) to predict the total energy of a target structure. The ANI models are trained on millions of organic molecules and are accurate across different domains. In addition, they have been shown to outperform many common force fields in terms of accuracy. The ANI models make use of atomic environment descriptors, which probe their local environment, as input vectors. An individual ANI model contains multiple neural networks, each specialized for a specific atom type, predicting the energy contributed by atoms of that type in the molecular structures. The total energy of the structures is obtained by performing a summation over the atomic contributions. The ANI2x model is an ensemble model consisting of 8 individual ANI models. Each sub-model is trained on a different fold of the ANI2x dataset, composed of gas-phase molecules containing seven different atom types—H, C, N, O, F, CI, and S. These seven atom types cover ≈90% of drug-like molecules.

Latent Vector Optimization

Latent vectors are modified and used by the generator to generate novel ligands. This is performed by repeatedly evaluating generated ligands with an objective composed of a set of differentiable scores, calculating the gradient of the objective with respect to the latent vectors (facilitated by automatic differentiation with Pytorch), and modifying the latent vectors via a gradient-based optimizer.

When optimizing latent vectors in DiffSBDD, the initial latent vectors used by the model are not modified. Instead, an optimization horizon, $t_{hz}$, is defined. First latent vectors are generated up to the optimization horizon $z_T, \ldots, z_0$. This latent vector is saved, and the remaining latent vectors, $z_{t_{h}-1}, \ldots, z_0$, are generated. The gradient of the objective with respect to $z_{t_h}$ is evaluated, and $z_{t_h}$ is modified using the Adam optimizer. When re-generating ligands, rather than starting from $z_T$, only latent vectors proceeding the optimization horizon are generated, i.e., $z_{t_{h}-1}, \ldots, z_0$.

This example focuses on two combinations of evaluators: torchvina on its own, and torchvina in combination with torchSA. The Adam optimizer is used with $\beta_1=0.5$ and $\beta_2=0.999$ to modify latent vectors. Hyperparameter optimization is performed to choose both the learning rate of Adam, and the optimization horizon.

Structural Refinement

Structural refinement is used to optimize a generated ligand's coordinates. The scoring module is used to repeatedly evaluate ligands, and the derivatives concerning the ligand's coordinates are used to modify the ligand's coordinates with a gradient-based optimizer. The L-BFGS optimizer in Pytorch is used to perform coordinate optimization. The optimization algorithm is implemented with Pytorch and is parallelizable on a GPU. In this example, only one combination of evaluators is used to perform coordinate optimization: torchvina and ANI2x.

TABLE 4

Validation set used to choose hyper-parameters in the pipeline. All proteins from the test set of LiGAN are used, and a single protein pocket for each protein is selected at random.

| PDB ID | Ligand ID |
|--------|-----------|
| 2ah9 | cto |
| 5lvq | p2l |
| 5g3n | u8d |
| 1u0f | g6p |
| 4bnw | fxe |
| 4i91 | cpz |
| 2ati | ihu |
| 2hw1 | lj9 |
| 1bvr | geq |
| 1zyu | k2q |

Hyperparameter Tuning

Several hyperparameter tuning experiments are performed to fine-tune the performance of the pipeline. To deter the pipeline from overfitting on the test set, all experiments are performed using a non-overlapping validation set. This validation set is composed of 10 targets taken from the test set of LiGAN, which is also used to validate the performance of several other works in the literature. For each of these ten targets, a single pocket is randomly selected to be included in the validation set. Each hyperparameter experiment is run for 200 optimization steps with a batch size of 25 on an NVIDIA A10G GPU with 24 GB of GPU memory.

Optimizing Latent Vectors with Torchvina

The performance of the model is tuned to optimize the Vina score of generated ligands. Hyperparameter tuning is performed to determine the optimization horizon, hz, and the learning rate of the optimizer, lr. For hz, values in the set $\{2, 10, 20, 50, 100, 200\}$ are considered, and for lr values in the set $\{0.001, 0.01, 0.1\}$ are considered. For each experiment, the average Vina score, the following are recorded: average Vina score of the top 10% of structures, the Tanimoto similarity between the initial ligand in the trajectory, and the best ligand in the trajectory, the pocket diversity, and the time taken to optimize a single ligand. The combination of hz=50, and hz=0.1 yields the best results in terms of average Vina score and top 10% Vina score with values of, respectively, −7.38, and −10.70. Setting the lr=0.1 yields the best results. A violin plot of the distribution of average Vina scores across the 10 targets when using lr=0.1 with different optimization horizons is provided in FIG. 11.

TABLE 5

Results of hyperparameter tuning when optimizing torchvina. lr = 0.1 and hz = 50 results in both the best average Vina score and best top 10% Vina score.

| Vina | | horizon | | | | | |
|------|------|------|------|------|------|------|------|
| | | 2 | 10 | 20 | 50 | 100 | 200 |
| lr | 0.001 | −5.67 | −5.02 | −6.28 | −5.77 | −5.5 | −6.52 |
| | 0.01 | −6.26 | −6.65 | −6.81 | −6.17 | −6.13 | −6.74 |
| | 0.1 | −6.13 | −6.91 | −6.85 | −7.38 | −7.16 | −6.96 |

| $Vina_{10\%}$ | | horizon | | | | | |
|------|------|------|------|------|------|------|------|
| | | 2 | 10 | 20 | 50 | 100 | 200 |
| lr | 0.001 | −9.26 | −9.36 | −9.67 | −9.41 | −9.92 | −10.19 |
| | 0.01 | −9.68 | −10.46 | −10.5 | −9.68 | −9.99 | −10.23 |
| | 0.1 | −9.35 | −10.46 | −10.65 | −10.7 | −10.59 | −10.39 |

| Tanimoto | | horizon | | | | | |
|------|------|------|------|------|------|------|------|
| | | 2 | 10 | 20 | 50 | 100 | 200 |
| lr | 0.001 | 0.77 | 0.74 | 0.69 | 0.49 | 0.43 | 0.4 |
| | 0.01 | 0.68 | 0.61 | 0.57 | 0.47 | 0.41 | 0.41 |
| | 0.1 | 0.69 | 0.53 | 0.49 | 0.42 | 0.41 | 0.4 |

| Time | | horizon | | | | | |
|------|------|------|------|------|------|------|------|
| (ligand/s) | | 2 | 10 | 20 | 50 | 100 | 200 |
| lr | 0.001 | 57.32 | 137.03 | 202.85 | 317.32 | 319.31 | 439.85 |
| | 0.01 | 32.26 | 81.09 | 136.69 | 282.47 | 356.74 | 395.51 |
| | 0.1 | 33.32 | 40.69 | 79.49 | 160.94 | 248.97 | 373.9 |

| Diversity | | horizon | | | | | |
|------|------|------|------|------|------|------|------|
| | | 2 | 10 | 20 | 50 | 100 | 200 |
| lr | 0.001 | 0.66 | 0.65 | 0.65 | 0.64 | 0.63 | 0.62 |
| | 0.01 | 0.67 | 0.66 | 0.65 | 0.63 | 0.63 | 0.61 |
| | 0.1 | 0.67 | 0.65 | 0.63 | 0.62 | 0.61 | 0.61 |

The performance of the model is tuned to optimize the SA score of generated ligands. Hyperparameter tuning is performed for the learning rate of the Adam optimizer. Values in the set {0.001, 0.005, 0.01, 0.05, 0.1} are considered. For each experiment, the following metrics are computed: the average SA score, the average SA score of the top 10% of ligands, and the percent of synthesizable ligands produced when using a hyperparameter setting. A threshold value of synthesizability, for this example, is SA score lower than 3.5. The best results are yielded with lr=0.05: highest overall SA score, highest top 10% SA score, and highest percent of synthesizable ligands. When running the pipeline with both torchvina and torchSA as the objective, we use lr=0.1 is used with a weight of 0.5 on torchSA in the loss to achieve the optimal learning rate for each objective.

TABLE 6

Results of hyperparameter tuning for latent vector optimization with torchSA. Each run has its average SA score, top 10% SA score, and percent of synthesizable ligands generated recorded. Setting lr = 0.05 gives the best results for all three metrics.

| lr | 0.001 | 0.005 | 0.01 | 0.05 | 0.1 |
|---|---|---|---|---|---|
| SA | 5 | 4.93 | 4.73 | 4.64 | 4.69 |
| SA10% | 3.69 | 3.37 | 3.12 | 3.04 | 3.14 |
| Synth | 5.50% | 7.70% | 12.40% | 13.10% | 11.70% |

Docking with TorchVina and ANI2x

The learning rate of the optimizer and the weighting scheme for the docking calculations were tuned by balancing torchvina with ANI2x energy. The following parameters are used in the L-BFGS optimization algorithm: max-iter100, tolerance-change=0, tolerance-grad=10-2, and line-search-fn=strong-wolfe. For learning rate, values in {0.01, 0.02, 0.03, 0.04, 0.05, 0.25} were considered. For weight on ANI energy, values in {0.1, 1, 10, 100, 627.5} were considered. For each experiment, the average Vina score, the top % 10 Vina score, the average time taken to optimize each ligand, and the percent of valid structures that are output by the procedure based on the validity checks are checked. The same metrics are taken when Quick Vina is used for docking for comparison. Quick Vina is used to dock structures after generation in DiffSBDD. Setting the weight on ANI energy to 0.1 gives the best balance of high binding affinity with high validity. For lr, there is a trade-off between high binding affinity and validity. For lr between 0.01 and 0.05, a slight drop-off in the percent of valid structures yielded can be traded off for higher binding affinity. For lr>0.05, the validity is reduced. Thus, lr of 0.05 is used for the pipeline. With this lr a higher average Vina score is achieved than Quick Vina (−9.45 vs −8.70) and a higher top 10% Vina score (−12.37 vs. −11.15), at the cost of lowered validity (89.2% vs 98.3%). Furthermore, since the algorithm makes use of Pytorch's L-BFGS minimizer, it is highly parallelizable and can dock ~100 ligands in just over 2 minutes on an NVIDIA A10G GPU with 8 CPU cores. Although these results are not directly comparable with Quick Vina, as the L-BFGS algorithm takes advantage of the GPU's computing resources and Quick Vina relies entirely on the CPU cores, the results nevertheless provide an accurate estimate of efficiency when integrating these docking procedures into the pipeline running on a GPU.

TABLE 7

Results when docking ligands generated for pockets in the validation set with QuickVina and with the pipeline when used with several learning rates.

| Description | Vina (kcal/mol) | Vina$_{10\%}$ (kcal/mol) | Validity (%) | Time (s/ligand) |
|---|---|---|---|---|
| Quick Vina | −8.7 | −11.15 | 98.3 | 13.30 |
| IDOLpro$_{dock}$(lr = 0.01) | −7.89 | −11.18 | 98.9 | 2.25 |
| IDOLpro$_{dock}$(lr = 0.02) | −8.59 | −11.67 | 97 | 2.25 |
| IDOLpro$_{dock}$(lr = 0.03) | −8.82 | −11.83 | 96 | 2.23 |
| IDOLpro$_{dock}$(lr = 0.04) | −9.27 | −12.21 | 92.2 | 2.25 |
| IDOLpro$_{dock}$(lr = 0.05) | −9.45 | −12.37 | 89.2 | 2.25 |
| IDOLpro$_{dock}$(lr = 0.10) | −9.78 | −12.44 | 72.4 | 2.28 |
| IDOLpro$_{dock}$(lr = 0.25) | −9.82 | −12.17 | 60.8 | 2.06 |

Accelerating Diffusion

Although in DiffSBDD the models are trained to generate ligands over 500 diffusion steps, there is the option to reduce the overall number of steps at the cost of accuracy in predictions. To test whether the run-time of the pipeline can be accelerated, the pipeline is run with 100 diffusion steps and a horizon of 10. A slightly lower overall Vina score (−7.52 vs −7.38) resulted, albeit a slightly higher $\langle$Vina$\rangle_{top10\%}$ when running with less generative diffusion steps (−10.56 vs −10.70). Running the pipeline in this setting results in a 4× speedup when generating ligands. Due to the lack of degradation in Vina score when using fewer diffusion steps, this setting is adopted for the pipeline.

Stopping Criteria, Backtracking, and Decaying Learning Rate

Per-parameter options are used in Pytorch to allow for individualized learning rates for different ligands. For each ligand, the pipeline is optimized with Adam with the chosen hyperparameters. Each latent vector is optimized for 10-200 optimization steps. During latent vector optimization, a ligand sometimes is pushed to a part of latent space such that it becomes an invalid result. In such a case, a ligand is generated 10 times with the given latent vector. If after 10 attempts, reverse diffusion has not produced a valid ligand, the optimization is restarted from the previous latent vector in the optimization trajectory with a reduced learning rate by a factor of 10. If at another point in the optimization, with the reduced learning rate, another latent vector fails to generate a valid ligand over 10 attempts, the optimization of that trajectory is stopped.

An Additional Scoring Function: DiffDock

The scoring module from DiffDock is used with the evaluator. DiffDock is composed of two modules, a docking module and a scoring module, which together can dock ligands to a target protein without pocket information. The DiffDock docking module is trained to predict the experimental binding pose of ligands in the PDBBind dataset. The DiffDock scoring module is trained on experimental data where the goal of the model is to classify whether or not a candidate ligand is <2 AA~ of the experimental binding pose. DiffDock docks ligands by producing many binding poses for a target ligand with the docking module and returning these poses as a ranked list using the scoring module. The node from the final classification layer of the scoring network, indicating the likelihood that a docked ligand is <2 AA~ from an experimentally derived binding pose, can be used as a scoring function. A visualization of the latent vectors is shown in FIG. 14.

More Details on the TorchSA Model

The dataset comprises 183,468 ligand binding poses. Although the SA score is fully determined by the chemical graph of a ligand and does not depend on its conformation, multiple poses of the same ligand are ligand so that the model learns the redundancy of pose in determining the SA score. To have a good performance on ligands produced by DiffSBDD, 98,398 ligands are generated with DiffSBDD which are included in the training set. Several ligands are generated for each of the protein pockets in the DiffSBDD training set and then filtered using the validity checks.

The polarizable atomic interaction neural network (PaiNN) from Open Catalyst Project is trained to predict the SA score given the atomic coordinates and atom types. The hyperparameters of the model is optimized using Ray Tune. The hyperparameters chosen are num-rbf=64, num-layers=4, max-neighbor=30, cutoff=8.0, hidden-channels=512. Each training set is split into 5 folds, and 5 neural networks are each trained on 4/5 folds such that overall the model sees every data point in each dataset. The remaining folds are used as validation sets for each model. Each model is trained for 100 epochs to minimize the MSE loss with the AdamW optimizer with an initial learning rate of $1 \times 10^{-4}$. The learning rate is halved if the training loss does not decrease for 10 consecutive epochs. Training and validation curves are plotted in FIG. 10. From the validation curves produced for each dataset, it can be seen that the model achieves significantly better results predicting SA score on ligands extracted from CrossDocked than on ligands generated by DiffSBDD.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

The invention claimed is:

1. A method performed by one or more computers, the method comprising:

identifying one or more ligands for binding to a target molecule by performing operations comprising:

obtaining data identifying an input ligand;

generating, using a generative machine learning model, a noised latent vector by combining random noise with data representing the input ligand, wherein the generative machine learning model has been trained, by a machine learning training technique on a training dataset of ligand structures, to generate a predicted structure of a ligand by denoising an initial latent vector over a sequence of denoising iterations;

iteratively denoising the noised latent vector using the generative machine learning model over the sequence of denoising iterations to generate a final denoised latent vector that defines an output ligand;

processing a model input characterizing a 3D structure of the output ligand using a scoring model to generate a quality score for the output ligand;

determining gradients of the quality score for the output ligand by backpropagating the gradients of the quality score through the scoring model and the generative machine learning model and into an internal latent vector of the generative machine learning model corresponding to a target denoising iteration, wherein the target denoising iteration is any denoising iteration before a final denoising iteration in the sequence of denoising iterations;

updating the internal latent vector at the target denoising iteration using the gradients of the quality score; and iteratively denoising the updated internal latent vector, using the generative machine learning model and starting from the target denoising iteration in the sequence of denoising iterations, to generate an optimized denoised latent vector that defines an optimized ligand; and outputting data defining the optimized ligand.

2. The method of claim 1, wherein obtaining data identifying an input ligand comprises:

obtaining data identifying a three-dimensional (3D) structure of the input ligand, comprising data defining a respective 3D spatial position of each of a plurality of atoms in the input ligand.

3. The method of claim 2, wherein obtaining data identifying the input ligand further comprises:

obtaining data identifying a respective atom type of each of a plurality of atoms in the input ligand.

4. The method of claim 1, wherein the operations further comprise:

processing a model input characterizing the output ligand using a scoring model to generate a quality score for the output ligand;

determining gradients of the quality score for the output ligand with respect to the noised latent vector that was iteratively denoised by the generative machine learning model to generate the final denoised latent vector defining the output ligand;

generating a modified latent vector by combining the gradients of the quality score with the noised latent vector; and generating, by the generative machine learning model and when the generative machine learning model is conditioned on the modified latent vector, data defining a second optimized ligand.

5. The method of claim 4, wherein the scoring model is a differentiable model.

6. The method of claim 4, wherein the quality score for the output ligand characterizes a predicted binding affinity of the output ligand for a target molecule.

7. The method of claim 4, wherein the quality score for the output ligand characterizes a synthetic accessibility of the output ligand.

8. The method of claim 4, wherein determining gradients of the quality score for the output ligand with respect to the noised latent vector comprises:

backpropagating through the scoring model and the generative machine learning model into the noised latent vector.

9. The method of claim 4, wherein the generative machine learning model comprises a generative diffusion model; and wherein generating, by the generative machine learning model and when the generative machine learning model is conditioned on the modified latent vector, data defining a second output ligand comprises:

iteratively denoising the modified latent vector over a plurality of denoising iterations to generate, at a final denoising iteration, a denoised version of the modified latent vector that defines the second output ligand.

10. The method of claim 1, wherein the quality score for the output ligand characterizes a predicted binding affinity of the output ligand for a target molecule.

11. The method of claim 10, wherein the target molecule is a protein.

12. The method of claim 1, wherein the quality score for the output ligand characterizes a synthetic accessibility of the output ligand.

13. The method of claim 1, further comprising physically synthesizing the optimized ligand.

14. The method of claim 13, further comprising performing physical experiments on the optimized ligand to experimentally validate the optimized ligand.

15. A system comprising:

one or more computers; and one or more storage devices communicatively coupled to the one or more computers, wherein the one or more storage devices store instructions that, when executed by the one or more computers, cause the one or more computers to perform operations comprising:

identifying one or more ligands for binding to a target molecule by performing operations comprising:

obtaining data identifying an input ligand;

generating, using a generative machine learning model, a noised latent vector by combining random noise with data representing the input ligand, wherein the generative machine learning model has been trained, by a machine learning training technique on a training dataset of ligand structures, to generate a predicted structure of a ligand by denoising an initial latent vector over a sequence of denoising iterations;

iteratively denoising the noised latent vector using the generative machine learning model over the sequence of denoising iterations to generate a final denoised latent vector that defines an output ligand;

processing a model input characterizing a 3D structure of the output ligand using a scoring model to generate a quality score for the output ligand;

determining gradients of the quality score for the output ligand by backpropagating the gradients of the quality score through the scoring model and the generative machine learning model and into an internal latent vector of the generative machine learning model corresponding to a target denoising iteration, wherein the target denoising iteration is any denoising iteration before a final denoising iteration in the sequence of denoising iterations;

updating the internal latent vector at the target denoising iteration using the gradients of the quality score; and iteratively denoising the updated internal latent vector, using the generative machine learning model and starting from the target denoising iteration in the sequence of denoising iterations, to generate an optimized denoised latent vector that defines an optimized ligand; and outputting data defining the optimized ligand.

16. One or more non-transitory computer storage media storing instructions that when executed by one or more computers cause the one or more computers to perform operations comprising:

identifying one or more ligands for binding to a target molecule by performing operations comprising:

obtaining data identifying an input ligand;

generating, using a generative machine learning model, a noised latent vector by combining random noise with data representing the input ligand, wherein the generative machine learning model has been trained, by a machine learning training technique on a training dataset of ligand structures, to generate a predicted structure of a ligand by denoising an initial latent vector over a sequence of denoising iterations;

iteratively denoising the noised latent vector using the generative machine learning model over the sequence of denoising iterations to generate a final denoised latent vector that defines an output ligand;

processing a model input characterizing a 3D structure of the output ligand using a scoring model to generate a quality score for the output ligand;

determining gradients of the quality score for the output ligand by backpropagating the gradients of the quality score through the scoring model and the generative machine learning model and into an internal latent vector of the generative machine learning model corresponding to a target denoising iteration, wherein the target denoising iteration is any denoising iteration before a final denoising iteration in the sequence of denoising iterations;

updating the internal latent vector at the target denoising iteration using the gradients of the quality score; and iteratively denoising the updated internal latent vector, using the generative machine learning model and starting from the target denoising iteration in the sequence of denoising iterations, to generate an optimized denoised latent vector that defines an optimized ligand; and outputting data defining the optimized ligand.

* * * * *